US005886017A

United States Patent [19]
Driedger et al.

[11] Patent Number: 5,886,017
[45] Date of Patent: Mar. 23, 1999

[54] PROTEIN KINASE C MODULATORS. E.

[75] Inventors: Paul E. Driedger, Boston; James Quick, Lexington, both of Mass.

[73] Assignee: Procyon Pharmaceuticals, Inc., Woburn, Mass.

[21] Appl. No.: 940,440

[22] Filed: Sep. 4, 1992

Related U.S. Application Data

[63] Continuation-in-part of Ser. No. 559,701, Jul. 30, 1990, Pat. No. 5,145,842, which is a continuation-in-part of Ser. No. 322,881, Mar. 13, 1989, abandoned, which is a division of Ser. No. 61,299, Jun. 10, 1987, abandoned, which is a continuation-in-part of Ser. No. 872,812, Jun. 11, 1986, abandoned.

[51] Int. Cl.$^6$ ..................... A61K 31/695; A61K 31/675; A61K 31/40; A61K 31/395
[52] U.S. Cl. .............................. 514/410; 514/63; 514/81; 514/183
[58] Field of Search ............................... 514/63, 81, 183, 514/410

[56] References Cited

U.S. PATENT DOCUMENTS

| | | | |
|---|---|---|---|
| 4,376,821 | 3/1983 | Braude | 435/68 |
| 4,376,822 | 3/1983 | Braude | 435/68 |
| 4,401,756 | 8/1983 | Gillis | 435/68 |
| 4,460,685 | 7/1984 | Vilcek et al. | 435/68 |
| 5,145,842 | 9/1992 | Driedger et al. | 514/63 |
| 5,570,568 | 5/1998 | Driedger et al. | 514/533 |
| 5,643,948 | 7/1997 | Driedger et al. | 514/533 |
| 5,716,968 | 2/1998 | Driedger et al. | 514/323 |

FOREIGN PATENT DOCUMENTS

| | | |
|---|---|---|
| WO 87/07599 | 5/1988 | WIPO . |
| 91/05406 | 7/1991 | WIPO . |

OTHER PUBLICATIONS

Connolly et al, Antimicrob. Agents. Chemother. p. 245 (1992).
Saari et al, J Med. Chem 1992, 35. 3792–3802.
Mansuri et al, Chemtech. 1992, p. 564.
Merck Standby Statement, Sep. 14, 1993.
Dr. Sandstrom Letter of Jun. 19, 1990.
Kemp et al, Science 238: 1726 (1987).
Tinker et al, J. Biol. Chem. 263: 5024 (1998).
Wise et al, J. Biol. Chem. 257: 8489 (1982).
Loomis et al, J. Biol. Chem. 263: 1682 (1988).
Schatzman et al, Biochem. Biophy. Res. Comm. 98: 669 (1981).
Tamaoki et al. Biochem. Bioph. Res. Comm: 135: 397 (1986).
Srivastara, Biochem. Bioph. Res. Comm. 131:1 (1985).
Hidaka et al, Biochemistry 23:5036 (1984).
Mitsuya et al, AIDS, Modern Concepts and Therapeutic Challenges, Chapter 18, pp. 303–333 (1987).
J.A. Dunn and P.M. Blumberg, *Cancer Res.*, 43: 4632–4637 (1983).
T. Sugimura, *Gann,* 73: 499–507 (1982).
Y. Endo et al., *Chem. Pharm. Bull.* 32: 358–361 (1984).
E. Hecker and R. Schmidt, *Fortschritte D. ChemieOrganischer Naturstoffe 31:* 377–467 (1974).
F.J. Evans and C.J. Soper, *Lloydia 41:* 193–233 (1978).
R. Schmidt and E. Hecker, *Aktuelle Problems aus dem Gebiet der Cancerologie* III, pp. 98–108 (1971).
D. Uemura, H. Ohwaki and Y. Hirata, *Tetrahedron 29:* 2527–2528 (1974).
D. Uemura and Y. Hirata, *Tetrahedron 29:* 2529–2532 (1974).
Y. Hirata, *Pure and Appl. Org. Chem. 11:* 176–199 (1975).
S. Kupchan et al., *Science 191:* 571–572 (1976).
F. Evans, *Toxicon 16:* 51–57 (1978).
K. Sakata, et al., *Tetrahedron 16:* 1141–1144 (1971).
S. Kupchan et al., *JACS 97:*672–673 (1975).
S. Kupchan et al. *JACS 98:* 5719–5720 (1976).
S. Zayed et al., *Tetrahedron 39:* 3481–3482 (1977).
G. Stout et al., *JACS 92:* 1070–1071 (1970).
G. Furstenberger and E. Hecker, *Experientia 33:* 986–988 (1977).
J. Coetzer and M.J. Pieterse, *J. South Afr. Chem. Inst. 24:* 241–243 (1971).
H.–W. Thielmann et al., *Liebigs Ann. Chem. 728:* 158–183 (1969).
H.–W. Thielmann et al., *Forschritte der Krebsforschung,* Vo. VII, pp. 171–179, New York: Schattauer, 1969.
E. Hecker, *Carcinogenesis,* vol. II. Mechanisms of Tumor Promotion and Carcinogenesis, pp. 11–48. New York: Raven Press, 1978.
R. Schmidt and F. Evans, *Arch. Toxicol. 44:* 279–289 (1980).
H. Harada et al., *Bull. Chem. Soc. Japan 39:* 1773–1775 (1966).
S.de Laszlo, et al., *J. Chem. Soc., Chem. Commun.,* 344–346 (1986).
W. Adolf et al., *J. Natural Prod. 45:* 347–354 (1982).
W. Adolf and E. Hecker, *J. Med. Plant Res. 45:* 177–182 (1982).
E. Seip and E. Hecker, *J. Med. Plant Res. 46:* 215–218 (1982).
H. Opferkuel et al., *Z. Naturforsch 36:* 878–887 (1982).
B. Sorg and E. Hecker, *Z. Naturforsch 37:* 748–756 (1982).
B. Sorg and E. Hecker, *Z. Naturforsch 37* 1640–1647 (1982).
A. Jeffrey and R. Liskamp, *Proc. Natl. Acad. Sci. USA 83:* 241–245 (1986).
Y. Nishizuka, *Nature 308:* 693–698 (1984).
Y. Nishizuka, *Science 225:* 1365–1370 (1984).

(List continued on next page.)

*Primary Examiner*—Richard L. Raymond
*Attorney, Agent, or Firm*—Hamilton, Brook, Smith & Reynolds, P.C.

[57] ABSTRACT

Compositions of matter and pharmaceutical compositions having protein kinase C-modulatory, anti-inflammatory, anti-viral and other activities are disclosed. The compounds are derived from tricyclic aromatic heterocyclic compounds incorporating indole, indene, benzofuran and benzothiophene structural elements.

26 Claims, No Drawings

OTHER PUBLICATIONS

P. Driedger and P. Blumberg, *Cancer Research 39:* 714–719 (1979).

P. Driedger and P.M. Blumberg, *Cancer Research 37:* 3257–3265 (1977).

B. Ganong et al., *Proc. Natl Acad. Sci. 83:* 1184–1188 (1986).

R. Schmidt and E. Hecker, *Carcinogenesis 7:* 57–63 (1982).

T. Horiuchi et al., *Gann 75:* 837–840 (1984).

K. Irie et al., *Int. J. Cancer 36:* 485–488 (1985).

P. Wender et al., *Proc. Natl. Acad. Sci. 83:* 4214–4218 (1986).

T. Kakunaga et al., *Cellular Interactions by Environmental Tumor Promoters,* pp. 303–313. Tokyo: Japan Sci. Soc. Press, 1984.

F.J. Evans, *Naturally Occurring Phorbol Esters,* pp. 171–215. Boca Raton: CRC Press, 1986.

R. Schmidt, *Naturally Occurring Phorbol Esters,* pp. 217–243. Boca Raton: CRC Press, 1986.

R. Schmidt, *Naturally Occurring Phorbol Esters,* pp. 245–269. Boca Raton: CRC Press, 1986.

K. Irie et al, *Agric. Biol. Chem. 49:* 1441–1446 (1985).

R. Liskamp et al., *BBRC 131:* 920–927 (1985).

Yasutomi Nishizuka, *Science,* vol. 233 (1986) p. 305.

Yasutomi Nishizuka, *Nature,* vol. 334 (1988) p. 661.

Kazuhiro Irie et al., *Carcinogenesis,* vol. 8, No. 4 (1987) pp. 547–552.

Shin–ichi Nakatsuka et al., *Tetrahedron Letters,* vol. 28, No. 32 (1987) pp. 3671–3674.

Hirota, Fujiki et al., *Gann,* 75: 866–870 (1984).

Kazuhiro Irie et al., *Argic. Biol. Chem.* (*50*(*10*): 2679–2680 (1986).

Shin–ichiro Sakai et al., *Chem. Pharm. Bull 34*(*11*): 4883–4886 (1986).

Matao Takashima et al., *Arg. Biol. Chem.,* vol. 26, No. 10, p. 660 (1962).

Yasuyuki Endo et al., *Tetrahedron Letters,* vol. 43, No. 10, p. 2241 (1987).

Kazuhiro Irie et al., *Agric Biol. Chem.,* 48(5): 1269–1274 (1984).

Kazuhiro Irie et al., *Tetrahedron Letters,* vol. 43, No. 22, pp. 5251–5260 (1987).

Yasutomi Nishizuka, *JAMA,* vol. 262, No. 13, p. 1826 (1989).

Chemical Abstracts, vol. 70, No. 11, 17 Mar. 1969, (Columbus, OH, US); abstract No. 47622q.

A.P. Kozikowski et al., *J. Am. Chem. Soc.,* vol. 111, No. 16, pp. 6228–6234 (2 Aug. 1989), "Synthesis and Biological Studies of Simplified Analogues of Lyngbyatoxin A: Use of an Isoxazoline–based indole synthesis. Quest for protein kinase C modulators".

PROTEIN KINASE C MODULATORS. E.

RELATED APPLICATIONS

This application is a continuation-in-part of application Ser. No. 07/559,701, filed Jul. 30, 1990, now U.S. Pat. No. 5,145,842, which is a continuation-in-part of application Ser. No. 07/322,881, filed Mar. 13, 1989, now abandoned, which is a division of application Ser. No. 07/061,299, filed Jun. 10, 1987, now abandoned, which is a continuation-in-part of application Ser. No. 06/872,812, filed Jun. 11, 1986, now abandoned, all of which are herein incorporated by reference.

BACKGROUND

Protein kinase C is an enzyme found in nearly all animal tissues and animal cells that have been examined. Its identity is generally established by its ability to phosphorylate proteins when adenosine triphosphate, calcium ions and phospholipid cofactors are present, with greatly reduced activity when these cofactors are absent. Protein kinase C activity is substantially stimulated by certain 1,2-sn-diacylglycerols that bind specifically and stoichiometrically to a recognition site on the enzyme. Stimulation of protein kinase C by these diacylglycerols has been shown to be an important physiological event that mediates the actions of a wide variety of hormones, neurotransmitters, and other biological control factors such as histamine, vasopressin, alpha-adrenergic agonists, dopamine agonists, muscarinic cholinergic agonists, platelet activating factor, etc. [see Y. Nishizuka, *Nature* 308 693–698 (1984) and *Science* 225 1365–1370 (1984) for reviews].

The biological role of protein kinase C is also of great interest because of the discovery that certain very powerful tumor promoting substances activate this enzyme by binding specifically and with very high affinity to the diacylglycerol binding site on the enzyme. In addition to diacylglycerols, there are at present five other known classes of compounds that bind to this site, including diterpenes such as the phorbol esters, indole alkaloids (indolactams) such as the teleocidins, lyngbyatoxin, and indolactam V, polyacetates such as the aplysiatoxins and oscillatoxins, certain derivatives of diaminobenzyl alcohol, and the macrocyclic lactones of the bryostatin class. The phorbol esters have long been known as powerful tumor promoters, the teleocidins, aplysiatoxins and diacylglycerols are now known to have this activity, and it appears likely that additional classes of compounds will be found to have the toxic and tumor promoting activities associated with the capability to bind to the diacylglycerol site of protein kinase C and thus activate the enzyme. Other toxicities of these agents when administered to animals include lung injury and profound changes in blood elements, such as leukopenia and neuropenia.

In addition to potent tumor promoting activity, these six classes of compounds, collectively referred to as the "phorboids", display a vast range of biological activities, as would be expected from the widespread distribution of their target enzyme. Some of these activities, like tumor promotion, indicate the involvement of protein kinase C in important normal or pathological processes in animals. Thus, the phorboids are potent skin inflammatory agents, cause smooth muscle contraction in several tissues, alter immune system function and can be used to cause a variety of other normal or pathological responses. Related disease states such as the development of cancer, the onset and/or maintenance of inflammatory disease, the role of vasoconstriction in hypertension, the role of bronchoconstriction in asthma, the role of cholinergic, adrenergic, and dopaminergic synapses in diseases of the central/peripheral nervous systems, may be mediated in vivo by the stimulation of protein kinase C by diacylglycerols, the latter being generated in the cell by pathological agents or conditions.

In analyzing the activity of a pharmaceutical or other bioactive compound, it is useful to consider two properties: the efficacy, defined as the capability to elicit a full or partial biological result, such as complete displacement of a ligand from its receptor site or the complete inhibition of inflammation or edema caused by a standard stimulus; and the potency, defined as that amount or concentration of drug that causes 50% of the full response (often abbreviated as the $ED_{50}$). It is frequently the case within a given class of pharmaceutical agents that individual members of the class all have equal efficacy, i.e. they each can generate a full biological effect, but they show differing potencies. Thus, the structural modifications within such a class affect only the amount necessary to achieve a given result, and the modified compounds otherwise have generally the same central biological characteristic. There may also be differences between members of such a class as regards properties other than the central biological characteristic; for example, members of the class might differ in side effects or toxicity.

Well-known pharmaceuticals that have been in extensive use for years or decades show a wide range of optimal therapueutic potencies. Aspirin, for example, is often taken in multi-gram amounts per day for treatment of inflammation or arthritis, and detailed analyses of its mechanism of action in vitro show that a concentration in the millimolar range is required. In contrast, steroid-based topical anti-inflammatory compounds such as fluocinolone acetonide are many thousand-fold more potent, and, beyond this, some oral contraceptive agents are prescribed in daily doses in the micro-gram range. Thus, although high potency is generally advantageous for a pharmaceutical, it is not an absolute requirement.

Several thousand of the high skin-inflammatory and tumor-promoting phorboids have been reported in the literature, including numerous examples on which minor chemical modifications have been made [see Evans and Soper, *Lloydia* 41 193–233 (1978) and references cited therein]. The structures of these phorboids can be compared, and their activities for inflammation and tumor promotion can be analyzed from the perspective of efficacy and potency. The structures of the different classes of phorboids vary quite markedly from one to the other class (see Summary of the Invention for structural comparisons), yet widespread testing of their biological activities has shown that these classes have generally very similar biological properties. In particular, the thousands of known phorboids of the highly potent diterpene, indolactam, and polyacetate classes appear to have, with very minor exceptions, virtually identical efficacies as skin irritants and tumor promoters [T. Sugimura, *Gann* 73 499–507 (1982)]. The exceptions involve a few compounds that have a short duration of irritant activity and/or manifest diminished tumor promoting activity, perhaps due to toxicity or secondary parameters such as differing metabolic destruction rates.

In contrast to the essentially equal efficacies among the vast majority of phorboids, their relative potencies cover a wide range, as measured in inflammation and promotion tests and as measured in numerous other in vivo and in vitro systems. Example compounds can be found in the diterpene, indolactam, and polyacetate classes that have nearly equal, very high potencies. At the same time there are compounds in each of these classes which embody significant structural changes that do not diminish efficacy but do result in potency decreases of 10-fold to 100,000-fold or more [see, for example, Driedger and Blumberg, *Cancer Res.* 37 3257–3265 (1977), *Cancer Res.* 39 714–719 (1979)]. Thus, all these compounds appear to be capable of achieving generally the same biological results, and merely differ in the amount which must be used to obtain a given result.

In vitro measurements of biochemical properties provide an even more sensitive method for comparing the properties of the various phorboids. For example, using a radioactively labeled phorboid such as [$^3$H]phorbol 12,13-dibutyrate or [$^3$H]lyngbyatoxin, one can measure the potency of a test compound as a competitive ligand for the diacylglycerol binding site on protein kinase C. Alternatively, one can measure the ability of a given phorboid to stimulate the protein kinase C-mediated incorporation of radioactive phosphate from [$^{32}$P]adenosine triphosphate into a standard acceptor substrate such as histone H1. Tests of this nature reveal a difference in potency between given phorboid agonists of as much as 10,000,000-fold or more [Dunn and Blumberg, *Cancer Res.* 43 4632–4637 (1983), Table 1].

These basic data regarding the phorboid agonists are an important consideration because they underscore the concept that the structural differences among these previously known phorboids, especially the diterpenes, indolactams, polyacetates, and bryostatins, generally do not affect their efficacies as toxic agonists, and indeed a wide variety of structural changes are tolerated in this regard. Such changes generally alter potency only and do not provide agents with therapeutic utility, since they retain their toxicity.

Some minor changes in phorboid structure are known to result in inactive compounds, such as a stereochemical change from 4-beta to 4-alpha in the phorbol series, and indeed some of the diterpene skeleton structures carry hydroxy groups that must be esterified in order for inflammatory activity to be observed. However, these inactive compounds are quite few in number among the known phorboids, and no therapeutic utility has been demonstrated for them.

The phorbol esters, indolactams, polyacetates, diaminobenzyl alcohols, and bryostatins are generally found in plants, molds, and algae, or are synthetic in origin. Although they are found in many parts of the world, normal human contact with them is thought to be low. In contrast, the diacylglycerols are part of the functioning of virtually every type of animal cell except erythrocytes of some species, and thus the undesirable activation of protein kinase C by the diacylglycerols may have a very widespread role in human diseases.

Thus, new compounds, capable of blocking the activation of protein kinase C by acting as specific pharmacological antagonists of the diacylglycerols, would be valuable agents in the prevention and treatment of a wide variety of diseases in animals and humans.

There may be several different forms of protein kinase C each having different biological roles. The stimulation of one form can lead to undesirable results such as inflammation or the development of cancer, while stimulation of another form of the enzyme might produce beneficial effects, such as the abrogation of inflammation or the secretion of useful bioregulatory factors such as hormones and interferons.

Moreover, the exact correspondence between diacylglycerol binding sites and protein kinase C has not been fully explored, and there may be several different such binding sites with differential affinities for diacylglycerols and other phorboids. Indeed there is published evidence for several distinct classes of phorboid binding sites in various tissues and cell types (Dunn and Blumberg, op. cit.). However, in this study, even the ligands showing the clearest differences in affinity for these distinct classes are only selective by a factor of 10-100 in dissociation constant. Thus, other new compounds, capable of selectively activating one useful, but not another, deleterious, diacylglycerol target site, would also be valuable agents for the prevention or treatment of inflammation.

Earlier efforts to use the previously known phorboids themselves or to modify the structures of the known phorboids, have not been successful in producing useful compounds.

It has been known for some time that several of the toxic, inflammatory and tumor-promoting compounds such as phorbol 12-tigliate 13-decanoate, mezerein, lyngbyatoxin and aplysiatoxin have anti-leukemic activity in mouse model tests. However, these compounds are all extremely toxic and are cancer suspect agents, thus eliminating them from consideration as human therapeutic agents.

Ganong et al. [*Proc. Nat. Acad. Sci.* 83 1184–1188 (1986)] tested a series of diacylglycerols and found no antagonistic activity in that series against the standard agonist 1,2-dioctanoylglycerol. It is of particular note that several compounds tested in this work were modified in the hydroxymethyl portion of the diacylglycerol molecule, and these modifications produced only a loss of activity or a weakened activity that was not distinguishable from the agonist activity of 1,2-dioctanoylglycerol itself. These hydroxymethyl-modified compounds were not antagonists in these tests and no utility was found. Similarly, Thielmann and Hecker [*Forsch. Krebsforsch.* Vol. VII, pp. 171–179 (1969), New York: Schattauer] found only a complete loss of biological activity in their study when the hydroxy group of the hydroxymethyl on phorbol 12,13-didecanoate was replaced with hydrogen or chlorine. Schmidt and Hecker [H. Lettre and G. Wagner (eds.), *Aktuelle Probleme aus dem Gebiet der Cancerologie*, Vol. III, 3rd Heidelberg Symposium, pp. 98–108. Berlin: Springer Verlag, 1971.] also found that oxidation of the hydroxymethyl of phorbol 12,13-didecanoate to a carboxylic acid caused complete loss of activity in the assays used.

The hydroxymethyl group of the known phorboids (discussed in more detail in Summary of the Invention) has been thought to be required for biological activity, as detailed by Hecker (*Carcinogenesis.* Vol. 2, eds. Slaga, Sivak and Boutwell, Raven Press, New York, 1978, pp. 11–48 and references cited therein). Indeed, it is stated therein that the replacement of the 20-hydroxyl in a phorbol ester "results in complete loss of biological activity". In another study, replacement of the hydroxy group of the hydroxymethyl (located at carbon 14) by chlorine or hydrogen in indolactam V gave rise to compounds with agonist activity weaker than but otherwise not distinguished from the agonist activity of the very toxic teleocidin class of tumor promoters [Irie et al., *Int. J. Cancer* 36 485–488 (1985)]. Thus no utility was found.

Schmidt and Hecker (*Carcinogenesis*, Vol. 7, ed. by E. Hecker et al., Raven Press, New York, 1982, pp. 57–63) studied the abilities of a series of diterpene phorboids to inhibit tumor promotion by the standard phorboid agonist tumor promoter phorbol 12-myristate 13-acetate (PMA). They found that, at low doses, some short-chain ester derivatives of phorbol were able to block the tumor promotion by PMA. However, all of the compounds that were active as antagonists at low doses are also very efficacious skin irritants themselves at higher doses and most of them are also known to have tumor promoting activity. Thus, these short-chain esters still have toxic inflammatory and tumor promoting activity and thus have no therapeutic value. In this publication it was also noted that a phorbol 12-ester, namely phorbol 12-myristate, was without activity as an antagonist of PMA-induced tumor promotion. Thielmann and Hecker (op. cit.) also found phorbol 12-decanoate and phorbol 12-myristate to be inactive in the functional tests used, and stated that the 13-OH must be esterified to obtain active compounds.

SUMMARY OF THE INVENTION

This invention pertains to phorboid derivatives which block the toxic effects of the hydroxymethyl-containing phorboids and lack the toxic properties of previously available phorboids. These phorboid derivatives of very diverse structures have utility as anti-inflammatory agents, as cancer cell and leukemic cell inhibitory agents, anti-asthmatic and anti-hypertensive agents, as modulators of human immune cell function, as stimulators of the production of lymphokines such as interferon and the interleukins, as central nervous system pharmaceuticals for several pathological conditions, and as xenobiotics for achieving the control of parasites. The structural features associated with the non-toxicity and protein kinase C antagonism of these compounds relate primarily to the hydroxymethyl or 1-hydroxyethyl group found in each of the toxic parent compounds. Specific modification of the latter chemical groupings yields non-toxic (e.g., they generally do not cause skin inflammation when tested alone) compounds that show anti-inflammatory activity, whereas any of a very wide variety of changes in other parts of the parent structures, including but not limited to diterpenes, indole alkaloids, polyacetates, diaminobenzyl alcohol derivatives, aplysiatoxins, and bryostatinoids, have very markedly less effect on the overall biological properties of the derivatives, other than changes in potency. This invention also provides new compounds that discriminate between phorboid receptor subtypes, with relative binding activities differing by 10,000-fold or more.

A comparison of the structures of the previously known phorboids reveals the features that are critical for this invention, as shown below, in which the hydroxymethyl and 1-hydroxyethyl groups are enclosed in dashed lines.

TYPICAL DITERPENE-TYPE PHORBOID AGONISTS

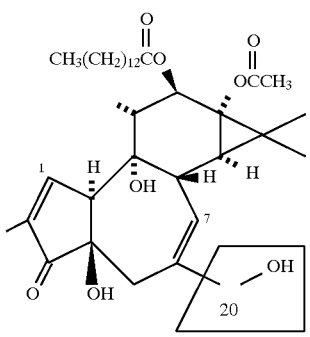

Phorbol 12-Myristate 13-Acetate (PMA)

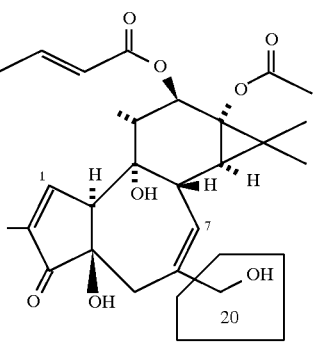

Phorbol 12-Retinoate 13-Acetate

-continued
TYPICAL DITERPENE-TYPE PHORBOID AGONISTS
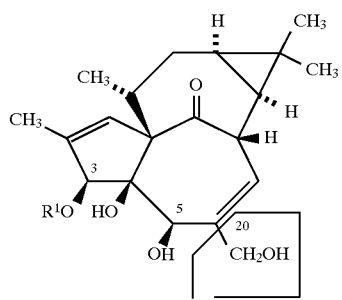
$R^1 = \cdots COC_{13}H_{27}$
Ingenol 3-Tetradecanoate
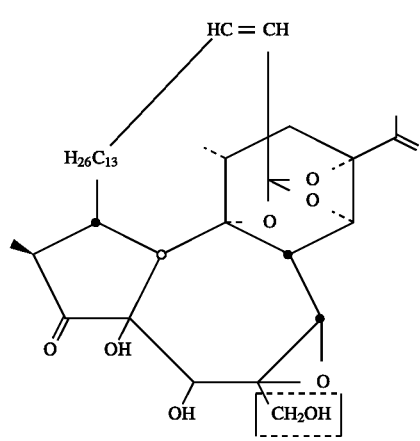
SYNAPTOLEPIS FACTOR K$_1$
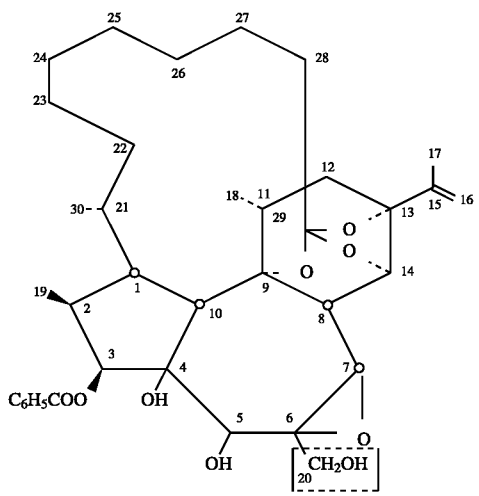
PIMELEA FACTOR P$_2$

-continued
TYPICAL DITERPENE-TYPE PHORBOID AGONISTS
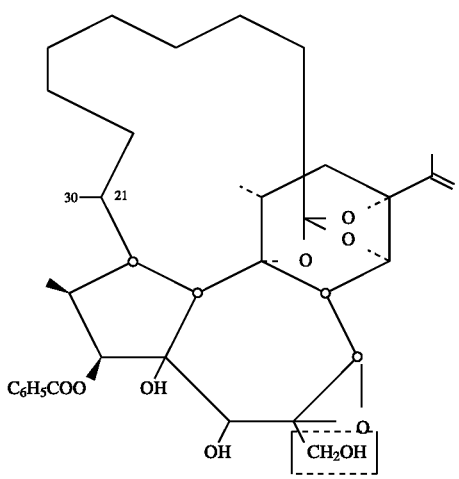
DAPHNOPSIS FACTOR R₆
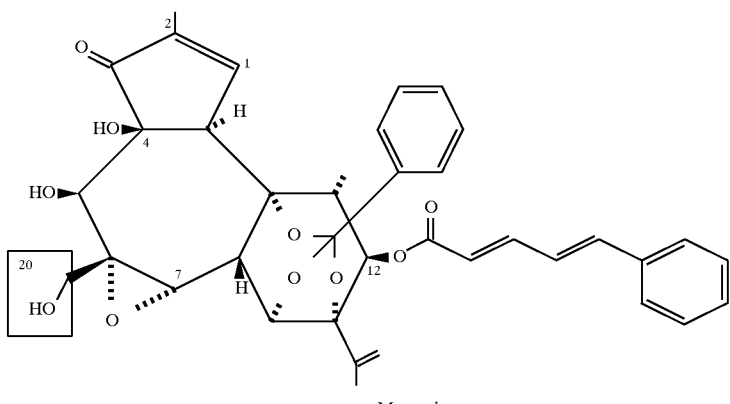
Mezerein
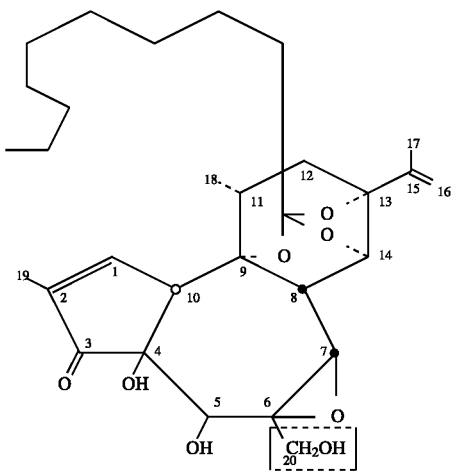
SIMPLEXIN -continued
TYPICAL DITERPENE-TYPE PHORBOID AGONISTS
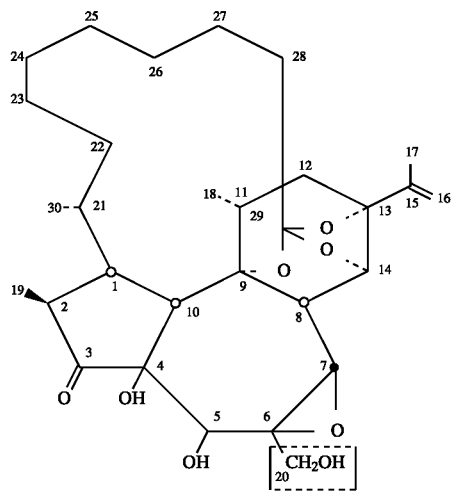
PIMELEA FACTOR S$_7$
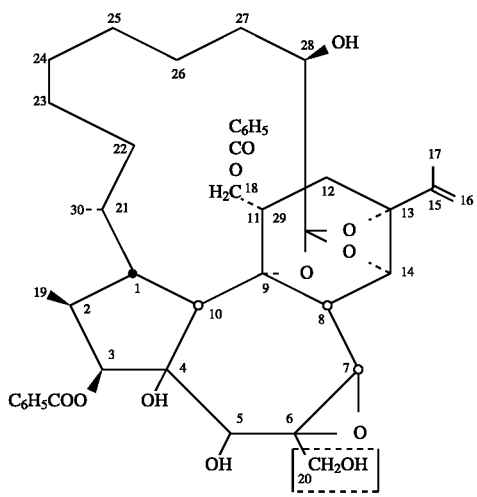
GNIDIMACRIN
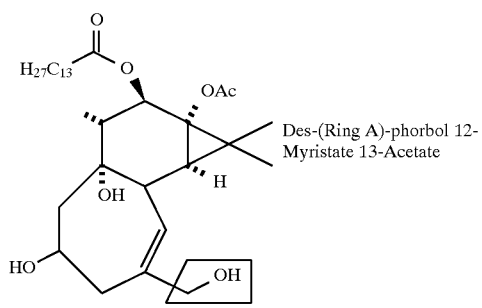
TYPICAL INDOLACTAM-TYPE PHORBOID AGONISTS -continued
TYPICAL DITERPENE-TYPE PHORBOID AGONISTS
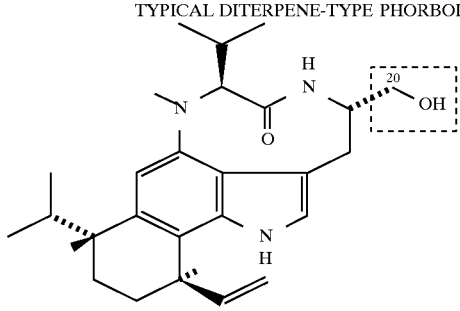
Teleocidin
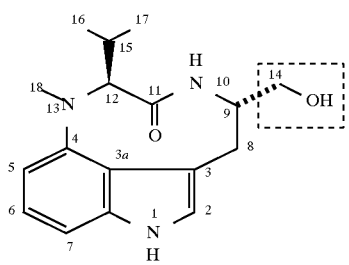
Indolactam V
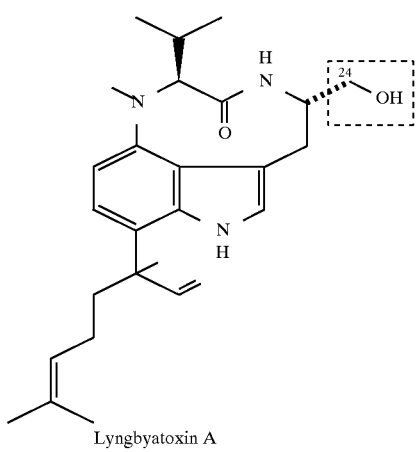
Lyngbyatoxin A
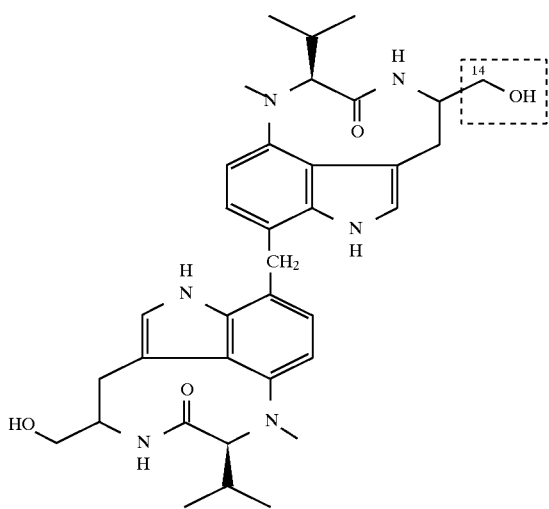
Blastmycetin A
TYPICAL DIAMINOBENZYL ALCOHOL-TYPE PHORBOID AGONISTS

-continued
TYPICAL DITERPENE-TYPE PHORBOID AGONISTS

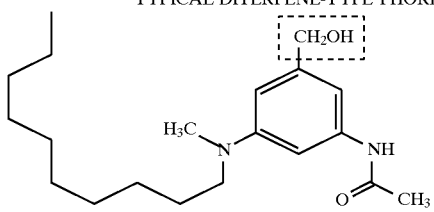

3-Acetylamino-5-(N-decyl-N-methylamino)benzyl Alcohol

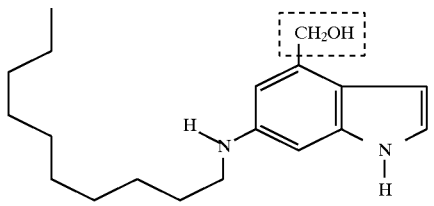

6-(N-decylamino)-4-hydroxymethylindole

TYPICAL DIACYLGLYCEROL-TYPE PHORBOID AGONISTS

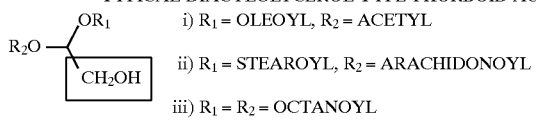

i) $R_1$ = OLEOYL, $R_2$ = ACETYL ii) $R_1$ = STEAROYL, $R_2$ = ARACHIDONOYL iii) $R_1$ = $R_2$ = OCTANOYL

TYPICAL POLYACETATE-TYPE PHORBOID AGONISTS

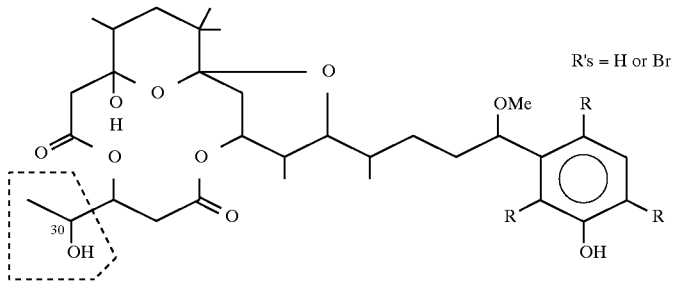

R's = H or Br (Aplysiatoxin and its debromo, bromo, and dibromo derivatives)

TYPICAL BRYOSTATIN-TYPE PHORBOID AGONISTS

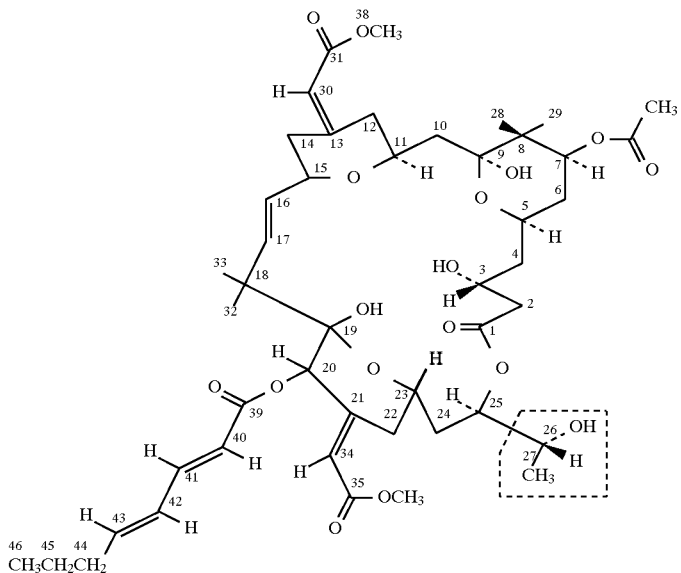

Bryostatin 1

-continued
TYPICAL DITERPENE-TYPE PHORBOID AGONISTS

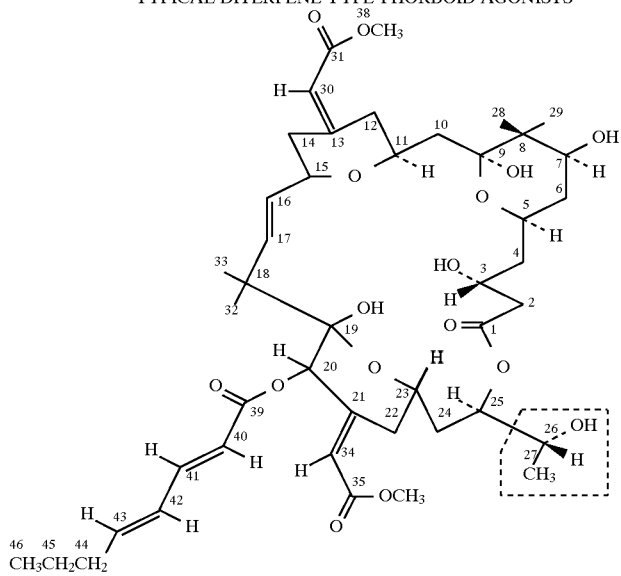

Bryostatin 2

It can be seen that the phorboids depicted have exceedingly diverse structural elements of both hydrophilic and hydrophobic nature, with one prominent exception, namely that each contains a hydroxymethyl or 1-hydroxyethyl group (indicated by the dashed-line boxes in each structure). In each case the phorboid depicted is among the most potent of its particular structural class, and among the classes the diterpenes, indolactams and polyacetates have members of especially high potency.

The hydroxymethyl and 1-hydroxyethyl feature common to all the classes of phorboids is the primary focus of this invention. Generally the phorboid derivatives of this invention can be represented by the formula:

P—G wherein P represents a radical, formally derived from a parent compound, which compound:
 a. binds reversibly or irreversibly to a diacylglycerol-type receptor; and/or
 b. activates any form of the enzyme protein kinase C; and
 c. contains an hydroxymethyl or 1-hydroxyethyl group bonded to a carbon atom; and
wherein G is any group of 55 or fewer atoms selected from carbon, hydrogen, oxygen, nitrogen, halogen, sulfur, phosphorus, silicon, arsenic, boron and selenium either i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group is bound in the parent compound; and wherein the hydroxymethyl or 1-hydroxyethyl group of the parent compound is absent or has been replaced by G.

More specifically, the compounds of this invention are represented by the formula:

$P_o$-$S_o$-$E_o$ which depicts a phorboid "parent" compound radical $P_o$ modified by a moiety $S_o E_o$.

In general, a parent compound is a compound which:
 a. binds reversibly or irreversibly to a diacylglycerol-type receptor; and/or
 b. activates any form of the enzyme protein kinase C; and
 c. contains an hydroxymethyl or 1-hydroxyethyl group bonded to a carbon atom.

For example, a parent compound can be a diterpenoid activator of protein kinase C; an aromatic heterocyclic activator of protein kinase of the indole, indene, benzofuran, or benzothiophene class, further defined here by the mandatory presence of a substituted or unsubstituted six-atom chain connecting positions 3 and 4 of the indole, indene, benzofuran or benzothiophene skeleton to form an additional 9-membered ring and by the optional presence in this class of one or two nitrogen atoms at any of positions 5, 6 and 7 of the benzenoid ring portion of the indole, indene, benzofuran or benzothiophene skeletons; a polyacetate-derived activator of protein kinase C; an activator of protein kinase C of the diacylglycerol or diacyloxybutanol class; an activator of protein kinase C of the diaminobenzyl alcohol class; or a protein kinase C activator of the bryostatin class.

$S_o$-$E_o$ represents a modifying moiety which is either:
 i) singly or doubly bonded to the carbon atom of the parent compound $P_o$ in place of the hydroxymethyl or 1-hydroxyethyl group; or
 ii) singly or doubly bonded to a carbon immediately adjacent to the carbon atom to which the hydroxymethyl or 1-hydroxyethyl is bonded.

In the $S_o$-$E_o$ moiety, $S_o$ can be a substituted or unsubstituted, saturated, unsaturated and/or aromatic, straight or branched, acyclic, ring-containing and/or ring-carrying chain of atoms which separates $P_o$ and $E_o$ by a linear count of at least two but not more than 12 atoms and contains and/or carries not more than 9 heteroatoms selected from oxygen, nitrogen, silicon, sulfur, phosphorus, arsenic, boron and selenium, and not more than 16 halogen atoms; provided that the total number of atoms does not exceed 35; and in some cases $S_o$ may be a single or double bond; and $E_o$ can be hydrogen, halogen or a saturated or singly or multiply unsaturated group containing up to 15 carbon atoms and optionally containing 1 to 12 halogen atoms and/or 1 to 6 heteroatoms selected from oxygen, nitrogen, silicon, sulfur, phosphorus, arsenic, boron and selenium. $S_oE_o$ taken together may also be a hydrogen, halogen, thionic sulfur atom or ketonic oxygen atom or a hydroxy, amino, or thiol group singly or doubly bonded to the carbon atom of the parent compound $P_o$ in place of the hydroxymethyl or 1-hydroxyethyl group.

DETAILED DESCRIPTION OF THE INVENTION

All six classes of the phorboids have one structural element in common. Each prototypical member of these classes has either a hydroxymethyl group or a 1-hydroxyethyl group. The design of the phorboid derivatives of this invention is based on the finding that the hydroxymethyl and 1-hydroxyethyl groups which previously were thought to be required for biological activity of phorboids containing these groups can be replaced by other substituents of very diverse nature, and the resulting compounds both block the toxic effects of the hydroxymethyl-containing phorboids and lack the toxic properties associated with the previously available phorboids. These new compounds thus have utility as anti-inflammatory agents, for example. Although the replacement of the hydroxymethyl group or 1-hydroxyethyl group is very specific and leads to an extreme and profound change in biological properties, a very wide range of structural alterations in the remainder of the novel compounds can be tolerated without material loss of their anti-inflammatory activity.

The phorboid derivatives of this invention are generally represented by the formula:

$$P—G$$

The formula depicts a radical, P, derived from a parent compound, which compound:
 a. binds reversibly or irreversibly to a diacylglycerol-type receptor; and/or
 b. activates any form of the enzyme protein kinase C; and
 c. contains an hydroxymethyl or 1-hydroxyethyl group bonded to a carbon atom; and
wherein G is any group of 55 or fewer atoms selected from carbon, hydrogen, oxygen, nitrogen, halogen, sulfur, phosphorus, silicon, arsenic, boron and selenium either i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group is bound in the parent compound; and wherein the hydroxymethyl or 1-hydroxyethyl group of the parent compound is absent or has been replaced by G.

More specifically, the phorboid derivatives of this invention are represented by the formula:

$$P_o\text{-}S_o\text{-}E_o$$

The formula depicts a radical $P_o$, formally derived from a parent hydroxymethyl-containing phorboid compound, bonded to an $S_o\text{-}E_o$ moiety.

$P_o$ represents a radical formally derived from a parent compound which contains an hydroxymethyl (or the equivalent 1-hydroxyethyl) group and which binds reversibly or irreversibly to a diacylglycerol-type receptor and/or activates any form of the enzyme protein kinase C. $P_o$ may be formally derived from phorboids from any of the six classes listed below:

i) a diterpenoid activator of protein kinase C;
ii) an aromatic heterocyclic activator of protein kinase of the indole, indene, benzofuran, or benzothiophene class, further defined here by the mandatory presence of a substituted or unsubstituted six-atom chain connecting positions 3 and 4 of the indole, indene, benzofuran or benzothiophene skeleton to form an additional 9-membered ring and by the optional presence in this class of one or two nitrogen atoms at any of positions 5, 6 and 7 of the benzenoid ring portion of the indole, indene, benzofuran or benzothiophene skeletons;
iii) a polyacetate-derived activator of protein kinase C;
iv) an activator of protein kinase C of the diacylglycerol or diacyloxybutanol class;
v) an activator of protein kinase C of the diaminobenzyl alcohol class; and
vi) a protein kinase C activator of the bryostatin class.

All of these phorboid-type parent compounds contain an hydroxymethyl or 1-hydroxyethyl group which is known to be required for their toxic biological activity, such as inflammatory activity measured on the mouse ear.

$S_o\text{-}E_o$ represents a moiety which is either:
 i) singly or doubly bonded to the carbon atom of the parent compound in place of the hydroxymethyl or 1-hydroxyethyl group; or
 ii) singly or doubly bonded to a carbon immediately adjacent to the carbon atom to which the hydroxymethyl or 1-hydroxyethyl group is bound in the parent compound.

In this $S_oE_o$ moiety, $S_o$ can be a substituted or unsubstituted, saturated, unsaturated and/or aromatic, straight or branched, acyclic, ring-containing and/or ring-carrying chain of atoms which separates $P_o$ and $E_o$ by a linear count of at least two but not more than 12 atoms and contains and/or carries not more than 9 heteroatoms selected from oxygen, nitrogen, silicon, sulfur, phosphorus, arsenic, boron and selenium, and not more than 16 halogen atoms; provided that the total number of atoms does not exceed 35; and in some cases $S_o$ may be a single or double bond; and $E_o$ can be hydrogen, halogen or a saturated or singly or multiply unsaturated group containing up to 15 carbon atoms and optionally containing 1 to 12 halogen atoms and/or 1 to 6 heteroatoms selected from oxygen, nitrogen, silicon, sulfur, phosphorus, arsenic, boron and selenium. $S_oE_o$ taken together may also be a hydrogen, halogen, thionic sulfur atom or ketonic oxygen atom or a hydroxy, amino, or thiol group singly or doubly bonded to the carbon atom of the parent compound $P_o$ in place of the hydroxymethyl or 1-hydroxyethyl group.

In a preferred embodiment, the phorboid derivatives of this invention are represented as follows:

$$P_x\text{-}S_x\text{-}E_1$$

wherein $P_x$ can be selected from six different classes of compounds designated $P_1$–$P_6$ and defined below, wherein $S_x$ is selected from seven different structural types as defined below and $E_1$ is as defined below.

$P_1, P_2, P_3, P_4, P_5$, and $P_6$ represent compounds of each of the six classes of known phorboids and are defined by the formula below.

$P_1$ is a radical of the formula:

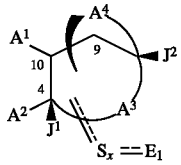

(P$_1$)

in the form of an individual isomer, an isomer mixture, a racemate or optical antipode, or a pharmaceutically acceptable salt thereof, wherein $A^1$ and $A^2$ may be independently selected from hydrogen, halogen and a straight chain or branched chain, cyclic or acyclic, saturated, unsaturated and/or aromatic carbon- and/or heteroatom-containing substituent having not more than 34 carbon atoms, not more than 24 halogen atoms and not more than 9 heteroatoms selected from oxygen, nitrogen, silicon, phosphorus and sulfur, or $A^1$ and $A^2$ taken together may complete a 5- or 6-membered carbocyclic or heterocyclic ring, optionally substituted by halogen/s and/or by 1–8 straight chain or branched chain, cyclic or acyclic, saturated, unsaturated, and/or aromatic carbon- and/or heteroatom-containing groups, which halogen/s and groups taken together contain a total of not more than 30 carbon atoms, not more than 24 halogen atoms and not more than 9 heteroatoms selected from oxygen, nitrogen, silicon, phosphorus and sulfur; $A^3$ is a three atom chain which carries $S_xE_1$ and completes a 7-membered carbocyclic ring optionally substituted by 1–6 substituents independently selected from halogen/s and straight chain or branched chain, cyclic or acyclic, saturated, unsaturated, and/or aromatic carbon- and/or heteroatom-containing groups, which halogens and groups taken together, excluding $S_xE_1$, contain not more than 12 carbon atoms, not more than 8 halogen atoms, and not more than 5 heteroatoms selected from oxygen, nitrogen, silicon, phosphorus and sulfur; provided that, including $S_xE_1$, the middle carbon atom of $A^3$ is not substituted by hydroxymethyl or 1-hydroxyethyl; $A^4$ completes a 6- or 7-membered carbocyclic or heterocyclic ring (connected in the beta configuration to either carbon atom 9 or 10), optionally substituted by halogen/s and/or by 1–10 straight chain or branched chain, cyclic or acyclic, saturated, unsaturated and/or aromatic carbon- and/or heteroatom-containing groups, the group or groups optionally completing 1–3 additional rings through bonds among themselves and/or 1–5 additional rings when taken together with $A^1$, $A^2$, a ring formed by $A^1$ and $A^2$ together, and/or a bond to carbon atom 9, which halogen/s and groups taken together, include not more than 50 carbon atoms, not more than 24 halogen atoms, and not more than 15 heteroatoms selected from oxygen, nitrogen, silicon, phosphorus and sulfur; $J^1$ is selected from hydrogen, fluoro, chloro, hydroxy, amino, mono- or diloweralkylamino, methyl, ethyl, vinyl, ethynyl, propargyl, cyano, methoxy, ethoxy, trifluoromethyl, 2-hydroxyethyl, 2-hydroxypropyl, 3-hydroxypropyl, acetoxy, propanoyloxy, acetyl, propanoyl, hydroxyacetyl, 2-hydroxypropanoyloxy, 3-hydroxypropanoyl, acetamido, propanamido, hydroxyacetamido, 2-hydroxypropanamido, or 3-hydroxypropanamido (each of which must be situated in the beta configuration), or $J^1$ taken together with $A^1$, $A^2$, $A^3$ or a ring formed by $A^1$ together with $A^2$ completes a 3- to 7-membered substituted or unsubstituted carbocyclic or heterocyclic ring, the substituents of which contain not more than 15 carbon atoms, not more than 10 halogens, and not more than 8 heteroatoms selected from oxygen, nitrogen, silicon, phosphorus and sulfur; $J^2$ is selected from hydrogen, methyl, ethyl, hydroxymethyl, hydroxyethyl, vinyl, ethynyl, allyl, propargyl, n-propyl and isopropyl; and provided that if $P_1$ is a phorbol 12,13-di-n-alkanoyl moiety then $S_xE_1$ may not be chloromethyl, carboxy, carboxaldehyde, carboxaldehyde-2,4-dinitrophenylhydrazone, and provided that if $P_1$ is a phorbol 12,13-di-0-acetyl moiety then $S_xE_x$ may not be cyano or aldoxime.

$P_2$ is a radical of the formula:

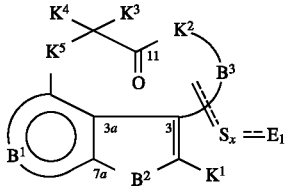

(P$_2$)

in the form of an individual isomer, an isomer mixture, a racemate or optical antipode, or a pharmaceutically acceptable salt thereof, wherein $B^1$ completes a 6-membered aromatic ring which may be carbocyclic or may optionally contain one or two nitrogen atoms at any of positions 5, 6 and 7 of the ring, wherein positions 5, 6 and/or 7 of $B^1$ are optionally and independently substituted on carbon by halogen and/or on carbon and/or nitrogen by straight chain or branched chain, cyclic or acyclic, saturated, unsaturated, and/or aromatic carbon- and/or heteroatom-containing groups which, taken together, contain not more than 40 carbon atoms, not more than 24 halogen atoms, and not more than 9 heteroatoms selected from oxygen, nitrogen, silicon, phosphorus and sulfur, the groups being optionally connected to one another and/or to $B^2$ to form 1–3 additional rings; $B^2$ is selected from oxygen, sulfur, sulfoxide, sulfone, monofluoromethylene, difluoromethylene, and a carbon or nitrogen atom optionally substituted by a straight chain or branched chain, cyclic or acyclic, saturated, unsaturated, and/or aromatic carbon- and/or heteroatom-containing groups having not more than 20 carbon atoms, not more than 24 halogen atoms, and not more than 6 heteroatoms selected from oxygen, nitrogen, silicon, phosphorus and sulfur, and $B^2$ may be linked to $B^1$ or $K^1$ to form an additional carbocyclic or heterocyclic ring; $B^3$ is a 2-carbon chain optionally substituted by halogen and/or one or more straight chain or branched chain, cyclic or acyclic, saturated, unsaturated, and/or carbon- and/or heteroatom-containing groups, which groups taken together but excluding $S_xE_1$, contain not more than 12 carbon atoms, not more than 6 halogen atoms, and not more than 6 heteroatoms selected from oxygen, nitrogen, and sulfur; provided that, including $S_xE_1$, the carbon atom of $B^3$ bonded to $K^2$ as defined below does not carry ---CH$_2$OH or ---CHCH$_3$OH; $K^1$ is hydrogen, halogen or a straight chain or branched chain, cyclic or acyclic, saturated, unsaturated, and/or aromatic carbon- and/or heteroatom-containing group containing not more than 30 carbon atoms, not more than 18 halogen atoms, and not more than 6 heteroatoms selected from oxygen, nitrogen, silicon, phosphorus and sulfur, and $K^1$ may be linked to $B^2$ or $B^3$ or to both $B^2$ and $B^3$ to form one or more additional carbocyclic and/or heterocyclic rings; $K^2$ is selected from oxygen, sulfur --NK$^6$-- or ---CK$^6$K$^7$-- wherein $K^6$ is hydrogen, hydroxy, methyl, ethyl, fluoro, n-propyl, allyl, or propargyl, and $K^7$ is hydrogen, methyl, ethyl, halogen, trifluoromethyl or cyano; $K^3$ and $K^4$ may be the same or may differ and may each be hydrogen, halogen or a straight chain or branched chain, cyclic or acyclic, saturated, unsaturated, and/or aromatic carbon- and/or heteroatom-containing group, such that $K^3$ and $K^4$ taken together contain not more than 18 carbon atoms, not more than 24 halogen atoms, and not more than 6 heteroatoms selected from oxygen, nitrogen, silicon, phosphorus and sulfur; $K^5$ is selected from oxygen, sulfur, sulfoxide, sulfone or $--NK^8--$, $--NOK^8--$ or $----CK^8K^9----$ wherein $K^8$ is hydrogen or a straight chain or branched chain, cyclic or acyclic, saturated, unsaturated, and/or aromatic carbon- and/or heteroatom-containing group containing not more than 30 carbon atoms, not more than 24 halogen atoms, and not more than 8 heteroatoms selected from oxygen, nitrogen, silicon, phosphorus and sulfur, and $K^9$ is hydrogen, methyl, ethyl, n-propyl, hydroxy, halogen, allyl, propargyl, cyano, or trifluoromethyl; provided that $P_2S_xE_1$ may not comprise (-)-1,10,14-O-trimethylindolactam V, and provided that if $B^1$ completes an unsubstituted or substituted carbocyclic aromatic ring, and $B^2$ is $---NH---$, $---N-(C_1-C_{12}$ linear or branched alkyl or alkanoyl)$---$, $---N-COOCH_2C_6H_5---$ or $---N-COOC(CH_3)_3---$, and $B^3$ is $---CH_2CH---$, and $K^1$ is hydrogen, and $K^2$ is $---NH---$, and $K^4$ is hydrogen, and $K^5$ is $---NH---$ or $---N(C_1-C_3\text{-alkyl})---$, then (i) if $S_xE_1$ is bonded to the carbon atom in $B^3$ that is adjacent to $K^2$, then $S_xE_1$ may not be $---COOMe$ or $---COOEt$; and (ii) if $S_x$ is a single bond directed to the carbon atom in $B^3$ that is adjacent to $K^2$, and $E_1$ is $---CH_2---R_e^e$, then $R_e^e$ is not any of hydrogen, chloro, bromo, $C_1-C_{12}$ saturated or unsaturated linear or branched alkoxy, $CH_3OCH_2O---$, $C_1-C_{12}$ linear or branched alkanoyloxy, bromoacetoxy, benzoyloxy, azidobenzoyloxy, $3,5-(CH_3)_2-C_6H_3COO---$, methanesulfonyloxy, toluenesulfonyloxy, dansyloxy, (tetrahydro-2H-pyran-2-yl)oxy, or $(C_1-C_6$ linear or branched alkyl$)_n$(phenyl)$_{3-n}$silyloxy, wherein n is 0–3.

$P_3$ is a radical of the formula:

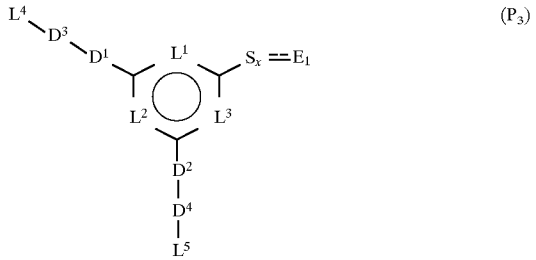

in the form of an individual isomer, an isomer mixture, a racemate or optical antipode, or a pharmaceutically acceptable salt thereof, wherein $L^1$, $L^2$ and $L^3$ are individually selected from nitrogen or substituted or unsubstituted carbon; $D^1$ and $D^2$ each may be a bond or a substituted or unsubstituted carbon atom; $D^1$ may be linked to $L^1$, $L^2$ or both $L^1$ and $L^2$ to form additional fused carbocyclic and/or heterocyclic substituted or unsubstituted rings; and $D^2$ may be linked to $L^2$, $L^3$ or both $L^2$ and $L^3$ to form additional fused carbocyclic and/or heterocyclic substituted or unsubstituted rings; $D^3$ and $D^4$ each are heteroatom-containing functional groups, the heteroatoms being selected from oxygen, nitrogen, silicon, phosphorus and sulfur; $D^3$ may be linked to $L^1$, $L^2$ or both $L^1$ and $L^2$ to form additional fused substituted or unsubstituted carbocyclic and/or heterocyclic rings; and $D^4$ may be linked to $L^2$, $L^3$ or both $L^2$ and $L^3$ to form additional fused substituted or unsubstituted carbocyclic and/or heterocyclic rings; provided that $D^1$ and $D^3$ taken together and $D^2$ and $D^4$ taken together both embody at least one oxygen, nitrogen, silicon, phosphorus or sulfur atom separated from the aromatic nucleus by zero or one intervening carbon atom; and $L^4$ and $L^5$ are straight chain or branched, cyclic or acyclic, saturated, unsaturated, and/or aromatic carbon- and/or heteroatom-containing groups which, taken together, contains about 2–40 carbon atoms, not more than 24 halogen atoms, and not more than 6 heteroatoms selected from oxygen, nitrogen, silicon, phosphorus and sulfur; provided that $S_xE_1$ may not be hydroxymethyl or 1-hydroxyethyl.

$P_4$ is a radical of the formula:

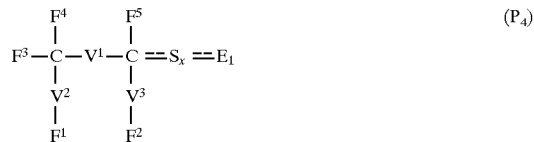

in the form of an individual isomer, an isomer mixture, a racemate or optical antipode, or a pharmaceutically acceptable salt thereof, wherein $V^1$ is a bond or is a carbon atom carrying substituents individually selected from hydrogen, methyl, and halogen; $V^2$ and $V^3$ are individually selected from oxygen, sulfur, sulfoxide, and $---NV^4---$ in which $V^4$ is hydrogen or a hydrocarbon radical containing not more than 30 carbon atoms; $F^1$ and $F^2$ independently are straight chain or branched, cyclic or acyclic, saturated, unsaturated, and/or aromatic carbon- and/or heteroatom-containing groups which, taken together, contain 10–60 carbon atoms, not more than 24 halogen atoms, and not more than 8 heteroatoms selected from oxygen, nitrogen, silicon, phosphorus and sulfur, and wherein $F^1$ and $F^2$ may optionally be linked to form a structure containing 1–3 rings; $F^3$ is hydrogen or a substituent selected from methyl, ethyl, trifluoromethyl, 2,2,2-trifluoroethyl, cyano, vinyl, ethynyl, allyl, and propargyl; $F^4$ and $F^5$ each may be hydrogen or may be hydrocarbon or halogenated hydrocarbon radicals which, taken together, contain not more than 40 carbon atoms, not more than 24 halogen atoms and not more than 8 heteroatoms selected from oxygen, nitrogen, silicon, phosphorus and sulfur, and wherein $F^4$ and $F^5$ may optionally be linked to form a structure containing 1–3 rings; provided that $V^4$, $F^1$, $F^2$, $F^4$ and $F^5$ taken together contain not more than 70 carbon atoms and provided that $S_xE_1$ may not be hydrogen, methyl, chloromethyl, hydroxymethyl, mercaptomethyl, unsubstituted carboxamido, 1-hydroxyethyl or alkanoyloxymethylene.

$P_5$ is a radical of the formula:

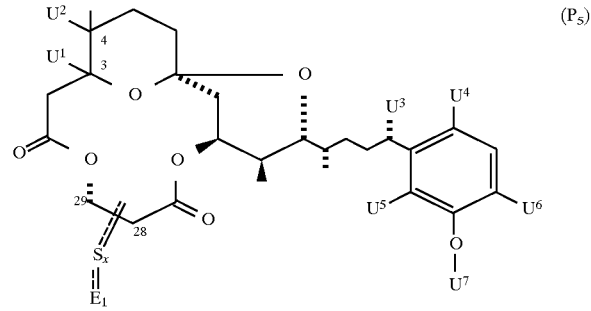

in the form of an individual isomer, an isomer mixture, a racemate or optical antipode, or a pharmaceutically acceptable salt thereof, wherein $U^1$ and $U^2$, independently, are selected from hydrogen, azide, halogen, hydroxy, $C_{1-7}$ alkoxy, $C_{1-7}$ alkenoxy, $C_{1-7}$ alkynoxy, thiol, $C_{1-7}$ alkanoyl, $C_{1-7}$ saturated or unsaturated alkyl, and cyano; or $U^1$ and $U^2$ taken together may be an oxygen atom forming an epoxy group or may be an additional bond forming an unsaturated linkage; $U^3$ is selected from hydrogen, halogen, $C_{1-12}$ alkyl, $C_1–C_{12}$ alkenyl, $C_1–C_{12}$ alkynyl, $C_1–C_{12}$ alkoxy, $C_1–C_{12}$ alkenoxy, $C_1–C_{12}$ alkynoxy, and aryl or $C_7–C_{12}$ aralkyl wherein the aryl group may be substituted by nitro, halogen, cyano, and/or diloweralkylamino groups; $U^4–U^6$, independently, are selected from hydrogen, halogen, cyano, nitro, amino, diloweralkylamino, $C_{1-7}$ saturated or unsaturated alkyl, hydroxy, $C_{1-7}$ saturated or unsaturated alkoxy, $C_{1-7}$ carboalkoxy, $C_{1-7}$ alkanoyloxy, and azide; and $U^7$ is selected from hydrbgen, $C_{1-7}$ saturated or unsaturated alkyl, and $C_{1-7}$ saturated or unsaturated alkanoyl; provided that if $S_xE_1$ is hydroxymethyl, 1-hydroxyethyl or acetoxymethylene, then $S_xE_1$ may not be bonded to $C_{29}$.

$P_6$ is a radical of the formula:

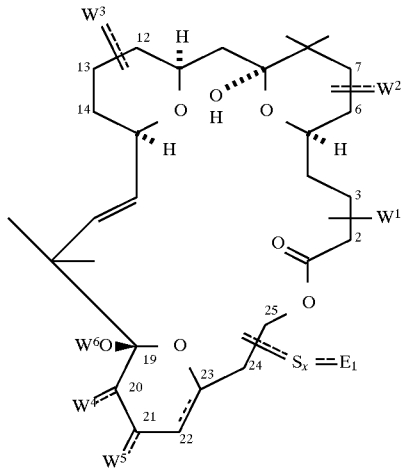 ($P_6$)

in the form of an individual isomer, an isomer mixture, a racemate or optical antipode, or a pharmaceutically acceptable salt thereof, wherein $W^1$ is selected from hydrogen, halogen, hydroxy, $C_{1-5}$ alkoxy, $C_{1-5}$ alkanoyloxy and cyano; $W^2$ is selected from oxo, hydrogen, hydroxy, cyano, $C_{1-7}$ alkyl, $C_{1-7}$ alkoxy, $C_{1-7}$ alkanoyloxy, and halogen; $W^3–W^5$ each may be hydrogen or a straight chain or branched chain, cyclic or acyclic, saturated, unsaturated, and/or aromatic carbon- and/or heteroatom-containing group, containing not more than 30 carbon atoms, not more than 24 halogen atoms, and not more than 8 heteroatoms selected from oxygen, nitrogen, and sulfur, and $W^4$ and $W^5$ taken together may form an additional carbocyclic or heterocyclic ring; $W^6$ is hydrogen or a straight chain or branched chain, cyclic or acyclic, saturated, unsaturated, and/or aromatic carbon- and/or heteroatom-containing group, containing not more than 15 carbon atoms, not more than 12 halogen atoms and not more than 5 heteroatoms selected from oxygen, nitrogen, and sulfur; and $W^6$, taken together with $W^4$ and $W^5$, may complete an additional carbocyclic or heterocyclic ring; provided that if $S_xE_1$ is hydroxymethyl or hydroxyethyl then $S_xE_1$ may not be bonded to $C_{25}$.

$S_x$ may represent any of a broad range of connecting chains of atoms, designated $S_B$, $S_1$, $S_2$, $S_3$, $S_4$, $S_5$ and $S_6$. Surprisingly, these chains may be hydrophobic in nature, with few if any polar or heteroatoms present, may be halogen-substituted, or may contain one or several polar atoms such as oxygen, nitrogen, silicon, phosphorus, arsenic, boron, selenium and/or sulfur in any of numerous chemical groupings, and the resultant compounds then display the protein kinase C-modulatory, non-toxic agonist, and/or antagonistic properties and utilities described in this invention.

$S_B$ is a single or double bond.

$S_1$ is a chain of atoms of the formula:

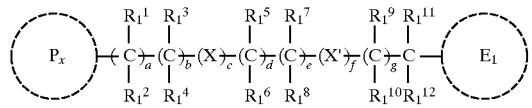

wherein a, b, d, e, and g may independently be from 0 to 3; c and f may, independently be 0 or 1; the sum of (a+b+c+d+e+f+g) is at least 1 but not more than 12; and if c and f are both 1, then the sum of (d+e) must be at least 1; $R_1^1$ through $R_1^{12}$ may be the same or different and each may be hydrogen, halogen or a saturated or singly or multiply unsaturated, straight or branched, acyclic substituent containing not more than 20 carbon atoms, not more than 16 halogen atoms, and not r sire than 6 heteroatoms selected from oxygen, nitrogen, and sulfur, such that for any substituent the oxygen, nitrogen, and sulfur atoms are situated in functional groups selected from hydroxy, amino, hydroxylamine, tertiary amine oxide, Schiff's base, hydrazine, thiol, nitro, nitroso, oxime, azide, ether, acetal, ketal, thioether, aldehyde, keto, hydrazone, carboxy, ester, amide, cyano, hydrazide, carbonate, carbamate, urea, isourea, carboxamidine, imidate, guanidine, thioester, thioamide, thiocarbonate, dithiocarbonate, thiocarbamate, dithiocarbamate, thiourea, isothiourea, thioimidate, nitroguanidine, cyanoguanidine, and xanthate; $R_1^1$ or $R_1^2$ may optionally be an additional bond completing an unsaturated linkage to $P_X$; one or two of the substituents $R_1^1$-$R_1^{12}$ may optionally comprise the same or different values of $G^1$, as defined below; $R_1^{11}$ or $R_1^{12}$ may optionally be an additional bond to $E_1$, thereby completing an unsaturated linkage; one of the substituents $R_1^1$-$R_1^{12}$ may be linked to either the atom in $P_x$ that carries the $S_1$ chain or to an atom in $P_x$ adjacent thereto, to form a saturated, unsaturated, or aromatic, carbocyclic or heterocyclic 4–8 membered ring optionally containing 1–4 identical or different ring hetero members selected from O, S, SO, $SO_2$, CO, =N-, and NH, the ring being optionally substituted on any carbon and/or NH members, by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy; X and X' are as defined below; provided that, for all substituents $R_1^1$ through $R_1^{12}$ and all constituents X and X', taken together, but excluding any atoms of $P_x$: the total of carbon atoms is 25 or less; the total of halogen atoms is 16 or less; the total of oxygen atoms is 6 or less; the total of nitrogen atoms is 4 or less; the total of sulfur atoms is 3 or less; the total of oxygen, nitrogen, silicon, phosphorus and sulfur atoms together is 8 or less; the total of --OH groups is 3 or less; the total of --$NH_2$ groups is 2 or less; the total of --SH groups is 2 or less; the total of --OH, --SH, and --$NH_2$ groups together is 4 or less.

$S_2$ is a chain of atoms of the formula:

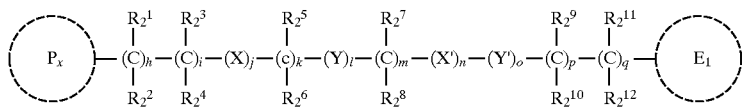

wherein h, i, k, m, p, and q may be independently be from 0 to 3; j and n may independently be 0 or 1; if j and n are both 1 and l is 0, then the sum of (k+m) must be at least 1; if n is 1 and o is 0, then the sum of (p+q) must be at least 1; the sum of (l+o) is 1–3; and the sum of (h+i+j+k+2l+m+n+2o+p+q) is at least 1 but not more than 12; $R_2^1$ through $R_2^{12}$ may be the same or different and each may be hydrogen, halogen or a saturated or singly or multiply unsaturated, straight or branched, acyclic substituent containing not more than 20 carbon atoms, not more than 16 halogen atoms, and not more than 6 heteroatoms selected from oxygen, nitrogen, and sulfur, such that for any substituent the oxygen, nitrogen, and sulfur atoms must be situated in functional groups selected from hydroxy, amino, hydroxylamine, tertiary amine oxide, Schiff's base, hydrazine, thiol, nitro, nitroso, oxime, azide, ether, acetal, ketal, thioether, aldehyde, keto, hydrazone, carboxy, ester, amide, cyano, hydrazide, carbonate, carbamate, urea, isourea, carboxamidine, imidate, guanidine, thioester, thioamide, thiocarbonate, dithiocarbonate, thiocarbamate, dithiocarbamate, thiourea, isothiourea, thioimidate, nitroguanidine, cyanoguanidine, and xanthate; $R_2^1$ or $R_2^2$ may optionally be an additional bond completing an unsaturated linkage to $P_x$; one or two of the substituents $R_2^1$-$R_2^{12}$ may optionally comprise the same or different values of $G^1$, as defined below; $R_2^{11}$ or $R_2^{12}$ may optionally be an additional bond to $E_1$, thereby completing an unsaturated linkage; one of the substituents $R_2^1$-$R_2^{12}$ may be linked to either the atom in $P_x$ that carries the $S_2$ chain or to an atom in $P_x$ adjacent thereto, to form a saturated, unsaturated, or aromatic, carbocyclic or heterocyclic 4–8 membered ring optionally containing 1–4 identical or different hetero ring members selected from O, S, SO, $SO_2$, CO, =N-, and NH, the ring being optionally substituted on any carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, COOH, $COOCH_3$, $COCH_3$, CH=O, acetoxy, amino, mono- or dialkylamino totalling 1–4 carbon atoms inclusive, acetamido, N-metlylacetamido, carboxamido, N-alkylated carboxamido containing 1–4 carbon atoms inclusive, hydroxyacetyl and hydroxyacetoxy; X, X', Y and Y' are as defined below; provided that, for all substituents $R_2^1$ through $R_2^{12}$ and all substituents embodied in X, X', Y, and Y' taken together, but excluding any atoms of $P_x$: the total of carbon atoms is 25 or less; the total of halogen atoms is 16 or less; the total of oxygen atoms is 6 or less; the total of nitrogen atoms is 4 or less; the total of sulfur atoms is 3 or less; the total of oxygen, nitrogen, silicon, phosphorus and sulfur atoms together is 8 or less; the total of --OH groups is 3 or less; the total of --$NH_2$ groups is 2 or less; the total of --SH groups is 2 or less; the total of --OH, --SH, and --$NH_2$ groups together is 4 or less.

$S_3$ is a chain of atoms of the formula:

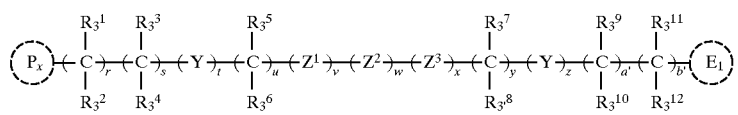

wherein r, s, u, y, a', and b' may independently be from 0 to 3; the sum of (t+z) is 0 or 1; the sum of (v+w+x) is 1; the sum of (y+z+a'+b') is at least 1; and the sum of (r+s+2t+u+2v+3w+4x+y+2z+a'+b') is at least 1 but not more than 12; $R_3^1$ through $R_3^{12}$ may be the same or different and each may be hydrogen, halogen or a saturated or singly or multiply unsaturated, straight or branched, acyclic substituent, containing not more than 20 carbon atoms, not more than 16 halogen atoms, and not more than 6 heteroatoms selected from oxygen, nitrogen, and sulfur, such that for any substituent the oxygen, nitrogen, and sulfur atoms must be situated in functional groups selected from hydroxy, amino, thiol, nitro, azide, ether, thioether, aldehyde, keto, carboxy, ester, amide, cyano, carbonate, carbamate, urea, isourea, carboxamidine, guanidine, thioester, thioamide, thiocarbonate, thiocarbamate, thiourea, nitroguanidine, cyanoguanidine, and xanthate; $R_3^1$ or $R_3^2$ may optionally be an additional bond completing an unsaturated linkage to $P_x$; one or two of the substituents $R_3^1$-$R_3^{12}$ may optionally comprise the same or different values of $G^1$, as defined below; $R_3^{11}$ or $R_3^{12}$ may optionally be an additional bond to $E_1$, thereby completing an unsaturated linkage; one of the substituents $R_3^1$-$R_3^{12}$ may be linked to either the atom in $P_x$ that carries the $S_3$ chain or to an atom in $P_x$ adjacent thereto, to form a saturated, unsaturated, or aromatic, carbocyclic 4–8 membered ring optionally containing 1–4 identical or different hetero ring members selected from O, S, SO, $SO_2$, CO, =N-, and NH, the ring being optionally substituted on any carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy; Y, Y', $Z^1$, $Z^2$, and $Z^3$ are as defined below; provided that, for all substituents $R_3^1$ through $R_3^{12}$ and all substituents embodied in Y, Y', $Z^1$, $Z^2$, and $Z^3$ taken together, but excluding any atoms of $P_x$: the total of carbon atoms is 25 or less; the total of halogen atoms is 16 or less; the total of oxygen atoms is 6 or less; the total of nitrogen atoms is 4 or less; the total of sulfur atoms is 3 or less; the total of oxygen, nitrogen, and sulfur atoms together is 8 or less; the total of --OH groups is 3 or less; the total of --NH$_2$ groups is 2 or less; the total of --SH groups is 2 or less; the total of --OH, --SH, and --NH$_2$ groups together is 4 or less.

S$_4$ is a chain of atoms defined by:

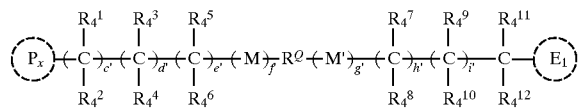

wherein c', d', e', h', and i' may independently be from 0 to 3; the sum of (f'+g') must be 1 or 2, f' and g' may independently be 0 or 1; and the sum of (c'+d'+e'+f'+g'+h'+i') is at least 1 but not more than 12; R$_4^1$ through R$_4^{12}$ may be the same or different and each may be hydrogen, halogen or a saturated or singly or multiply unsaturated, straight or branched, acyclic substituent containing not more than 20 carbon atoms, not more than 16 halogen atoms, and not more than 6 heteroatoms selected from oxygen, nitrogen, and sulfur, such that for any substituent the oxygen, nitrogen, and sulfur atoms must be situated in functional groups selected from hydroxy, amino, thiol, nitro, azide, ether, thioether, aldehyde, keto, carboxy, ester, amide, cyano, carbonate, carbamate, urea, isourea, carboxamidine, guanidine, thioester, thioamide, thiocarbonate, thiocarbamate, thiourea, nitroguanidine, cyanoguanidine, and xanthate; R$_4^1$ or R$_4^2$ may optionally be an additional bond completing an unsaturated linkage to the P$_x$ moiety; one or two of the substituents R$_4^1$-R$_4^{10}$ may optionally comprise the same or different values of G$^1$, as defined below; R$_4^{11}$ or R$_4^{12}$ may optionally be an additional bond to E$_1$, thereby completing an unsaturated linkage; one of the substituents R$_x^1$-R$_4^{12}$ may be linked to either the atom in P$_x$ that carries that S$_4$ chain or to an atom in P$_x$ adjacent thereto, to form a saturated, unsaturated, or aromatic, carbocyclic or heterocyclic 4–8 membered ring optionally containing 1–4 identical or different hetero ring members selected from O, S, SO, SO$_2$, CO, =N-, and NH, the ring being optionally substituted on any carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, CF$_3$, OCF$_3$, SH, SCH$_3$, SOCH$_3$, SCF$_3$, COOH, COOCH$_3$, COCH$_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy; M, M', and R$^Q$ are as defined below; provided that, for all substituents R$_4^1$ through R$_4^{12}$ and all constituents M, M' and R$^Q$ taken together, but excluding any atoms of the P$_x$ moiety: the total of carbon atoms is 25 or less; the total of halogen atoms is 16 or less; the total of oxygen atoms is 6 or less; the total of nitrogen atoms is 4 or less; the total of sulfur atoms is 3 or less; the total of oxygen, nitrogen, silicon, phosphorus and sulfur atoms together is 8 or less; the total of --OH groups is 3 or less; the total of --NH$_2$ groups is 2 or less; the total of --SH groups is 2 or less; the total of --OH, --SH, and --NH$_2$ groups together is 4 or less.

S$_5$ is a chain of atoms defined by:

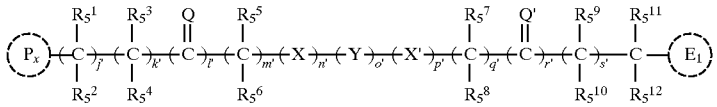

wherein j', k', m', q', and s' may independently be from 0 to 3; l' and r' may each be 0 or 1, but the sum of (l'+r') must be 1 or 2; n' and p' may each be 0 or 1, but the sum of (n'+p') must be 0 or 1; the value of o' may be 0–2; if the sum of (n'+p') is 1 and l' is 0, then q' must be at least 1; if the sum of (n'+p') is 1 and r' is 0, then m' must be at least 1; and the sum of (j'+k'+l'+m'+n'+o'+p'+q'+r'+s') is at least 1 but not more than 12; R$_5^1$ through R$_5^{12}$ may be the same or different and each may be hydrogen, halogen or a saturated or singly or multiply unsaturated, straight or branched, acyclic substituent containing not more than 20 carbon atoms, not more than 16 halogen atoms, and not more than 6 heteroatoms selected from oxygen, nitrogen, and sulfur, such that for any substituent the oxygen, and sulfur atoms must be situated in functional groups selected from hydroxy, amino, thiol, nitro, azide, ether, thioetlier, aldehyde, keto, carboxy, ester, amide, cyano, carbonate, carbamate, urea, isourea, carboxamidine, guanidine, thioester, thioamide, thiocarbonate, thiocarbamate, thiourea, nitroguanidine, cyanoguanidine, and xanthate; R$_5^1$ or R$_5^2$ may optionally comprise an additional bond completing an unsaturated linkage to P$_x$; one or two of the substituents R$_5^1$-R$_5^{12}$ may optionally comprise the same or different values of G$^1$, as defined below; R$_5^{11}$ or R$_5^{12}$ may optionally comprise an additional bond to E$_1$, thereby completing an unsaturated linkage; one of the substituents R$_5^1$-R$_5^{12}$ may be linked to either the atom in P$_x$ that carries the S$_5$ chain or to an atom in P$_x$ adjacent thereto, to form a saturated, unsaturated, or aromatic, carbocyclic 4–8 membered ring optionally containing 1–4 identical or different hetero ring members selected from O, S, SO, SO$_2$, CO, =N-, and NH, the ring being optionally substituted on any carbon and/or NH members by 1–8 identical or different substituents selected from halogen, hydroxy, metlioxy, ethoxy, methyl, ethyl, cyano, azide, nitro, hydroxymethyl, 1-hydroxyethyl, 2-hydroxy-2-propyl, CF$_3$, OCF$_3$, SH, SCH$_3$, SOCH$_3$, SCF$_3$, COOH, COOCH$_3$, COCH$_3$, CH=O, acetoxy, amino, mono- or dialkylamino totalling 1–4 carbon atoms inclusive, acetanido, N-methylacetamido, carboxamido, N-alkylated carboxamido containing 1–4 carbon atoms inclusive, hydroxyacetyl and hydroxyacetoxy; Q, Q', X, X', and Y are as defined below; provided that, for all substituents R$_5^1$ through R$_5^{12}$ and all constituents Q, Q', X, X', and Y taken together, but excluding any atoms of P$_x$: the total of carbon atoms is 25 or less; the total of halogen atoms is 16 or less; the total of oxygen atoms is 6 or less; the total of nithogen atoms is 4 or less; the total of sulfur atoms is 3 or less; the total of oxygen, nitrogen, silicon, phosphorus and sulfur atoms together is 8 or less; the total of —OH groups is 3 or less; the total of —NH$_2$ groups is 2 or less; the total of —SH groups is 2 or less; the total of —OH, —SH, and —NH$_2$, groups together is 4 or less.

S$_6$ is a chain of atoms defined by:

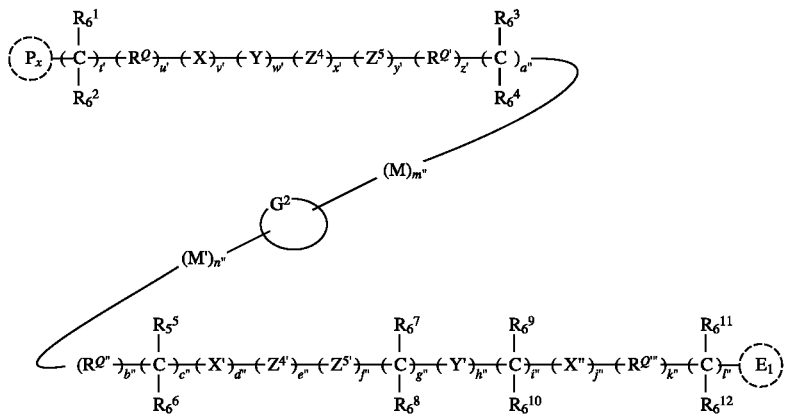

wherein u', v', w', x', y', z', and m" may each be 0 or 1; t' and a" may each independently be 0–6; the sum of (t'+u'+v'+2w'+x'+2y'+z'+a") must be 0–8; b", d", e", f", h", j", k" and n" may each independently be 0 or 1; c", g", i", and l" may each independently be 0–3; if d" and j" are both 1, then the sum of (g"+i") must be at least 1; if either j" or k" is 1, then l" must be at least 1; if b" is 1, then the sum of (c"+g"+h"+i"+l") must be at least 1; if d" is 1, then the sum of (g"+h"+i"+l") must be at least 1; and the sum of (t'+u'+v'+2w'+x'+2y'+z'+a"+b"+c"+d"+e"+2f"+g"+2h"+i"+j"+k"+l") must be 0–14; $R_6^1$ through $R_6^{12}$ may be the same or different and each may be hydrogen, halogen or a saturated or singly or multiply unsaturated, straight or branched, acyclic substituent containing not more than 20 carbon atoms, not more than 16 halogen atoms, and not more than 6 heteroatoms selected from oxygen, nitrogen, and sulfur, such that for any substituent the oxygen, nitrogen, and sulfur atoms must be situated in functional groups selected from hydroxy, amino, thiol, nitro, azide, ether, thioether, aldehyde, keto, carboxy, ester, amide, cyano, carbonate, carbamate, urea, isourea, carboxamidine, guanidine, thioester, thioamide, thiocarbamate, thiourea, nitroguanidine, cyanoguanidine, and xanthate; $R_6^1$ or $R_6^2$ may optionally be an additional bond completing an unsaturated linkage to $P_x$; if m" is zero, $R_6^3$ or $R_6^4$ may optionally comprise an additional bond to $G^2$ as defined below, thus completing an unsaturated linkage; if b" and n" are zero, $R_6^5$ or $R_6^6$ may optionally comprise an additional bond to $G^2$, thus completing an unsaturated linkage; one of the substituents $R_6^1$-$R_6^4$ and/or one of the substituents $R_6^5$ $R_6^{12}$ may optionally comprise the same or different values of $G^1$, as defined below; $R_6^{11}$ or $R_6^{12}$ may optionally comprise an additional bond to $E_1$, thereby completing an unsaturated linkage; one of the substituents $R_6^1$-$R_6^4$ may be linked to either the atom in $P_x$ that carries the $S_6$ chain or to an atom in $P_x$ adjacent thereto, to form a saturated, unsaturated, or aromatic, carbocyclic 4–8 membered ring optionally containing 1–4 hetero ring members selected from O, S, SO, $SO_2$, CO, =N-, and NH, the ring being optionally substituted on any carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 14 carbon atoms inclusive, acetamido, N-methylacetamido, carboxamido, N-alkylated carboxamido containing 1–4 carbon atoms inclusive, hydroxyacetyl and hydroxyacetoxy; M, M', $R^{Q'}$, $R^{Q''}$, $R^{Q'''}$, X, X', X", Y, Y', $Z^4$, $Z^{4'}$, $Z^5$ and $Z^{5'}$ are as defined below; provided that, for all substituents $R_6^1$ through $R_6^{12}$ and all constituents M, M', $R^Q$, $R^{Q'}$, $R^{Q''}$, $R^{Q'''}$, X', X", Y, Y', $Z^4$, $Z^{4'}$, $Z^5$ and $Z^{5'}$ and $G^2$ taken together, but excluding any atoms of $P_x$: the total of carbon atoms is 25 or less; the total of halogen atoms is 16 or less; the total of oxygen atoms is 6 or less; the total of nitrogen atoms is 4 or less; the total of sulfur atoms is 3 or less, the total of oxygen, nitrogen, silicon, phosphorus and sulfur atoms together is 8 or less; the total of —OH groups is 3 or less; the total of —$NH_2$ groups is 2 or less; the total of —SH groups is 2 or less; the total of —OH, —SH, and —$NH_2$ groups together is 4 or less.

X, X', X" may be the same or different and are selected from:

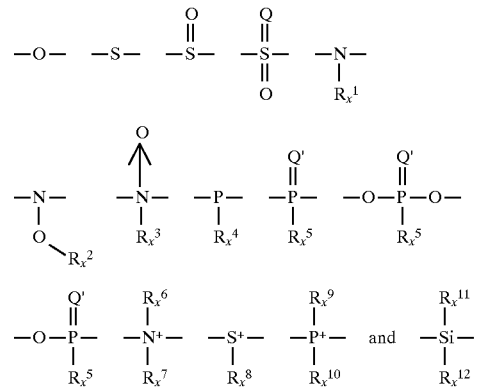

wherein $R_x^1$, $R_x^2$, $R_x^{11}$ and $R_x^{12}$ may independently be hydrogen; $R_x^1$ through $R_x^{12}$ may be the same or different and each may be a saturated or singly or multiply unsaturated, straight or branched, acyclic substituent containing 1–20 carbon atoms, not more than 16 halogen atoms, and not more than 6 heteroatoms selected from oxygen, nitrogen, and sulfur, such that for any substituent the oxygen atoms total 4 or less, the nitrogen atoms total 4 or less, and the sulfur atoms total 2 or less, the heteroatoms being situated in functional groups selected from hydroxy, amino, thiol, nitro, azide, ether, thioether, aldehyde, keto, carboxy, ester, amide, cyano, carbamate, urea, carboxamidine, guanidine, thioester, thioamide, thiocarbamate, thiourea, nitroguanidine, and cyanoguanidine; $R_x^4$, $R_x^5$, $R_x^{11}$ and $R_x^{12}$ may independently be hydroxy; Q and Q' are as defied below; $R_x^1$ may optionally represent an additional bond to $P_x$, thus completing an unsaturated linkage; any of the substituents $R_x^1$-$R_x^{12}$ may optionally comprise the same or different values of G¹, as defined below; and one of the substitents $R_X^1$-$R_X^{12}$ may be linked to either the atom in $P_x$ that carries the chain containing X, X', and/or X'' or to an atom in $P_x$ adjacent thereto, to form a saturated, unsaturated, or aromatic, heterocyclic 4–8 membered ring optionally containing 1–4 other identical or different hetero ring members selected from O, S, SO, $SO_2$, CO, =N-, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy.

Y and Y' may be the same or different and are selected from:

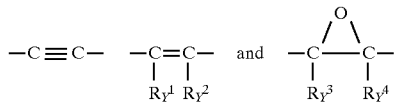

wherein $R_Y^1$ and $R_Y^2$, cis or trans relative to one another, may be the same or different and each may be hydrogen, halogen or may comprise a saturated or singly or multiply unsaturated, straight or branched acyclic substituent containing not more than 20 carbon atoms, not more than 16 halogen atoms, and not more than 6 heteroatoms selected from oxygen, nitrogen, and sulfur, such that for any substituent the oxygen atoms total 4 or less, the nitrogen atoms total 4 or less, and the sulfur atoms total 2 or less, the heteroatoms being situated in functional groups selected from hydroxy, amino, thiol, nitro, azide, ether, thioether, aldehyde, keto, carboxy, ester, amide, cyano, carbamate, urea, carboxamidine, guanidine, thioester, thioamide, thiocarbamate, thiourea, nitroguanidine, and cyanoguanidine; $R_Y^3$ and $R_Y^4$, cis or trans relative to one another, may be the same or different and each may be hydrogen or may be a saturated or singly or multiply unsaturated, straight or branched acyclic substituent containing not more than 20 carbon atoms, not more than 16 halogen atoms, and not more than 6 heteroatoms selected from oxygen, nitrogen, and sulfur, such that for any substituent the oxygen atoms total 4 or less, the nitrogen atoms total 4 or less, and the sulfur atoms total 2 or less, the heteroatoms being situated in functional groups selected from hydroxy, amino, thiol, nitro, azide, ether, thioether, aldehyde, keto, carboxy, ester, amide, cyano, carbamate, urea, carboxamidine, guanidine, thioester, thioamide, thiocarbamate, thiourea, nitroguanidine, and cyanoguanidine; any of the substituents $R_Y^1$-$R_Y^4$ may optionally comprise the same or different values of G¹, as defined below; and one of the substituents $R_Y^1$-$R_Y^4$ may be linked to either the atom in $P_x$ that carries the chain containing Y and/or Y' or to an atom in $P_x$ adjacent thereto, to form a saturated, unsaturated, or aromatic, carbocyclic 4–8 membered ring optionally containing 1–4 identical or different hetero ring members selected from O, S, SO, $SO_2$, CO, =N-, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy.

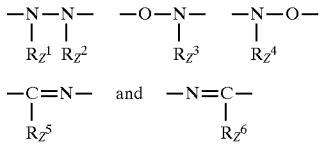

wherein $R_Z^1$ is hydrogen, a saturated or unsaturated substituent selected from $C_{1-6}$ alkyl (wherein the terminology "saturated or unsaturated substituent" when applied to alkyl, halogenated alkyl, and/or acyl is meant, here and throughout, to include alkenyl and alkynyl, their halogenated forms, and alkenoyl and alkynoyl), $C_{1-6}$ halogenated alkyl, $C_{1-6}$ acyl, $C_{1-6}$ halogenated acyl, $C_{2-6}$ monohydroxyacyl, and $C_{2-6}$ hydroxyalkyl, cyclohexyl, or phenyl or benzyl optionally substituted by methyl, ethyl, hydroxy, hydroxymethyl, thiol, carboxy, carboxymethyl, amino, methoxy, nitro, cyano, trifluoromethyl, and/or halogen, or, $R_Z^1$ may comprise an additional bond to $P_x$ thus completing an unsaturated linkage; $R_Z^2$ is hydrogen, a saturated or unsaturated substituent selected from $C_{1-6}$ alkyl, $C_{1-6}$ halogenated alkyl, $C_{1-6}$ acyl, $C_{1-6}$ halogenated acyl, $C_{2-6}$ monohydroxyacyl, and $C_{2-6}$ hydroxyalkyl, cyclohexyl, or phenyl or benzyl optionally substituted by methyl, ethyl, hydroxy, hydroxymethyl, thiol, carboxy, carboxymethyl, amino, methoxy, nitro, cyano, trifluoromethyl, and/or halogen; $R_Z^3$ independently may have the values specified above for $R_Z^2$; $R_Z^4$ independently may have the values specified above for $R_Z^1$; $R_Z^5$ may be hydrogen or a saturated or unsaturated substituent selected from $C_{1-6}$ alkyl, $C_{1-6}$ hydroxyalkyl, $C_{1-6}$ alkoxy, $C_{1-6}$ hydroxyalkoxy, $C_{1-6}$ halogenated alkyl, or phenyl or benzyl optionally substituted by methyl, ethyl, hydroxy, hydroxymethyl, thiol, carboxy, carboxymethyl, amino, methoxy, nitro, cyano, trifluoromethyl, and/or halogen; $R_Z^6$ independently may have the values specified above for $R_Z^5$; one of the substituents $R_Z^1$-$R_Z^6$ may be linked to either the atom in $P_x$ that carries the chain containing $Z^1$ or to an atom in $P_x$ adjacent thereto, to form a saturated, unsaturated, or aromatic, carbocyclic or heterocyclic 4–8 membered ring optionally containing 1–4 other identical or different hetero ring members selected from O, S, =N-, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy; provided that only one of the substituents $R_Z^1$-$R_Z^6$ may be substituted or unsubstituted phenyl or benzyl.

$Z^2$ is selected from:

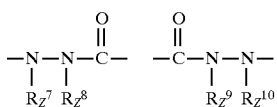

-continued

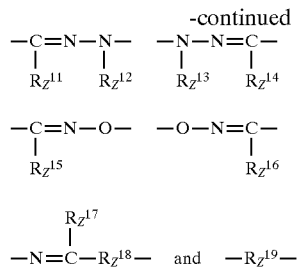

wherein $R_Z^7$ independenitly may have the values specified for $R_Z^1$; $R_Z^8$ is hydrogen, a saturated or unsaturated substituent selected from $C_{1-6}$ alkyl, $C_{1-6}$ halogenated alkyl, $C_{2-6}$ hydroxyalkyl in which the hydroxy group may be esterified to the acetyl or propionyl ester, and cyclohexyl, or phenyl or benzyl optionally substituted by methyl, ethyl, hydroxy, hydroxymethyl, thiol, carboxy, carboxymethyl, amino, methoxy, nitro, cyano, trifluoromethyl, and/or halogen; $R_Z^9$ independently may have the values specified above for $R_Z^8$; $R_Z^{10}$ independently may have the values specified above for $R_Z^7$; $R_Z^{11}$ may be hydrogen, a saturated or unsaturated substituent selected from $C_{1-6}$ alkyl, $C_{1-6}$ halogenated alkyl, and cyclolhexyl, or may be plienyl or benzyl, each optionally substituted by methyl, ethyl, hydroxy, hydroxymethyl, thiol, carboxy, carboxymethyl, amino, methoxy, nitro, cyano, trifluoromethyl, and/or halogen; $R_Z^{12}$ and $R_Z^{13}$ independently may have the values specified above for $R_Z^2$; $R_Z^{14}$-$R_Z^{16}$ independently may have the values specificd above for $R_Z^{11}$, $R_Z^{17}$ and $R_Z^{20}$ individually may be hydrogen or a substituent selected from $C_{1-4}$ alkyl; $C_{1-4}$ alkoxy; $C_{1-4}$ alkylthio; phenoxy or thiophenoxy optionally substituted by methyl, hydroxy, hydroxymethyl, thiol, carboxy, carboxymethyl, amino, methoxy, halogen, and/or nitro; or amino optionally mono- or disubstituted by $C_{1-4}$ alkyl or monosubstituLted by cyano, nitro, or phenyl optionally substituted by halogen, hydroxy, hydroxymethyl, thiol, carlboxy, carboxymethyl, amino, and/or nitro; $R_Z^{18}$ and $R_Z^{19}$ individually may be ---O---, ---S---, or ---$NR_Z^{21}$---, wherein $R_Z^{21}$ may be hydrogen, $C_{1-4}$ alkyl, 2-hydroxyethyl, 2-hydroxy-n-propyl, 2-acetoxyethyl, or 2-acetoxy-n-propyl; one of the substitutents $R_Z^7$-$R_Z^{17}$, $R_Z^{20}$ or $R_Z^{21}$ optionally may be linked to either the atom in $P_x$ that carries the chain containing $Z^2$ or to an atom in $P_x$ adjacent thereto, to form a saturated, unsaturated, or aromatic, carbocyclic or heterocyclic 4–8 membered ring optionally containing 1–4 other identical or different hetero ring members selected from O, S, =N-, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive hydroxyacetyl and hydroxyacetoxy; provided that only one of the substituents $R_Z^7$-$R_Z^{21}$ may comprise or carry a substituted or unsubstituted phenyl or benzyl.

$Z^3$ is selected from:

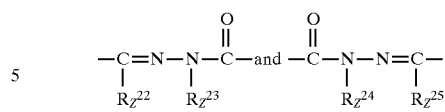

wherein $R_Z^{22}$ and $R_Z^{25}$ independently may have the values specified above for $R_Z^{11}$, $R_Z^{23}$ and $R_Z^{24}$ independently may have the values specified above for $R_Z^8$; $R_Z^{22}$ or $R_Z^{25}$ optionally may be linked to either the atom in $P_x$ that carries the chain containing $Z^3$ or to an atom in $P_x$ adjacent thereto, to form a saturated, unsaturated, or aromatic, carbocyclic or heterocyclic 4–8 membered ring optionally containing 1–4 other identical or different hetero ring members selected from O, S, =N-, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy; provided that at most one of the substituents $R_Z^{22}$-$R_Z^{25}$ may comprise or carry a substituted or unsubstituted phenyl or benzyl moiety.

$Z^4$ and $Z^{4'}$ independently may be:

wherein $R_Z^{26}$ may be hydrogen or may be a saturated or singly or multiply unsaturated, straight or branched, acyclic substituent containing 1–20 carbon atoms, not more than 16 halogen atoms, and not more than 6 heteroatoms selected from oxygen, nitrogen, and sulfur, in which substituent the oxygen atoms total 4 or less, the nitrogen atoms total 4 or less, and the sulfur atoms total 2 or less, the heteroatoms being situated in functional groups selected from hydroxy, amino, thiol, nitro, azide, ether, thioether, aldehyde, keto, carboxy, ester, amide, cyano, carbamate, urea, carboxamidine, guanidine, thioester, thioamide, thiocarbamate, thiourea, nitroguanidine, and cyanoguanidine; $R_Z^{26}$ may comprise $G^1$ as defined below; $R_Z^{26}$ may optionally comprise one additional bond either to $P_x$ or to $G^2$, thus completing an unsaturated linkage; $R_Z^{26}$ may be linked to either the atom in $P_x$ that carries the chain containing $Z^4$ or to an atom in $P_x$ adjacent thereto, to form a saturated, unsaturated, or aromatic, carbocyclic or heterocyclic 4–8 membered ring optionally containing 1–4 identical or different hetero ring members selected from O, S, SO, $SO_2$, CO, =N-, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy.

$Z^5$ and $Z^{5'}$ independently may be:

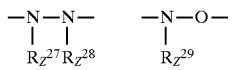

or

wherein $R_Z^{27}$ is hydrogen, a saturated or unsaturated substituent selected from $C_{1-6}$ alkyl, $C_{1-6}$ halogenated alkyl, $C_{1-6}$ acyl, $C_{1-6}$ halogenated acyl, $C_{2-6}$ monohydroxyacyl, and $C_{2-6}$ hydroxyalkyl, cyclolhexyl, or phenyl or benzyl optionally substituted by methyl, ethyl, hydroxy, hydroxymethyl, thiol, carboxy, carboxymethyl, amino, methoxy, nitro, cyano, trifluoromethyl, and/or halogen, or $R_Z^{27}$ may comprise an additional bond to $P_x$ or to $G^2$, thus completing an unsaturated linkage; $R_Z^{28}$ is hydrogen, a saturated or unsaturated substituent selected from $C_{1-6}$ alkyl, $C_{1-6}$ halogenated alkyl, $C_{1-6}$ acyl, $C_{1-6}$ halogenated acyl, $C_{2-6}$ monohydroxyacyl, and $C_{2-6}$ hydroxyalkyl, cyclohexyl, or phenyl or benzyl either of which may optionally be substituted by methyl, ethyl, hydroxy, hydroxymethyl, thiol, carboxy, carboxymethyl, amino, methoxy, nitro, cyano, trifluoromethyl, and/or halogen, or $R_Z^{28}$ may comprise an additional bond to $G^2$, thus completing an unsaturated linkage; $R_Z^{29}$ independently may have the values specified above for $R_Z^{27}$; and $R_Z^{30}$ independently may have the values specified above for $R_Z^1$.

M and M' independently may be:

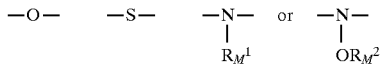

wherein $R_M^1$ and $R_M^2$ may be the same or different and each may be hydrogen or a saturated or singly or multiply unsaturated, straight or branched, acyclic substituent containing 1–20 carbon atoms, not more than 16 halogen atoms, and not more than 6 heteroatoms selected from oxygen, nitrogen, and sulfur, in which the oxygen atoms total 4 or less, the nitrogen atoms total 4 or less, and the sulfur atoms total 2 or less, the heteroatoms being situated in functional groups selected from hydroxy, amino, thiol, nitro, azide, ether, thioether, aldehyde, keto, carboxy, ester, amide, cayno, nitroguanidine, and cyanoguanidine; $R_M^1$ may optionally comprise an additional bond to $P_x$ group, thus completing an unsaturated linkage; $R_M^1$ or $R_M^2$ may optionally comprise the same or differetn values of $G^1$, as defined below; $R_M^1$ or $R_M^2$ may be linked to either the atom in $P_x$ that carries the chain Containing M and/or M' or to an atom in $P_x$ adjacent thereto, to form a saturated, unsaturated, or aromatic, carbocyclic 4–8 membered ring optionally containing, 1–4 identical or different hetero ring members selected from O, S, CO, =N-, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy.

Q-Q''' independently may be:

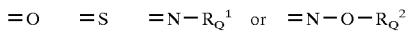

wherein $R_Q^1$ and $R_Q^2$ may be the same or different and each may be hydrogen or a saturated or singly or multiply unsaturated, straight or branched, acyclic substituent containing 1–20 carbon atoms, not more than 16 halogen atoms, and not more than 6 heteroatoms selected from oxygen, nitrogen, and sulfur, such that for any substituent the oxygen atoms total 4 or less, the nitrogen atoms total 4 or less, and the sulfur atoms total 2 or less, the heteroatoms being situated in functional groups selected from hydroxy, amino, thiol, nitro, ether, thioether, carboxy, ester, amide, cyano, nitroguanidine, and cyanoguanidine; $R_Q^1$ and/or $R_Q^2$ may optionally comprise the same or different values of $G^1$, as defined below; $R_Q^1$ may be linked to either the atom in $P_x$ that carries the chain containing Q and/or Q' or to an atom in $P_x$ adjacent thereto, to form a saturated, unsaturated, or aromatic, carbocyclic 4–8 membered ring optionally containing 1–4 identical or different hetero ring members selected from O, S, CO, =N-, and NH, the ring being optionally substituted on its carbon and/or NH members by 1-8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, CH=O, acetoxy amino mono- or dialkylamino totalling 1–4 carbon atoms inclusive, acecamido, N-methylacetamido, carboxamido, N-alkylated carboxamido containing 1–4 carbon atoms inclusive, hydroxyacetyl and hydroxyacetoxy. $R^Q$-$R^{Q'''}$ are independently selected from:

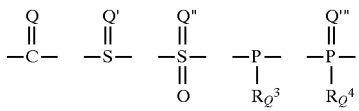

wherein $R_Q^3$ and $R_Q^4$ may be the same or different and each may be hydrogen, halogen or a saturated or singly or multiply unsaturated, straight or branched, acyclic substituent containing not more than 20 carbon atoms, not more than 16 halogen atoms, and not more than 6 heteroatoms selected from oxygen, nitrogen, and sulfur, such that for any substituent the oxygen, nitrogen, and sulfur atoms must be situated in functional groups selected from hydroxy, amino, thiol, nitro, azide, ether, thioether, aldehyde, keto, carboxy, ester, amide, cyano, carbonate, carbamate, urea, isourea, carboxamidine, guanidine, thioester, thioamide, thiocarbonate, thiocarbamate, thiourea, nitroguanidine, cyanoguanidine, and xanthate; $R_Q^3$ and/or $R_Q^4$ may optionally comprise the same or different values of $G^1$, as defined below; Q and Q' are as defined above; one of $R_Q^3$ and $R_Q^4$ may be linked to either the atom in $P_x$ bonded to the chain that carries $R^Q$ or to an atom in $P_x$ adjacent thereto, to form a saturated, unsaturated, or aromatic, carbocyclic or heterocyclic 4–8 membered ring optionally containing 1–4 identical or different hetero ring members selected from O, S, SO, $SO_2$, CO, =N-, and NH, the ring being optionally substituted on any carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methylacetamido, carboxamido, N-alkylated carboxamido containing 1–4 carbon atoms inclusive, hydroxyacetyl and hydroxyacetoxy.

G¹ comprises a group containing 1–3 fused or separate, saturated, unsaturated, or aromatic, carbocyclic or heterocyclic 4–8 membered rings, each ring optionally containing 1–4 identical or different hetero ring members selected from O, S, SO, $SO_2$, CO, =N-, and NH, each ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methyl acetamido, carboxamido, N-alkylated carboxamido containing 1–4 carbon atoms inclusive, hydroxyacetyl and hydroxyacetoxy, and wherein separate rings may be connected to one another and/or to the atom bearing G¹ by a bond or by an intervening substituted or unsubstituted, linear or branched, saturated or unsaturated chain containing not more than 8 carbon atoms, not more than 8 halogens, and not more than 4 heteroatoms selected from oxygen, nitrogen, silicon, phosphorus and sulfur; G² comprises 1–3 fused or separate, saturated, unsaturated and/or aromatic, carbocyclic or heterocyclic 4–8 membered rings, each ring optionally containing 1–4 identical or different hetero ring members selected from O, S, SO, $SO_2$, CO, =N-, and NH, each ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totalling 1–4 carbon atoms inclusive, acetamido, N-methyl acetamido, carboxamido, N-alkylated carboxamido containing 1–4 carbon atoms inclusive, hydroxyacetyl and hydroxyacetoxy, and wherein the first ring is singly or doubly bonded to both (i) $P_x$ or to a component atom of the $S_6$ chain connecting $P_x$ and G², and (ii) $E_1$ or to a component atom of the $S_6$ chain connecting $G_2$ and $E_1$, and wherein the optional second and third rings may be fused to $G_2$ and/or to one another or may be separate rings connected to one another and/or to the first ring by single or double bonds or by an intervening substituted or unsubstituted, linear or branched, saturated or unsaturated chain containing not more than 8 carbon atoms, not more than 8 halogens, and not more than 4 heteroatoms selected from oxygen, nitrogen, silicon, phosphorus and sulfur.

The capping group $E_o$ that terminates the connecting chain also may be selected from any of a surprisingly broad array of chemical groupings, and these chemical groupings can be composed of a far larger number of atoms than is found in the hydroxymethyl or 1-hydroxyethyl group. These chemical groupings may include, without limitation, hydrophobic entities such as alkyl, hydrogen, and halogenated alkyl, or may include, without limitation, quite hydrophilic moieties, such as hydroxy, thiol, carboxy and carboxy esters, amines, etc. It is well-known in the art that organic functional groups spanning a wide range of properties, from ionized and very hydrophilic to very hydrophobic, can be formed from multi-atom groupings of elements selected from carbon, hydrogen, halogen, oxygen, nitrogen, silicon, phosphorus, arsenic, boron and selenium. Indeed, for this invention the single restriction appears to be that $S_oE_o$ taken together should not be hydroxymethyl or 1-hydroxyethyl bonded in the usual position in the parent compounds, since such compounds correspond to the toxic parent natural products.

Thus, $E_o$ may be a moiety $E_1$, wherein $E_1$ is selected from =O, =S, =NH, =NOH, =N—$NH_2$, hydrogen, halogen, —OH, —SH, —$NH_2$, —NH—$NH_2$, —$N_3$, —CN, —NO, —$NO_2$, —NHOH, —$ONH_2$, or is selected from:

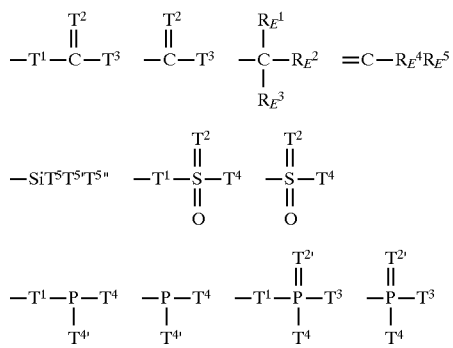

wherein T¹ is selected from —O—, —S—, and —NH—; T² is selected from =O, =S, and =N—$R_E^6$, in which $R_E^6$ may be hydrogen, hydroxy, cyano, or nitro; $T^{2'}$ is selected from =O and =S; T³, T⁴ and $T^{4'}$ are independently selected from —OH, —$NH_2$, —SH, —$N_3$, —NH—$NH_2$, and —NH—$OR_E^7$, in which $R_E^7$ may be hydrogen $C_{1-3}$, alkyl, or $C_{1-3}$ acyl; T³ may also be hydrogen or halogen; $T^5$-$T^{5''}$ are independently selected from hydrogen and hydroxy; $T^5$ may also be halogen; $R_E^1$ is selected from hydrogen, halogen, hydroxy, nitro, nitroso, cyano, azide, —$NH_2$, —NH—OH, —SH, —O—$NH_2$, —NH—$NH_2$, —T¹—C(=T²)—T³, —C(=T²)—T³, —$SiT^5T^{5'}T^{5''}$, —T¹—S(=O)(=T²)—T⁴, —S(=O)(=T²)—T⁴, —T¹—P(—T⁴)—T⁴, —P(—T⁴)—T⁴, —T¹—P(=$T^{2'}$)(—T³)—T⁴, and —P(=$T^{2'}$)(—T³)—T⁴; $R_E^2$ and $R_E^3$ are individually selected from hydrogen, —C(=T²)—T³, cyano, nitro, azide, halogen and a $C_1$-$C_{15}$ is straight or branched chain, saturated, unsaturated and/or aromatic-containing alkyl moiety optionally containing not more than 10 halogen atoms and not more than 4 heteroatoms selected from oxygen, nitrogen and sulfur.

If $R_E^1$ is cyano or —C(=T²)—T³, then $R_E^2$ or $R_E^3$ may optionally be selected from —$SiT^5T^{5'}T^{5''}$, —T¹—P(=$T^{2'}$)(—T³)—T⁴, and —P(=$T^{2'}$)(—T³)—T⁴; and $R_E^4$ and $R_E^5$ are individually selected from hydrogen, halogen, cyano, nitro, —C(=T²)—T³, —T¹—C(=T²)—T³, —$CR_E^1R_E^2R_E^3$, —$SiT^5T^{5'}T^{5''}$, —S(=O)(=T²)—T⁴, and —P(=$T^{2'}$)(—T³)—T⁴.

It will be appreciated that the many different permissible changes to the hydroxymethyl or 1-hydroxyethyl groups of the parent phorboids lead to diverse compounds with diverse biological properties, and different embodiments will be preferred for different utilities. For example, a preferred set of compounds for anti-viral activity in human cells is generated by replacing the hydroxymethyl or 1-hydroxyethyl groups of parent phorboids with the following moieties: (i) dihalomethyl, trihalomethyl, —CN, —CH=NOH, —CH=$NOCH_3$, —CHN(→O)$CH_3$, —C($CH_3$)=NOH, —CH=$CHR_a^a$, —C≡C-$R_a^a$, —$CH_2$C≡C-$R_a^a$, —Si($CH_3$)$_2$OH, —Si(OH)$_2CH_3$, —SiC$CH_3$)$_2$F, —Si($CH_3$)$_2R_a^a$, —$CH_2$Si($CH_3$)$_2R_a^a$, or =$CHR_a^a$, in which $R_a^a$ is hydrogen or $C_{1-12}$ linear or branched, saturated, unsaturated and/or aromatic hydrocarbon optionally substituted by not more than 16 halogens; or (ii) —$CH_2$—or —CH($CH_3$)—, to either of which is bonded —$N_3$, —CN, —Si($CH_3$)$_2$OH, —Si(OH)$_2CH_3$, —$SiCCH_3$)$_2$F, the o-, m- or p-isomer of —M—$C_6H_4CH_2$—T³, the o-, m- or p-isomer of —$C_6H_4CH_2$—T³, —$SCH_2CH_2CH_3$, —S($CH_2$)$_3CH_3$, —$SCH_2CH_2$OH, —S(=O)—$CH_2CH_2$OH, —S(CH$_2$)$_3$OH, —S(CH$_2$)$_4$OH, —SCH$_2$CH$_2$SH, —M—C(=T$^2$)—M'—R$_a^a$, —OCH$_2$C(=O)CH$_3$, —OCH$_2$C(=NOH)CH$_3$, the o-, m- or p-isomer of —M—C(=T$^2$)—M'—C$_6$H$_4$—T$^3$, the o-, m- or p-isomer of —M—C(=T$^2$)—M'—C$_6$H$_4$CH$_2$—T$^3$, or -imidazol-2-yl.

Within the group of compounds derived from indolactam-type phorboids by modification of the hydroxymethyl group of the parent indolactams, a particularly preferred set of replacements for the hydroxymethyl group comprises the following chemical moieties: —CH$_2$SCH$_2$CH$_2$OH, —CH$_2$O(C=O)NHCH$_3$ and —CH$_2$O(C=O)NHCH(CH$_3$) (1-naphthyl).

The compounds of this invention have been found to possess valuable pharmacological properties. They block inflammation, block proliferation of cancer cells, and induce production of thrombolytic activity in human and veterinary medicine. These effects can be demonstrated, for example, by use of standard mouse ear inflammation tests by established agonists such as PMA and the ionophore A23187, by the inhibition of proliferation of human cancer cells in culture by induction of differentiation, and by measurement of fibrinolytic activity in cultured cells.

These compounds also show selective effects as antagonists for protein kinase C in some cases, as noninflammatory agonists for protein kinase C in other cases, and as selective ligands for protein kinase C and/or for phorboid receptors.

Thus, these compounds can be used as agents for the abrogation of pathophysiological conditions and disease states in applications such as anti-inflammatory, anti-psoriatic, anti-cancer, anti-ulcer, anti-hypertensive, anti-asthma, anti-arthritic, anti-autoimmune, anti-nociceptive, anti-secretory, anti-parasitic, anti-amoebic, anti-HIV viral replication, and any other application in which pathological involvement of protein kinase C is found.

Furthermore, the non-toxic agonists among the compounds of this invention may be used to achieve desired physiological results such as interferon release, interleukin induction, tumor necrosis factor production, immune system stimulation and/or reconstitution, insulin secretion, insulinomimetic activity, acceleration of wound healing, improvement in central nervous system functions such as memory and learning and abrogation of the symptoms or progress of Alzheimer's disease, and any other application for which desirable actions of protein kinase C are found.

As receptor subtype- and/or protein kinase C subtype-selective ligands, the compounds of this invention also have very valuable application as experimental agents for research into the role of protein kinase C and/or phorboid receptors in important biological processes and in human and veterinary diseases. Thus, their value extends to their use as pharmacological tools for in vitro and in vivo research, in a manner similar to the important roles that selection agonists and antagonists have played in the studies of the mechanism of action of adrenergic, dopaminergic, opiate, benzodiazepine, cholinergic, and serotoninergic receptor systems, among others.

In addition, the compounds can be used in in vitro diagnostics (e.g., in an assay for protein kinase C). They are also useful as intermediates in the production of other drugs, e.g., as described in the present invention.

The compounds of this invention are generally administered to animals, including but not limited to fish, avians, and mammals including humans.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients and carriers, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcoholics, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., enzyme inhibitors, to reduce metabolic degradation. Such carriers do not include the following solvents used alone: dimethylsulfoxide, acetone, or methanol or ethanol of greater than 80% concentration in water.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilizates obtained, for example, for the preparation of products for injection.

For topical application, there are employed as nonsprayable forms, viscous to semi-solid or solid forms comprising a carrier compatible with topical application and having a dynamic viscosity compatible with topical application, preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The compounds of this invention, admixed with appropriate carriers, may also be delivered to subjects by means of an externally connected or internally implanted pumping device to give a controlled and/or sustained release of the therapeutic mixture, or by means of a patch of natural or synthetic fabric and/or polymer impregnated with the compounds in a suitable carrier and affixed to the skin to achieve transdermal release and absorption of the active compounds.

Generally, the compounds of this invention are dispensed in unit dosage form comprising 0.01 to 1000 mg in a pharmaceutically acceptable carrier per unit dosage. They are incorporated in topical formulations in concentrations of about 0.01 to 10 weight percent.

It will be appreciated that the actual preferred amounts of active compound in a specific case will vary according to the specific compound being utilized, the particular compositions formulated, the mode of application, and the particular sites and organism being treated. Dosages for a given host can be determined using conventional considerations, e.g., by customary comparison of the differential activities of the subject compounds and of a known agent, e.g., by means of an appropriate, conventional pharmacological protocol.

Starting materials for the synthesis of the compounds of this invention may be obtained from any of a wide variety of natural sources, as described in the literature for the diterpenes (E. Hecker and R. Schmidt, *Fortschritte D. Chemie Organischer Naturstoffe* 31 377–467 (1974) and F. J. Evans and C. J. Soper, *Lloydia* 41 193–233 (1978), and references cited therein), and indole alkaloids and aplysiatoxins (T. Sugimura, *Gann* 73 499–507 (1982), and references cited therein). Furthermore, the diterpene, indole alkaloid, diacylglycerol, and diaminobenzyl alcohol compounds are available by synthesis de novo (See Y. Endo et al, *Chem. Pharm. Bull.* 32 358–361 (1984), *Tetrahedron* 42, 5905–5924 (1986), and references cited there-in; P. A. Wender, Am. Chem. Soc. National Meeting, Chicago, Ill., 9 Sep. 1985, Abstract #7, and P. A. Wender et al. *Proc. Nat. Acad. Sci.* 83, 4214–4218, 1986).

Given starting phorboids containing hydroxymethyl or 1-hydroxyethyl groups, the means for modifying the hydroxymethyl or 1-hydroxyethyl group to produce the compounds of this invention will be obvious to workers with ordinary skill in synthetic organic chemistry. The hydroxymethyl or 1-hydroxyethyl groups may be modified once other regions of the molecule have been suitably protected, using certain favorable methodologies. Once the phorboid nucleus is protected, the hydroxymethyl/1-hydroxyethyl may for example be conveniently capped under very mild conditions by reaction with a substituted or unsubstituted alkyl, aryl, or aralkyl isocyanate in the presence of a catalyst such as dibutyltin dilaurate. The resulting compounds lack the toxic inflammatory activity of the phorboid from which they were derived, and have themselves anti-inflammatory utility.

Conversion of the hydroxy group to a halogen or pseudohalogen not only in itself provides active anti-inflammatory compounds, but also permits displacement of the resultant electrophile by a very wide range of nucleophiles. Persons with ordinary skill in the art of organic chemistry will recognize that such nucleophiles can include without limitation reagents having carbon, hydrogen, oxygen, nitrogen, sulfur, phosphorus, silicon, arsenic, boron and/or selenium atoms in their structures. Particular examples, without limitation, would be reaction with ammonia, methylamine, sodium cyanide, N-methyl-2-hydroxyethylamine, 1[H]-tetrazole, or with the sodium salt of 2-mercaptoethanol, 3-mercaptopropanol, or of 2-hydroxymethylphenol. Many variations may be executed, as described in standard textbooks of synthetic organic chemistry, such as J. Mar, *Advanced Organic Chemistry*, Third Edition, Wiley-Interscience New York, 1985.

For those phorboids wherein the hydroxy of the hydroxymethyl group is allylic, such as phorbol, ingenol, and resiniferonol esters, the replacement of the hydroxy by chloro or preferably by bromo or iodo yields compounds that can be conveniently reacted with activated zinc in the presence of an electrophile such as, without limitation, an aldehyde, ketone, epoxide, or oxetane; the resultant compounds have one or more methylenes inserted between the original hydroxy group and the methylene to which it was attached. An illustration of this would be the reaction of 20-deoxy-20-chlorophorbol 12-myristate 13-acetate with an excess of formaldehyde and an excess of zinc in the presence of tetrahydrofuran and saturated ammonium chloride solution with vigorous stirring for 24 hours. The resultant compound has the 6,7-double bond rearranged to the 6,20-position and bears a new hydroxymethyl group attached to position 7 instead of to position six as in the parent diterpene, and this compound, 12-beta-myristoyloxy 13-acetoxy-4,9-dihydroxy-7-hydroxymethyl-1,6(20)-tigliadien-3-one, has good anti-inflammatory activity. Similarly, replacement of the hydroxymethyl hydroxy by halogen in any suitably protected phorboid permits strong nucleophiles to be generated by use of metals or strong bases, and persons with ordinary skill in the art of organic chemistry will recognize that such nucleophiles can be contacted with a very diverse range of electrophilic reagents having carbon, hydrogen, oxygen, nitrogen, sulfur, phosphorus, silicon, arsenic, boron and/or selenium atoms in their structures to obtain hydroxymethyl-modified phorboids of widely varying structures.

Alternatively, the hydroxy group in question may be oxidized to an aldehyde or keto group and then reacted via Wittig chemistry to obtain chain-extended compounds terminated by many different capping groups. In particular, a phorbol 12,13-diester may be selectively protected at the 4 and 9 hydroxy groups using trimethylsilyl trifluoromethanesulfonate, followed by reaction with manganese dioxide to obtain a protected aldehyde. The latter compound may be successfully treated with strong Wittig reagents such as the lithium salt of 2-hydroxyethylidenetriphenylphosphorane, followed by deprotection with tetrabutylammonium fluoride to obtain the corresponding chain-extended, 20,21-didehydro-21,22-dihomophorbol diester.

The hydroxymethyl group of suitable phorboids may be oxidized to the carboxylic acid level by methods well-known in the art, and this carboxylic group may be activated for condensation reactions by any of a number of well-known methods, e.g. by conversion to an acyl halide or to an active ester such as the N-hydroxysuccinimide ester. The resultant activated carboxyl may then be easily converted to simple or multifunctional ester, amide, or thioester derivatives by reaction with alcohols, amines, or thiols respectively, alone or in the presence of condensation catalysts. For example, 4-carboxy-6-(N-decanoylamino)indole may be converted to its N-hydroxysuccinimide ester by reaction with one equivalent of dicyclohexylcarbodiimide and one equivalent of N-hydroxysuccinimide in acetonitrilel tetrahydrofuran/methylene chloride suspension. The product N-hydroxysuccinimide ester is purified and then reacted with 3-amino-1,2-propanediol in tetrahydrofuran to obtain 4-(N-2,3-dihydroxypropylcarboxamido)-6-(N-decanoylamino)indole.

The use of the methods of total synthesis as described in the literature cited above, with obvious adaptations, permits specific modifications of the parent structures in the diterpene, indolactam, diacylglycerol, and diaminobenzyl alcohol groups, by established techniques in the art of synthetic chemistry, to obtain modified parent structures embodying alterations at the hydroxymethyl or 1-hydroxyethyl groups and having anti-inflammatory activity.

To further illustrate the synthesis of the compounds of this invention, the modified indolactam, 1,2,4,5,6,8-hexahydro-5-methyl-2-(1-methylethyl)-3H—pyrrolo(4,3,2-gh)-1,4-benzodiazonin-3-one, may be prepared from N-BOC-4-nitrotryptophanol [Y. Endo et al., *Tetrahedron* 42, 5905–5924 (1986)] by the application of several routes obvious to workers with ordinary skill in synthetic chemistry. For example, preparation of N-BOC-4-nitrodeoxytryptophanol may be accomplished by reduction of the phenylselenium derivative with triphenyltinhydride [D. Clive et al., *Chemical Communications*, 41–42 (1978)] or by reduction of the mesylate derivative with lithium triethylborohydride [R. W. Holder and M. G. Matturro, *J. Org. Chem.*, 42. 2166–2168 (1977)] or by several other routes. From the deoxy derivative the synthesis could proceed in the manner described by Y. Endo et al., loc cit., for the hydroxy derivative. Specifically, the resulting substituted indolylvaline methyl ester is hydrolyzed and the resulting acid is converted to the N-succinimidyl ester. Upon cleavage of the BOC group under acidic conditions cyclization to the lactam occurs directly to provide all four stereoisomers, i.e., 2R,5R-, 2R,5S-, 2S,5S-, and 2S,5R-1,2,4,5,6,8-hexahydro-5-methyl-2-(1-methylethyl)-3H-pyrrolo (4,3,2-gh)-,4-benzodiazonin-3-one. These stereo-isomers may be obtained separately either by beginning the synthesis with optically active N-BOC-4-nitrotrytophanol or by separation from the mixture by chromatography on an enantioselective column packing [D. Armstrong, *Analytical Chem-.*, 59 84–91A (1987)]. Similarly, the further modified indolactam, 1-(1-oxobutyl)-1,2,4,5,6,8-hexahydro-5-methyl-3H-pyrrolo (4,3,2-gh)-1,4-benzodiazonin-3-one, may be prepared. Specifically, hydrogenation of N-BOC-4-nitrodeoxytrytophanol over palladium on carbon will provide N(2')-BOC-4-aminodeoxytrytophanol. Alkylation of this compound with methyl bromoacetate affords N-[3-(N-BOC-2-aminopropyl)-4-indolyl]-glycine methyl ester [Y. Endo, et al., *Chem. Pharm. Bull.* 30 3457–3460 (1982)]. Acylation of this material with butanoyl chloride in the presence of potassium carbonate or pyridine will provide N-butanoyl-N-[3-(N-BOC-2-aminopropyl)-4-indolyl] glycine methyl ester. This latter material may be converted to 1-(1-oxobutyl)-1,2,4,5,6,8-hexahydro-5-methy-1-3H-pyrrolo(4,3,2-gh)-1,4-benzodiazonin-3-one by application of the methods of Y. Endo, et al., loc cit. (1986). The enantiomers, 5R- and 5S-, may be obtained separately by beginning with optically active materials as described above or by separation at the final stage by chromatography also as described above.

This invention is illustrated further by the following examples.

EXAMPLE 1

20-Deoxy-20-(2-hydroxyethylthio)phorbol 12,13-Dibutyrate

One gram of sodium metal was dissolved in 50 ml methanol, and 0.044 ml of this solution was placed in a test tube. Then 2.63 grams distilled 2-mercaptoethanol was dissolved in 50 ml acetonitrile, and 0.044 ml of this solution was added to the test tube. Then 20 mg 20-deoxy-20-chlorophorbol 12,13-dibutyrate were dissolved in 0.25 ml acetonitrile in a capped, nitrogen-flushed test tube. This latter solution was then rapidly treated with the methoxide/mercaptoethanol solution. An immediate precipitate formed. After 7 minutes, the reaction was freed of solvent and treated with 1 ml water and 1 drop acetic acid. This residue was partitioned between water and ethyl acetate, followed by drying of the organic phase over sodium sulfate. Silica gel preparative liquid chromatography using hexane/ethyl acetate mixtures yielded 9.5 mg of 20-deoxy-20-(2-hydroxyethylthio)phorbol 12,13-dibutyrate, which could not be crystallized.

EXAMPLE 2

20-Deoxy-20-(2-hydroxyethylthio)phorbol 12-Butyrate

Further preparative liquid chromatography of the reaction mixture from Example 1 using hexane/ethyl acetate on silica gel yielded 5.7 mg 20-deoxy-20-(2-hydroxyethylthio) phorbol 12-butyrate, the latter being the more polar compound. This compound could not be crystallized.

EXAMPLE 3

20-Deoxy-20-(2-hydroxyethylthio)-phorbol 12-Myristate 13-Acetate

To 0.1 gram 20-deoxy-20-chlorophorbol 12-myristate 13-acetate in 1 ml acetonitrile was added 0.5 ml of a solution of 246 mg 2-mercaptoethanol and 436 5 mg 2,4,6-collidine in 10 ml acetonitrile, followed by 50 mg diisopropylethylamine in 0.2 ml acetonitrile and 0.1 ml t-butyl methyl ether. Ten minutes later the reaction was treated with 0.107 mmoles sodium methoxide and 0.225 mmoles 2-mercaptoethanol in 0.25 ml methanol. Five minutes later the proportion of sodium methoxide/mercaptoethanol was doubled. After 10 minutes the reaction was stopped by addition of 2 drops acetic acid and 0.5 ml water. The organics were extracted into ethyl acetate, washed once with water, and dried over sodium sulfate. After solvent removal, the crude residue was purified by preparative liquid chromatography on silica gel using hexane/ethyl acetate 60/40. The product was 87 mg 20-deoxy-20-(2-hydroxyethylthio) phorbol 12-myristate 13-acetate in high purity. The compound did not crystallize.

EXAMPLE 4

20-Deoxy-20-(2-hydroxyethylthio)phorbol 12-Myristate

Twenty-five mg of 20-deoxy-20-chlorophorbol 12-myristate 13-acetate was dissolved in 0.2 ml ethylene glycol and 0.2 ml acetonitrile. This solution was treated with 0.13 ml of a solution of 200 mg sodium metal in 20 ml ethylene glycol over a period of 40 minutes. The reaction was partitioned between water and ethyl acetate, and the separated organics were dried over sodium sulfate. After removal of the ethyl acetate, the crude 20-deoxy-20-chlorophorbol 12-myristate was dissolved in 0.8 ml acetonitrile and treated with 0.18 ml of a solution of 0.31 ml 2-mercaptoethanol, 0.5 ml acetonitrile, and 0.5 ml of 1% sodium in methanol. After 40 minutes, an additional 0.04 ml of 1% sodium in methanol was added. Ten minuted later the reaction was stopped with 1 drop of acetic acid. After removal of the solvents in a stream of nitrogen, the residue was partitioned between ethyl acetate and pH 8 potassium phosphate. The organics were dried over sodium sulfate and freed of solvent prior to preparative liquid chromatographic purification using silica gel and hexane/ethyl acetate 45/55. The product, 37 mg of 20-deoxy-20-(2-hydroxyethylthio) phorbol 12-myristate, could not be crystallized.

EXAMPLE 5

20-Deoxy-20-[(2-hydroxyethyl)methylamino] phorbol 12-Myristate 13-Acetate 25 mg 20-deoxy-20-chlorophorbol 12-myristate 13-acetate was dissolved in 0.4 ml acetonitrile. To this was added 0.1 ml of a solution of 29.6 mg 2-(methylamino)

ethanol in 1 ml acetonitrile. After 70 minutes and additional 0.1 ml of the same amine solution was added. After an additional 70 minutes, 0.2 ml more amine solution was added. After 6.6 hours of total reaction time, the reaction was diluted with 4 ml methylene chloride and subjected to preparative liquid chromatography on silica gel using methylene chloride/methanol 92/8 followed by repurification on silica gel using methylene chloride/methanol 96/4. The product, 20-deoxy-20-[(2-hydroxyethyl)methylamino] phorbol 12-myristate 13-acetate, 14 mg, could not be crystallized.

EXAMPLES 6, 7, AND 8

20-Deoxy-20-fluorophorbol 12,13-Bis(2,4-difluorophenylacetate), 12-beta, 13-Bis[(2',4'-difluorophenyl)acetoxy]-7-fluoro-9-hydroxy-1,4,6 (20)-tigliatrien-3-one and 12-beta, 13-Bis(2,4-difluorophenylacetoxy)4,9-dihydroxy-7-fluoro-1,6 (20)-tigliadin-3-one 100 mg of phorbol 12,13-bis(2,4-difluorophenylacetate) were dissolved in 1.5 ml methylene chloride and the solution was set at 0° C. Then 26.2 mg diethylaminosulfur trifluoride in 0.5 ml methylene chloride were added dropwise during 1 minute. After 40 minutes, 0.2 ml more diethylaminosulfur trifluoride was added. After 10 more minutes, the reaction was shaken with 2 ml pH 8 potassium phosphate buffer, after which the organics were separated and dried over sodium sulfate. The reaction was repeated twice more, and the combined reaction products were freed of solvent, taken up in 10 ml ethyl acetate, and sucked through a funnel containing a layer of silica at the bottom, a layer of sodium sulfate in the middle and sodium chloride at the top. After washing the funnel contents with 50 ml ethyl acetate the combined eluants were freed of solvent and repeatedly chromatographed on silica preparative liquid chromatography columns using hexane/ethyl acetate 85/15 solvent mixtures. The products were 20-deoxy-20-fluorophorbol 12,13-bis(2,4-difluorophenylacetate), 40 mg; 12-beta, 13-Bis[(2',4'-difluorophenyl)acetoxy]-7-fluoro-9-hydroxy-1,4,6(20)-tigliatrien-3-one 25 mg; and 12-beta,13-bis(2,4-difluorophenylacetoxy)-4,9-dihydroxy-7-fluoro-1,6(20)-tigliadin-3-one, 40 mg; none of which could be crystallized.

EXAMPLE 9

4-Carboxy-6-(N-decanoylamino)indole

Five hundred-fifteen mg of 4-methoxycarbonyl-6-(N-decanoylamino)indole [prepared by the method of Wender et al., *PNAS*, 83, 4214–4218 (1986)] was dissolved in 60 mL of tetrahydrofuran. This solution was treated with 3 mL of a 1N KOH solution in water and also with 5 mL of methanol. The mixture was heated at 80° C. for 32 h. During this period another 2.5 mL of 1N KOH was added in two portions. After cooling the mixture was concentrated in vacuo. The mixture was then diluted with water and acidified with concentrated hydrochloric acid. The mixture was then extracted with methylene chloride. The organic layers were dried over sodium sulfate and concentrated to afford 300 mg of 4-carboxy-6-(N-decanoylamino)indole (60% yield). mp 248°–50° C.

EXAMPLE 10

4-carboxy-6-(N-decanoylamino)indole N-Succinimidyl Ester

A suspension of 470 mg of 4-carboxy-6-(N-decanoylamino)indole and 427 mg of N-hydroxysuccinimide in 100 mL of acetonitrile, 10 mL of methylene chloride and 10 mL of tetrahydrofuran was prepared. This suspension was stirred vigorously by a magnetic stirring bar as a solution of 540 mg of dicyclohexylcarbodiimide in 20 mL of acetonitrile was slowly added over a period of 1 h. The mixture was stirred vigorously for 72 h. It was then concentrated in vacuo and diluted with ethyl acetate. The resulting mixture was filtered to remove the copious precipitate. The filtrate was washed with water, dried over sodium sulfate and concentrated. Treatment of the resulting mixture with hexane/ethyl acetate 50:50 followed by filtration afforded 600 mg of 4-carboxy-6-(N-decanoylamino)indole N-succinimidyl ester, mp 154°–5° C.

EXAMPLE 11

4-(N-2,3-dihydroxypropylcarboxamido)-6-(N-decanoylamino)indole

To a solution of 89 mg of 3-amino-1,2-propanediol in 20 mL of tetrahydrofuran was added 136 mg of 4-carboxy-6-(N-decanoylamino)indole N-succinimidyl ester. The solution was stirred for 48 h. After concentration in vacuo the mixture was purified by preparative liquid chromatography using silica gel and methylene chloride/methanol 92:8. The product, 135 mg of 4-(N-2,3-dihydroxypropylcarboxamido)-6-(N-decanoylamino)indole, was recrystallized from methanol/methylene chloride, mp 139°–41° C.

EXAMPLE 12

4-(N-2-Mercaptoethylcarboxamido)-6-(N-decanoylamino)indole and 4-(S-2-Aminoethylthiolcarboxy)-6-(N-decanoylamino) indole To a solution of 113 mg of triethylamine in 20 mL of tetrahydrofuran was added, first, 86 mg of 2-aminoethanethiol hydrochloride and, then, 139 mg of 4-carboxy-6-(N-decanoylamino)indole N-succinimidyl ester. The solution was stirred for 48 h and then concentrated in vacuo. Purification by liquid chromatography using silica gel and methylene chloride/methanol 96:4 afforded two products. The earlier eluting product, 23 mg of 4-(N-2-mercaptoethylcarboxamido)-6-(N-decanoylamino)indole, decomposed at 200°–5° C. The later eluting product, 22 mg of 4-(S-2-aminoethylthiolcarboxy)-6-(N-decanoylamino) indole, was recrystzallized from methanol, mp 192°–3° C.

EXAMPLE 13

4-(2-Hydroxymethylpiperidinocarbonyl)-6-(N-decanoylamino)indole

To a solution of 145 mg of 4-carboxy-6-(N-decylamino) indole N-hydroxysuccinimidyl ester in 20 mL of tetrahydrofuran was added 103 mg or piperidinemethanol. The solution was heated at reflux for 5 days, at which time another 100 mg of piperidinemethanol was added and heating continued for another day. The solution was then concentrated in vacuo and purified by liquid chromatography using silica gel and methylene chloride/isopropyl alcohol (93:7). In this manner 21 mg of 4-(2-hydroxymethylpiperidinocarbonyl)-6-(N-decanoylamino) indole was obtained, mp 126°–129° C.

EXAMPLE 14 phorbol 12-Myristate 13-Acetate 20-Methylcarbamate

One hundred milligrams of phorbol 12-myristate 13-acetate was dissolved in 1 ml tetrahydrofuran. To this solution was added 11.5 microliters of methyl isocyanate, followed immediately by 20 microliters of a 10% by weight solution of dibutyltin dilaurate in tetrahydrofuran. After three hours an additional 11.5 microliters of methyl isocyanate was added. Sixteen hours later 30 microliters of the reaction solution was applied to a silica gel TLC plate and developed with hexanes/ethyl acetate 46/54. The band at Rf=0.4 was scraped off and the product was eluted from the silica with acetone. Removal of the solvent in a stream of nitrogen gave 2.8 mg of phorbol 12-myristate 13-acetate 20-methylcarbamate as a glassy solid for spectroscopic analysis and bioassay.

EXAMPLE 15

12-beta-myristoyloxy-13-acetoxy4,9-dihydroxy-7-hydroxymethy1- 1,6(20)-tigliadien-3-one Ninety-eight mg of 20-deoxy-20-chlorophorbol 12-myristate 13-acetate was dissolved in 0.5 ml tetrahydrofuran. To this was added 0.15 ml saturated aqueous ammonium chloride, 0.15 ml 37% formalin solution, and 50 mg zinc dust (less than 325 mesh). The reaction was capped and shaken vigorously for 24 hours. At the end of this time the reaction was partitioned between pH8 phosphate buffer and ethyl acetate. The ethyl acetate phase was reduced to a volume of 2 ml under a stream of nitrogen and 0.125 ml was applied to a silica gel TLC plate and developed with hexanes/ethyl acetate 46/54. The band at Rf=0.45 was scraped off and the product was eluted from the silica powder with acetone. Removal of the acetone yielded 3.0 mg of 12-beta-myristoyloxy-13-acetoxy-4,9-dihydroxy-7-hydroxymethy-1-1,6(20)-tigliadien-3-one as a glassy solid for spectroscopic analysis and bioassay.

EXAMPLE 16

A stock solution of 300 pmoles of the standard inflammatory compound phorbol 12-myristate 13-acetate per 0.005 ml acetone was prepared. This solution was used to prepare four-fold dilutions of 20-deoxy-20-(2-hydroxyethylthio)phorbol 12-myristate 13-acetate, prepared as in Example 3, covering concentrations of the latter ranging from 4 to 64,000 pmoles per 0.005 ml. These solutions were used to demonstrate the anti-inflammatory activity of the latter compound by application of 0.005 ml to the insides of the right ears of mice, followed by the observation of ear inflammation/erythema during a 1–48 hour period. Inhibition of the phorbol 12-myristate 13-acetate induced inflammation was observed at the medium and higher concentrations of the inhibitor.

In a like manner, the anti-inflammatory activities of the following other compounds were demonstrated:
phorbol 12-myristate;
phorbol 12,13-diacetate;
20-deoxy-20-chlorophorbol 12-myristate 13-acetate;
20-deoxy-20-(2-hydroxyethylthio)phorbol 12,13-dibutyrate;
20-deoxy-20-(2-hydroxyethylthio)phorbol 12-myristate 13-acetate;
20-deoxy-20-[(2-hydroxyethyl)methylamino]phorbol 12-myristate 13-acetate;
20-deoxy-20-fluorophorbol 12,13-bis(2,4difluorophenylacetate);
12-beta, 13-Bis[(2',4'-difluorophenyl)acetoxy]-7-fluoro-9-hydroxy-1,4,6(20)-tigliatrien-3-one
12-beta, 13-bis(2,4-difluorophenylacetoxy)-4,9-dihydroxy-7-fluoro- 1,6(20)-tigliadien-3-one;
12-beta-myristoyloxy 13-acetoxy-4,9-dihydroxy-7-hydroxymethy1- 1,6(20)-tigliadien-3-one;
phorbol 12-myristate 13-acetate 20-methylcarbamate.

EXAMPLE 17

9-Deshydroxymethy1-9-carboxyindolactam V

A solution of 60 g of 4-nitrogramine [J. B. Hester, J. Org. Chem., 29, 1158 (1964)] and 54 g of ethyl nitroacetate in 1.2 L of chlorobenzene was heated at 100° C. for 1.5 h. After cooling the mixture was filtered, washed with cold methylene chloride and dried in vacuo to afford 58.9 g of ethyl 3-(4-nitro-2-indolyl)-2-nitropropionate as a yellow solid: mp 159°–160.5° C. Another 11 g may be recovered from the filtrate by dilution with hexane, preparative liquid chromatography [silica; methylene chloride/ethyl acetate (90:10)] and recrystallization from methanol. The structure was confirmed by NMR.

To a solution of 7.29 g of ethyl 3-(4-nitro-2-indolyl)-2-nitropropionate in 100 mL of tetrahydrofuran and 100 mL of ethanol was added 721 mg of 10% Pd on carbon. The resulting mixture was shaken in a Parr apparatus under about 50 psi hydrogen. After 70 min the mixture was filtered through celite and washed with ethanol. The filtrate was concentrated in vacuo. After purification by preparative liquid chromatography [silica; hexane/tetrahydrofuran (60:40)] 5.5 g of ethyl 3-(4-amino-2-indolyl)-2-nitropropionate was obtained as an off-white solid, mp 110°–112° C. The structure was confirmed by NMR.

To a mixture prepared by treatment of 8.6 g of the sodium salt of 3-methy1-2-oxobutanoic acid in 40 mL of dimethylformamide with 63 mmole of hydrogen chloride in 17 mL of dimethylformamide was added 10 g of ethyl 3-(4-amino-2-indolyl)-2-nitropropionate in 45 mL of N,N-dimethylformamide. After the resulting mixture had been cooled in an ice water bath, a solution of 6 g of sodium cyanoborohydride in 45 mL of N,N-dimethylformamide was added over 15 min. After the addition was complete, the mixture was allowed to warm to room temperature over a period of 30 min, at which time 200 mL of water was added and the mixture acidified with 2N hydrochloric acid. This solution was extracted with ethyl acetate. The organic layers were combined, washed with brine, dried over sodium sulfate and concentrated in vacuo and at a temperature only slightly above ambient to afford a crude mixture containing N-[4-[3-(2'-nitro-2'-ethoxycarbonyl)ethyl]indolyl]valine.

To a cooled solution of this crude residue and 7.2 g of N-hydroxysuccinimide in 250 mL of acetonitrile was added 15.5 g of dicyclohexylcarbodiimide in 35 mL of acetonitrile. After 40 min, 2.7 mL of glacial acetic acid was added. After another 20 min the mixture was filtered and washed with ethyl acetate. The filtrates were washed with water and brine, dried over sodium sulfate and concentrated in vacuo to afford crude N-[4-[3-(2'-nitro-2'-carboethoxy)ethyl]indolyl]valine N-succinimidyl ester. After combination with another batch and purification by preparative liquid chromatography [silica; hexane/tetrahydrofuran (57:43)], 24.4 g (91% yield) of the ester was obtained as a gum. The structure was confirmed by NMR and mass spectra.

To a solution of 3.75 g of N-[4[3-(2'-nitro-2'-ethoxycarbonyl)ethyl]indolyl]valine N-succinimidyl ester in 200 mL of methanol was added 11.5 mL of a slurry of Raney nickel. This mixture was shaken on a Parr apparatus under about 50 psi of hydrogen for 35 min. The supernatant was removed by decantation and concentrated in vacuo. Several such crude mixtures were combined and purified by preparative liquid chromatography [silica; hexane/ tetrahydrofuran (60:40)] to afford 3.23 g (31% yield) of N-desmethy-9-deshydroxymethyl-9-carboethoxyindolactam V, mp 195°–5° C. (decomp), and 2.13 g (20.5% yield) of N-desmethy-9-deshydroxymethy-9-ethoxycarbonyl-epi-indolactam V, mp 206°–8° C. (decomp). The structures of these compounds were confirmed by NMR and mass spectra and by conversion to the known indolactam V and epi-indolactam V respectively.

To a solution of 204 mg of N-desmethy-9-deshydroxymethy-9-ethoxycarbonylindolactam V in 20 mL of acetonitrile containing 1.5 mL of water was added 400 μL of 37% aqueous formaldehyde. After 20 min, 182 mg of sodium cyanoborohydride was added. After the mixture had stirred at room temperature for 3 hours, phosphate buffer (pH 2) was added. The mixture was then concentrated in vacuo before rediluting with water and extracting with ethyl acetate. The organic layer was dried over sodium sulfate, filtered and concentrated in vacuo. The resulting solid was purified by preparative liquid chromatography [silica; hexane/tetrahydrofuran, (60:40)] to afford 167 mg of 9-deshydroxymethy-9-ethoxycarbonyldolactam V. The structure was confirmed by NMR and mass spectra.

To a solution of 160 mg of 9-deshydroxymethy-9-ethoxycarbonylindolactam V in 23 mL of methanol was added 2.3 mL of 2N sodium hydroxide. After one hour 2N hydrochloric acid was added until the mixture was acidic whereupon it was concentrated to a small volume in vacuo. The residue was then diluted with water and extracted with ethyl acetate. The organic layer was dried over sodium sulfate, filtered and concentrated in vacuo to afford 137 mg of 9-deshydroxymethy-9-carboxyindolactam V as a white solid.

EXAMPLE 18

9-Deshydroxymethyl-9-carboxy-epi-indolactam V

A solution of 10 mg of N-desmethyl-9-deshydroxymethyl-9-ethoxycarbonyl-epi-indolactam V in 1 mL of acetonitrile containing 90 μL of water was added 20 μL of 37% aqueous formaldehyde. After 15 min 9 mg of sodium cyanoborohydride was added. After the mixture had stirred at room temperature for 3.5 hours, phosphate buffer (pH 2) was added and the mixture further diluted with water and extracted with ethyl acetate. The organic layer was dried over sodium sulfate, filtered and concentrated in vacuo to afford crude 9-deshydroxymethyl-9-ethoxycarbonyl-epi-indolactam V.

To a solution of 9-deshydroxymethyl-9-ethoxycarbonyl-epi-indolactam V in 2 mL of methanol was added 150 μL of 2N sodium hydroxide. After 50 min 2N hydrochloric acid was added until the mixture was acidic whereupon it was then diluted with water and extracted with ethyl acetate. The organic layer was dried over sodium sulfate, filtered and concentrated in vacuo to afford a residue of 9-deshydroxymethyl-9-carboxy-epi-indolactam V. The structure was confirmed by conversion to 9-deshydroxymethyl-9-meyhoxycarbonyl-epi-indolactam V by treatment with a solution of diazomethane in ether.

EXAMPLE 19

9-Deshydroxymethyl-9-carboxyindolactam V N-Succinimidyl Ester

To a solution of 137 mg of 9-deshydroxymethyl-9-carboxyindolactam V and 66 mg of N-hydroxysuccinimide in 7 mL of acetonitrile was added 119 mg of dicyclohexylcarbodiimide in 3 mL of acetonitrile. After about one hour the reaction mixture was filtered and then concentrated in vacuo. Purification by preparative liquid chromatography [silica; hexane/tetrahydrofuran, (70:30)] afforded 136 mg of 9-deshydroxymethyl-9-carboxyindolactam V N-succinimidyl ester.

EXAMPLE 20

9-Deshydroxymethyl-9-[N-(2',3'-dihydroxy)propyl] carboxamidoindolactam V

To 11 mg of 3-amino-1,2-propandiol and 1 mg of 4-dimethylaminopyridine was added 25 mg of 9-deshydroxymethyl-9-carboxyindolactam V N-succinimidyl ester in 250 μL of methylene chloride and 0.4 mL tetrahydrofuran. After 5 hr the mixture was concentrated in vacuo. After preparative liquid chromatography [silica; methylene chloride/isopropyl alcohol, (85:15); followed by ODS silica; acetonitrile/water, (33:67)], 10.5 mg of 9-deshydroxymethyl-9-[N-(2',3'-dihydroxy)propyl]-carboxamidoindolactam V and 3.4 mg of 9-deshydroxymethyl-9-[N-(2', 3'-dihydroxy)propyl] carboxamido-epi-indolactam V were obtained. The structures of these compounds were confirmed by mass spectra.

EXAMPLE 21

9-Deshydroxymethyl-9-(2',3'-dihydroxy) carboxypropylindolactam V

To 30 mg of glycerol and 1 mg of 4-dimethylaminopyridine was added 25 mg of 9-deshydroxymethyl-9-carboxyindolactam V N-succinimidyl ester in 250 μL of methylene chloride and 0.4 mL tetrahydrofuran. After 20 hr the mixture was concentrated in vacuo. After preparative liquid chromatography [silica; methylene chloride/isopropyl alcohol, (91:9); followed by ODS silica; acetonitrile/water, (36:64)] 13.3 mg of 9-deshydroxymethyl-9-(2',3'-dihydroxy) carboxypropylindolactam V and 1.2 mg of 9-deshydroxymethyl-9-(2',3'-dihydroxy)carboxypropyl-epi-indolactam V were obtained. The structures of these compounds were confirmed by mass spectra.

EXAMPLE 22

9-Deshydroxymethyl-9-[N-(2'-glucosyl)] carboxamidoindolactam V

To 29 mg of 2-glucosamine hydrochloride, 19 mg of triethylamine and 1 mg of 4-dimethylaminopyridine was added 25 mg of 9-deshydroxymethyl-9-carboxyindolactam V N-succinimidyl ester in 250 μL of methylene chloride and 0.4 mL tetrahydrofuran. After 7.5 hr the mixture was concentrated in vacuo. After preparative liquid chromatography [silica; methylene chloride/methanol, (80:20); followed by ODS silica; acetonitrile/water (1.2% triethylamine), (21:79) ], 12.4 mg of 9-deshydroxymethyl-9-[N-(2'-glucosyl)] carboxamidoindolactam V and 2.4 mg of 9-deshydroxymethyl-9-[N-(2'-glucosyl)]carboxamido-epi-indolactam V were obtained.

EXAMPLE 23

In a similar manner the following compounds are prepared:
9-deshydroxymethyl-9-[N-(2'-carboxy)ethyl] carboxamidoindolactam V;

9-deshydroxymethyl-9-[N-(2'-hydroxy)ethyl] carboxamidoindolactam V;
9-deshydroxymethyl-9-[S-(2'-hydroxy)ethyl] thiocarboxyinrdolactam V;
9-deshydroxymethyl-9-(2'-hydroxy) ethoxycarbonylindolactam V;
9-deshydroxymethyl-9-[N -(2',3'-dihydroxy)propyl] carboxamido -7-octylindolactam V;
9-deshydroxymethyl-9-[N-(2'-carboxy)ethyl]carboxamido-7-octylindolactam V;
9-deshydroxymethyl-9-[N-(2'-hydroxy)ethyl]carboxamido-7-octylindolactam V;
9-deshydroxymethyl-9-[S-(2'-hydroxy)ethyl]thiocarboxy-7-octylindolactam V;
9-deshydroxymethyl-9-(2'-hydroxy)ethoxycarbonyl-7-octylindolactam V;
9-deshydroxymethyl-9-[N-(2',3'-dihydroxy)propyl) carboxamido-7-octyl-epi-indolactam V;
9-deshydroxymethyl-9-[N-(2'-carboxy)ethyl]carboxamido-7-octyl-epi-indolactam V;
9-deshydroxymethyl-9-[N-(2'-hydroxy)ethyl]carboxamido-7-octyl-epi-indolactam V;
9-deshydroxymethyl-9-(2'-hydroxy)ethyl)thiocarbonyl-7-octyl-epi-indolactam V;
9-deshydroxymethyl-9-(2'-hydroxy)ethoxycarbonyl-octyl-epi-indolactam V;
9-deshydroxymethyl-9-[N-(2',3'-dihydroxy)propyl)] carboxamido-6,7-tetramethyleneindolactam V;
9-deshydroxymethyl-9-[N-(2'-carboxy)ethyl]carboxamido-6,7-tetramethyleneindolactam V;
9-deshydroxymethyl-9-[N-(2'-hydroxy)ethyl]carboxamido-6,7-tetramethyleneindolactam V;
9-deshydroxymethyl-9-[-(2'-hydroxy)ethyl]thiocarbonyl-6,7-tetramethyleneindolactam V;
9-deshydroxymethyl-9-(2'-hydroxy)ethoxycarbonyl-6,7-tetramethyleneindolactam V;
9-deshydroxymethyl-9-[N-(2',3'-dihydroxy)propyl)] carboxamido-7-octyl-12-desisopropyl-12-benzylindolactam V;
9-deshydroxymethyl-9-[N-(2'-carboxy)ethyl]carboxamido-7-octyl-12-desisopropyl-12-benzylindolactam V;
9-deshydroxymethyl-9-[N-(2'-hydroxy)ethyl]carboxamido-7-octyl-12-desisopropyl-12-benzylindolactam V;
9-deshydroxymethyl-9-[(2'-hydroxy)ethyl thiocarbonyl-7-octyl-12-desisopropyl-12-benzylindolactam V; and
9-deshydroxymethyl-9-(2'-hydroxy)ethoxycarbonyl-7-octyl-12-desisopropyl-12-benzylindolactam V.

EXAMPLE 24

14-O-[N-(S)-(1'-Naphthyl)ethyl]carbamoyl-7-octyl-(9S,12S)-indolactam V and 14-O-[N-(S)-(1'-Naphthyl)ethyl]carbamoyl-7-octyl-(9R,12R)-indolactam V To a solution of 139 mg of racemic 7-octylindolactam V [prepared as in K. Irie, et al., Agric. Biol. Chem., 50, 2679 (1986)] in 15 mL of anhydrous tetrahydrofuran was added 56 mg of dibutyltin dilaurate and 48 mg of 4-dimethylaminopyridine in 3 mL of tetrahydrofuran. To this solution was added 445 mg of (S)-1-(1-napthyl)ethyl isocyanate in two portions over a two day period. The mixture was then concentrated in vacuo and the residue partitioned between water and ethyl acetate. The organic layer was dried over sodium sulfate and concentrated in vacuo. After preparative liquid chromatography [silica; hexane/tetrahydrofuran (75:25)], 200 mg of a mixture of diastereomers was obtained. Repetitive chromatography of this mixture [wet silica; hexane/wet ethyl acetate (65:35)] afforded 87 mg of pure 14-O-[N-(S)-(1'-naphthyl)ethyl] carbamoyl-7-octyl-(9S,12S)-indolactam V and 96 mg of pure 14-O-[N-(S)-(1'-naphthyl)ethyl]carbamoyl-7-octyl-(9R,12R)-indolactam V. The structures of these compounds were confirmed by reduction to the known (–)-7-octylindolactam V and (+)-7-octylindolactam V respectively.

EXAMPLE 25

14-O-[N-(R)-(1'-Naaphthyl)ethyl]carbamoyl-(9S, 12S)-indolactam V and 14-O-[N-(R)-(1'-Naphthyl) ethyl]carbamoyl-(9R,12R)-indolactam V To a solution of 2.3 g of racemic indolactam V in 80 mL of anhydrous tetrahydrofuran with 569 mg of dibutyltin dilaurate and 560 mg of 4-dimethylaminopyridine was added 2.4 g of (R)-1-(1-napthyl)ethyl isocyanate. After stirring at room temperature for 24 hr, the mixture was concentrated in vacuo and the residue partitioned between water and ethyl acetate. The organic layer was dried over sodium sulfate and concentrated in vacuo. After preparative liquid chromatography [silica; hexane/tetrahydrofuran (55:45)], 3.65 g of a mixture of diastereomers was obtained. Repetitive chromatography of this mixture [wet silica; hexane/wet ethyl acetate (65:35)] afforded 1.92 g of 14O-[N-(R)-(1'-naphthyl)ethyl]carbamoyl-(9R,12R)-indolactam V and 1.77 g of 14-O-[N-(R)-(1'-naphthyl)ethyl]carbamoyl-(9S,12S)-indolactam V. The structures of these compounds were confirmed by NMR, by comparison with a sample of 14-O-[N-(R)-(1 '-naphthyl)ethyl]carbamoyl-(9S,12S)-indolactam V prepared from authentic (–)-indolactam V, and by reduction to the known (+)-indolactam V and (–)-indolactam V respectively.

EXAMPLE 26

14-O-(N-Methyl)carbamoyl-7-octyl-(9S,12S)-indolactam V

A solution of 3 mg of dibutyltin dilaurate and 2 mg of 4-dimethylaminopyridine in 0.5 mL of anhydrous tetrahydrofuran was added to 5 mg of (–)-7-octylindolactam V. Then 5 μL of methylisocyanate was added. After four hours at room temperature the mixture was concentrated under nitrogen and purified by preparative liquid chromatography [silica; hexane/tetrahydrofuran (70:30)] to afford 5 mg of 14-O-(N-methyl)carbamoyl-7-octyl-(9S,12S)-indolactam V.

EXAMPLE 27 rac-14-O-(N-Methyl)carbamoylindolactam V

To a solution of 105 mg of racemic indolactam V, 41 mg of 4-dimethylaminopyridine, and 57 mg of dibutyltin dilaurate in 18 mL of anhydrous tetrahydrofuran was added 150 μL of methylisocyanate in two portions over 1.5 hr. One hour after the final addition the mixture was concentrated in vacuo and the residue purified by recrystallization from tetrahydrofuran with hexane to afford 100 mg of rac-14-O-(N-methyl)carbamoylindolactam V, mp 184°–185° C.

EXAMPLE 28

In a similar manner the following compounds are prepared:
14-O-(N-ethyl)carbamoylindolactam V;
14-O-(N-methyl)thiocarbamoylindolactam V;
14-O-(N-benzyl)carbamoylindolactam V;

14-O-(N-ethyl)carbamoyl-7-octylindolactam V;
14-O-(N-methyl)thiocarbamoyl-7-octylindolactam V;
14-O-(N-benzyl)carbamoyl-7-octylindolactam V;
14-O-(N-methyl)carbamoyl-7-octyl-epi-indolactam V;
14-O-(N-ethyl)carbamoyl-7-octyl-epi-indolactam V;
14-O-(N-methyl)thiocarbamoyl-7-octyl-epi-indolactam V;
14-O-(N-benzyl)carbamoyl-7-octyl-epi-indolactam V;
14-O-(N-methyl)carbamoyl-6,7-tetramethyleneindolactam V;
14-O-(N-ethyl)carbamoyl-6,7-tetramethyleneindolactam V;
14-O-(N-methyl)thiocarbamoyl-6,7-tetramethyleneindolactam V;
14-O-(N-benzyl)carbamoyl-6,7-tetramethyleneindolactam V;
14-O-(N-methyl)carbamoyl-7-octyl-12-desisopropyl-12-benzylindolactam V;
14-O-(N-ethyl)carbamoyl-7-octyl-12-desisopropyl-12-benzylindolactam V;
14-O-(N-methyl)thiocarbamoyl-7-octyl-12-desisopropyl-12-benzylindolactam V;
14-O-(N-benzyl)carbamoyl-7-octyl-12-desisopropyl-12-benzylindolactam V;
14-O-(N-ethyl)carbamoylteleocidin B;
14-O-(N-methyl)thiocarbamoylteleocidin B; and
14-O-(N-benzyl)carbamoylteleocidin B.

EXAMPLE 29 rac-14-O-(N-Methyl)carbamoyl-1-N-(diphenylphosphoryl)indolactam V

To 12 mg of rac-14-O-(N-methyl)carbamoylindolactam V in 500 μL of anhydrous tetrahydrofuran was added approximately 2 mg of sodium hydride (50% dispersion in oil) followed by 30 μL of diphenyl chlorophosphate in two portions. After 2–3 hours, thin layer chromatographic analysis [silica; methylene chloride/methanol (95:5)] showed that the starting rac-14-O-(N-methyl)carbamoylindolactam V ($R_f$=0.36) had been converted to rac-14-O-(N-methyl)carbamoyl-1-N-diphenylphosphoryl-indolactam V with $R_f$=0.43.

EXAMPLE 30 rac-14-O-(N-Methyl)carbamoyl-1-N-(2-triphenylphosphonium)ethylindolactam V, Methanesulfonate salt To 16 mg of rac-14-O-(N-methyl)carbamoylindolactam V in 0.75 mL of N,N-dimethylformamide in an ice-water bath was added 8 mg of sodium hydride (60% dispersion in oil). After about 10 min this solution was added to 20 mg of 2-methanesulfonyloxyethyltriphenylphosphonium bromide (prepared from 2-hydroxyethyltriphenylphosphonium bromide). After 1 hr this mixture was concentrated in vacuo. The residue was partitioned between ethyl acetate and phosphate buffer (pH 2). The organic layer was dried over sodium sulfate and concentrated in vacuo. The crude mixture was taken up in methanol, treated with a small amount of methansulfonic acid in methanol and reconcentrated. Thin layer chromatographic analysis [silica; methylene chloride/methanol (90:10)] showed that the starting rac-14-O-(N-methyl)carbamoylindolactam V ($R_f$=0.63) had been converted to rac-14-O-(N-methyl)carbamoyl-1-N-(2-triphenylphosphonium)ethylindolactam V, methanesulfonate salt, with $R_f$=0.57.

EXAMPLE 31

In a similar manner the following compounds are prepared;

14-O-(N-methyl)thiocarbamoyl-1-N-(2-triphenylphosphonium)ethylindolactam V, methanesulfonate salt;
14-O-(N-benzyl)carbamoyl-1-N-(2-triphenylphosphonium)ethylindolactam V, methanesulfonate salt;
14-O-(N-methyl)thiocarbamoyl-1-N-(2-triphenylphosphonium)ethyl-epi-indolactam V, methanesulfonate salt;
14-O-(N-benzyl)carbamoyl-1-N-(2-triphenylphosphonium)ethyl-epi-indolactam V, methanesulfonate salt;
14-O-(N-methyl)carbamoyl-1-N-(2-triphenylphosphonium)ethyl-epi-indolactam V, methanesulfonate salt;
14-O-(N-methyl)carbamoyl-1-N-(2-triphenylphosphonium)ethyl-12-desisopropyl-12-benzylindolactam V, methanesulfonate salt;
14-O-(N-methyl)thiocarbamoyl-1-N-(2-triphenylphosphonium)ethyl-12-desisopropyl-12-benzylindolactam V, methanesulfonate salt; and
14-O-(N-benzyl)carbamoyl-1-N-(2-triphenylphosphonium)ethyl-12-desisopropyl-12-benzylindolactam V, methanesulfonate salt.

EXAMPLE 32 rac-14-O-(N-Methyl)carbamoyl-1-N-trimethylsilymethylindolactam V

To 16 mg of rac-14-O-(N-methyl)carbamoylindolactam V in 0.75 mL of N,N-dimethylformamide in an ice-water bath was added 8 mg of sodium hydride (60% dispersion in oil). After about 10 min, 20 μL of bromomethyltrimethylsilane was added. After 1 hr this mixture was concentrated in vacuo and the residue partitioned between ethyl acetate and phosphate buffer (pH 8). The organic layer was dried over sodium sulfate and concentrated in vacuo. Thin layer chromatographic analysis [silica; methylene chloride/methanol (95:5)] showed that the starting rac-14-O-(N-methyl)carbamoylindolactam V ($R_f$=0.36) had been converted to rac-14-O-(N-methyl)carbamoyl-1-N-trimethylsilylmethylindolactam V with $R_f$=0.59.

EXAMPLE 33

In a similar manner the following compounds are prepared:

14-O-(N-methyl)thiocarbamoyl-1-N-trimethylsilylmethylindolactam V;
14-O-(N-benzyl)carbamoyl-1-N-trimethylsilylmethylindolactam V;
14-O-(N-methyl)carbamoyl-1-N-trimethylsilylmethyl-epi-indolactam V;
14-O-(N-methyl)thiocarbamoyl-1-N-trimethylsilylmethyl-epi-indolactam V;
14-O-(N-benzyl)carbamoyl-1-N-trimethylsilylmethyl-epi-indolactam V;
14-O-(N-methyl)carbamoyl-1-N-trimethylsilylmethyl-12-desisopropyl-12-benzylindolactam V;
14-O-(N-methyl)thiocarbamoyl-1-N-trimethylsilylmethyl-12-desisopropyl-12-benzylindolactam V;
and 14-O-(N-benzyl)carbamoyl-1-N-trimethylsilylmethyl-12-desisopropyl-12-benzylindolactam V.

EXAMPLE 34

14-O-[(Diisopropylamino)methoxyl]phosphinyl-7-octyl-(9S,12S)-indolactam V

To 5 mg of (−)-7-octylindolactam V in 180 μL of anhydrous methylene chloride was added 15 μL of diisopropylethylamine followed by 7 μL of N,N-diisopropylmethylphosphoramidic chloride. After 0.5 hr, thin layer chromatographic analysis [silica; hexane/ethyl acetate (45:55)] showed that the starting (−)-7-octylindolactam V ($R_f$=0.17) had been converted to 14-O-[(diisopropylamino)methoxy]phosphinyl-7-octyl-(9S,12S)-indolactam V with $R_f$=0.72.

EXAMPLE 35

14-O-(Dimethyl)thiophosphoryl-7-octyl-(9S,12S)-indolactam V

To 5 mg of (−)-7-octylindolactam V in 200 μL of anhydrous methylene chloride and containing 5 μL of pyridine was added 14 μL of dimethyl chlorothiophosphate and approximately 10 mg of 4-dimethylaminopyridine. After 2 hr, thin layer chromatographic analysis [silica; methylene chloride/methanol (95:5)] showed that the starting (−)-7-octylindolactam V ($R_f$=0.32) had been converted to 14-O-(dimethyl)thiophosphoryl-7-octyl-(9S,12S)-indolactam V with $R_f$=0.36.

EXAMPLE 36

In a similar manner the following compounds are prepared:
14-O-(dimethyl)phosphorylindolactam V;
14-O-(tetramethyl)phosphorodiamidylindolactam V;
14-O-(diethyl)phosphonylindolactam V;
14-O-[bis(2',2',2'-trichloroethyl)]phosphorylindolactam V;
14-O-(dimethyl)thiophosphorylindolactam V;
14-O-(dimethyl)phosphoryl-7-octylindolactam V;
14-O-(tetramethyl)phosphorodiamidyl-7-octylindolactam V;
14-O-(diethyl)phosphonyl-7-octylindolactam V;
14-O-[bis(2',2',2'-trichloroethyl)]phosphoryl-7-octylindolactam V;
14-O-(dimethyl)thiophosphoryl-7-octyl-epi-indolactam V;
14-O-(dimethyl)phosphoryl-7-octyl-epi-indolactam V;
14-O-(tetramethyl)phosphorodiamidyl-7-octyl-epi-indolactam V;
14-O-(diethyl)phosphonyl-7-octyl-epi-indolactam V;
14-O-[bis(2',2',2'-trichloroethyl)]phosphoryl-7-octyl-epi-indolactam V;
14-O-(dimethyl)phosphoryl-6,7-tetramethyleneindolactam V;
14-O-(tetramethyl)phosphorodiamidyl-6,7-tetramethyleneindolactam V;
14-O-(diethyl)phosphonyl-6,7-tetramethyleneindolactam V;
14-O-[bis(2',2',2'-trichloroethyl)]phosphoryl-6,7-tetramethyleneindolactam V;
14-O-(dimethyl)thiophosphoryl-6,7-tetramethyleneindolactam V;
14-O-(dimethyl)thiophosphoryl-7-octyl-12-desisopropyl-12-benzylindolactam V;
14-O-(dimethyl)phosphoryl-7-octyl-12-desisopropyl-12-benzylindolactam V;
14-O-(tetramethyl)phosphorodiamidyl-7-octylindolactam V;
14-O-(diethyl)phosphonyl-7-octyl-12-desisopropyl-12-benzylindolactam V;
14-O-[bis(2',2',2'-trichloroethyl)]phosphoryl-7-octyl-12-desisopropyl-12-benzylindolactam V;
14-O-(dimethyl)phosphorylteleocidin B;
14-O-(tetramethyl)phosphorodiamidylteleocidin B;
14-O-(diethyl)phosphonylteleocidin B;
14-O-[bis(2',2',2'-trichloroethyl)]phosphorylteleocidin B; and
14-O-(dimethyl)thiophosphorylteleocidin B.

EXAMPLE 37

14-Deshydroxy-14-(3'-hydroxy)propylthio-7-octyl-(9S,12S)-indolactam V

To a solution of 6 mg of 3-mercapto-1-propanol in 150 μL of methanol containing 1.3 mg of sodium methoxide was added approximately 6 mg of 14-O-methanesulfonyl-7-octyl-(9S,12S)-indolactam V (prepared from (−)-7-octylindolactam V) in 300 μL of acetonitrile. After 20 hr this mixture was diluted with ethyl acetate and washed twice with phosphate buffers (pH 2 and pH 8). After drying over sodium sulfate, the organic layer was concentrated under a nitrogen stream. Thin layer chromatographic analysis [silica; methylene chloride/methanol (96:4)] showed that the starting 14-O-methanesulfonyl-7-octyl-(9S,12S)-indolactam V ($R_f$=0.67) had been converted to 14-deshydroxy-14-(3'-hydroxy)propylthio-7-octyl-(9S,12S)-indolactam V with $R_f$=0.22.

EXAMPLE 38

In a similar manner the following compounds are prepared:
14-deshydroxy-14-butylthio-7-octylindolactam V;
14-deshydroxy-14-(2'-hydroxy-1'-methyl)ethylthio-7-octylindolactam V;
14-deshydroxy-14-(2'-carboxy)ethylthio-7-octylindolactam V;
14-deshydroxy-14-(2'-amino)ethylthio-7-octylindolactam V;
14-deshydroxy-14(3'-hydroxymethyl)phenylthio-7-octylindolactam V;
14-deshydroxy-14propylthio-7-octyl-epi-indolactam V;
14-deshydroxy-14-(2'-hydroxy-1'-methyl)ethylthio-7-octyl-epi-indolactam V;
14-deshydroxy-14-(2'-carboxy)ethylthio-7-octyl-epi-indolactam V;
14-deshydroxy-14-(2'-amino)ethylthio-7-octyl-epi-indolactam V;
14-deshydroxy-14-(3'-hydroxymethyl)phenylthio-7-octyl-epi-indolactam V;
14-deshydroxy-14-(2'-hydroxy)ethylthio-7-octyl-epi-indolactam V;
14-deshydroxy-14-propylthio-6,7-tetramethyleneindolactam V;
14-deshydroxy-14-(2'-hydroxy-1'-methyl)ethylthio-6,7-tetramethyleneindolactam V;
14-deshydroxy-14-(2'-carboxy)ethylthio-6,7-tetramethyleneindolactam V;
14-deshydroxy-14-(2'-amino)ethylthio-6,7-tetramethyleneindolactam V;
14-deshydroxy-14-(3'-hydroxymethyl)phenylthio-6,7-tetramethyleneindolactam V;
14-deshydroxy-14-(2'-hydroxy)ethylthio-6,7-tetramethyleneindolactam V;
14-deshydroxy-14-propylthio-7-octyl-12-desisopropyl-12-benzylindolactam V;
14-deshydroxy-14-(2'-hydroxy-1'-methyl)ethylthio-7-octyl-12-desisopropyl-12-benzylindolactam V;

14-deshydroxy-14-(2'-carboxy)ethylthio-7-octyl-12-desisopropyl-12-benzylindolactam V;
14-deshydroxy-14-(2'-amino)ethylthio-7-octyl-12-desisopropyl-12-benzylindolactam V;
14-deshydroxy-14-(3'-hydroxymethyl)phenylthio-7-octyl-12-desisopropyl-12-benzylindolactam V; 14-deshydroxy-14-(2'-hydroxy)ethylthio-7-octyl-12-desisopropyl-12-benzylindolactam V;
14-deshydroxy-14-propylthioteleocidin B;
14-deshydroxy-14-(2'-hydroxy-1'-methyl)ethylthioteleocidin B;
14-deshydroxy-14-(2'-carboxy)ethylthioteleocidin B;
14-deshydroxy-14-(2'-amino)ethylthioteleocidin B;
14-deshydroxy-14-(3'-hydroxymethyl)phenylthioteleocidin B; and
14-deshydroxy-14-(2'-hydroxy)ethylthioteleocidin B.

EXAMPLE 39

14-Deshydroxy-14-(N-methanesulfonyl)amino-7-octyl-(9S,12S)-indolactam V

To a solution of 4 mg of methanesulfonamide in 150 µL of methanol containing 1.3 mg of sodium methoxide was added approximately 6 mg of 14-O-methanesulfonyl-7-octyl-(9S,12S)-indolactam V (prepared from (−)-7-octylindolactam V) in 300 µL of acetonitrile. After 26 hr this mixture was diluted with ethyl acetate and washed twice with phosphate buffers (pH 2 and pH 8). After drying over sodium sulfate, the organic layer was concentrated under a nitrogen stream. Thin layer chromatographic analysis [silica; hexane/ethyl acetate (45:55)] showed that the starting 14-O-methanesulfonyl-7-octyl-(9S,12S)-indolactam V ($R_f$=0.47) had been converted to 14-deshydroxy-14-N-methanesulfonyl) amino-7-octyl-(9S,12S)-indolactam V with $R_f$=0.38.

EXAMPLE 40

14-Deshydroxy-14-trimethylphosphonium-7-octyl-(9S,12S)-indolactam V, Methanesulfonate salt To a solution of approximately 6 mg of 14-O-methanesulfonyl-7-octyl-(9S,12S)-indolactam V (prepared from (−)-7-octylindolactam V) in 300 µL of acetonitrile was added 30 µL of 1M trimethylphosphine in toluene. After 26 hr this mixture was concentrated under a nitrogen stream. Thin layer chromatographic analysis [silica; methylene chloride/methanol, (95:5)] showed that the starting 14-O-methanesulfonyl-7-octyl-(9S,12S)-indolactam V ($R_f$=0.63) had been converted to 14-deshydroxy-14-trimethylphosphonium-7-octyl-(9S,12S)-indolactam V, methanesulfonate salt, with $R_f$=0.07.

EXAMPLE 41

14-Deshydroxy-14-triphenylphosphonium-7-octyl-(9S,12S)-indolactam V, Iodide salt To a solution of approximately 5 mg of 14-deshydroxy-14-iodo-7-octyl-(9S,12S)-indolactam V (prepared from 14-O-methanesulfonyl-7-octyl-(9S,12S)-indolactam V) in 1 mL of tetrahydrofuran was added 6 mg of triphenyphosphine. After 2.5 hr this mixture was concentrated under a nitrogen stream. Thin layer chromatographic analysis [silica; hexane/ethyl acetate, (45:55)] showed that the starting 14-deshydroxy-14-iodo-7-octyl-(9S,12S)-indolactam V ($R_f$=0.37) had been converted to 14-deshydroxy-14-triphenylphosphonium-7-octyl-(9S,12S)-indolactam V, iodide salt, with $R_f$=0.88.

EXAMPLE 42

In a similar manner the following compounds are prepared:
14-deshydroxy-14-tributylphosphonium-7-octylindolactam V, iodide salt;
14-deshydroxy-14-triethylphosphonium-7-octylindolactam V, iodide salt;
14-deshydroxy-14-methyldiphenylphosphonium-7-octylindolactam V, iodide salt;
14-deshydroxy-14-trimethylphosphonium-7-octyl-epi-indolactam V, iodide salt;
14-deshydroxy-14-tributylphosphonium-7-octyl-epi-indolactam V, iodide salt;
14-deshydroxy-14-triethylphosphonium-7-octyl-epi-indolactam V, iodide salt;
14-deshydroxy-14-methyldiphenylphosphonium-7-octyl-epi-indolactam V, iodide salt;
14-deshydroxy-14-trimethylphosphonium-6,7-tetramethyleneindolactam V, iodide salt;
14-deshydroxy-14-tributylphosphonium-6,7-tetramethyleneindolactam V, iodide salt;
14-deshydroxy-14-triethylphosphonium-6,7-tetramethyleneindolactam V, iodide salt;
14-deshydroxy-14-methyldiphenylphosphonium-6,7-tetramethyleneindolactam V, iodide salt;
14-deshydroxy-14-tributylphosphonium-7-octyl-12-desisopropyl-12-benzylindolactam V, iodide salt;
14-deshydroxy-14-triethylphosphonium-7-octyl-12-desisopropyl-12-benzylindolactam V, iodide salt;
14-deshydroxy-14-methyldiphenylphosphonium-7-octyl-12-desisopropyl-12-benzylindolactam V, iodide salt;
14-deshydroxy-14-trimethylphosphonium-7-octyl-12-desisopropyl-12-benzylindolactam V, iodide salt;
14-deshydroxy-14-tributylphosphoniumteleocidin B, iodide salt;
14-deshydroxy-14-triethylphosphoniumteleocidin B, iodide salt;
14-deshydroxy-14-methyldiphenylphosphoniumteleocidin B, iodide salt; and
14-deshydroxy-14-trimethylphosphoniumteleocidin B, iodide salt.

EXAMPLE 43

14-Deshydroxy-14-trimethylsilyl-7-octyl-(9S,12S)-indolactam V

To a mixture of 10 mg of powdered zinc and 10 µL of trimethylchlorosilane in 300 µL of anhydrous tetrahydrofuran was added approximately 5 mg of 14-deshydroxy-14-iodo-7-octyl-(9S,12S)-indolactam V (prepared from 14-O-methanesulfonyl-7-octyl-(9S,12S)-indolactam V) in 500 µL of tetrahydrofuran. After 2.5 hr, thin layer chromatographic analysis [silica; hexane/ethyl acetate, (45:55)] showed that the starting 14-deshydroxy-14-iodo-7-octyl-(9S,12S)-indolactam V ($R_f$=0.37) had been largely converted to 14-deshydroxy-14-trimethylsilyl-7-octyl-(9S,12S)-indolactam V with $R_f$=0.49.

EXAMPLE 44

In a similar manner the following compounds are prepared:
14-deshydroxy-14-trimethylsilyl-7-octyl-epi-indolactam V;
14-deshydroxy-14-trimethylsilyl-7-octyl-12-desisopropyl-12-benzylindolactam V;

14-deshydroxy-14-trimethylsilyl-6,7-tetramethyleneindolactam V; and
14-deshydroxy-14-trimethylsilylteleocidin B.

EXAMPLE 45

Demonstration of Anti-HIV Activity of 14-O-[N-(S)-(1'-Naphthyl)ethyl]carbamoyl-7-octyl-(9S,12S)-indolactam V Human peripheral blood lymphocytes were isolated from the buffy coat fractions of blood obtained from normal human donors. The lymphocytes were then stimulated with 5 μg/ml of phytohemagglutinin for 48 hours. Prior to infection with HIV, the lymphocytes were washed and resuspended in mitogen-free medium. On day 0 the cells were infected with HIV and were cultured for four days in the presence or absence of 10 μM 14-O-[N-(S)-(1'-naphthyl)ethyl]carbamoyl-7-octyl-(9R,12R)-indolactam V. On day 4 the supernatant levels of total viral RNA and viral core protein p24 were measured at each drug concentration using standard techniques to determine the percent inhibition of viral RNA and p24 protein production in drug-treated versus untreated cell cultures. At four days the percent inhibition values were less than 100% for both RNA and p24. Under identical testing conditions the standard human clinical anti-HIV drug azidothymidine gave 100% inhibition of RNA and p24 production at 100 nM and showed 50% inhibition for these two measures at about 3–5 nM.

EXAMPLE 46

In a similar manner the anti-HIV activity of the following indolactam-class of phorboid compounds was demonstrated; data giving percent inhibition of viral RNA production at selected concentrations appear in parentheses:

i) rac-14-O-(N-methyl)carbamoylindolactam V (52% inhibition at 10 μM);

ii) rac-14-O-(N-methyl)carbamoyl-1-N-(2-triphenylphosphonium)-ethylindolactam V, methanesulfonate salt (82%o inhibition at 10 μM);

iii) 14-O-(N-methyl)carbamoyl-7-octyl-(9S,12S)-indolactam V (87% inhibition at 10 μM);

iv) 9-deshydroxymethyl-9-[N-(2'-glucosyl)]carboxamidoindolactam V (35% inhibition at 10 μM);

v) 9-deshydroxymethyl-9-[N-(2',3'dihydroxypropyl)]-carboxamidoindolactam V (22% inhibition at 10 μM);

vi) 9-deshydroxymethyl-9-ethoxycarbonylindolactam V (47% inhibition at 10 μM);

vii) 1-N-hydroxymethyl-9-deshydroxymethyl-9-ethoxycarbonylindolactam. V (31% inhibition at 10 μM);

viii) 9-deshydroxymethyl-9-(2',3'-dihydroxy)propyloxycaronnylindolactam V (20% inhibition at 10 μM);

ix) 14-deshydroxy-14-(2'-hydroxyethylthio)indolactam V (90% inhibition at 10 μM); and x) 14-deshydroxy-14-(2'-hydroxyethylthio)-7-octyl-(9S,12S)-indolactam V (86% inhibition at 1 μM).

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of treatment which comprises the step of administering to a mammal infected by a virus susceptible to such treatment an anti-virally effective quantity of a composition comprising:

a physiologically acceptable pharmaceutical carrier; and a compound, in the form of an individual isomer, an isomer mixture, a racemate or optical antipode, or a pharmaceutically acceptable salt thereof, of the formula:

$$P—G$$

wherein P represents a moiety, formally derived from a parent aromatic heterocyclic compound of the indole, indene, benzofuran or benzothiophene class which contains a substituted or unsubstituted six-atom chain connecting positions 3 and 4 of the indole, indene, benzofuran or benzothiophene skeleton to form an additional 9-membered ring and which optionally contains a nitrogen atom at any of positions 5, 6 and 7 of the benzenoid ring portion of the indole, indene, benzofuran or benzothiophene skeletons wherein the maximum number of nitrogen atoms at positions 5, 6 and 7 is two, which compound:

a. binds reversibly or irreversibly to a diacylglycerol-type receptor; and/or b. activates any form of the enzyme protein kinase C; and c. contains an hydroxymethyl or 1-hydroxyethyl group bonded to a carbon atom; and wherein G is any group of 55 or fewer atoms selected from the group consisting of carbon, hydrogen, oxygen, nitrogen, halogen, sulfur, phosphorus, silicon, arsenic, boron and selenium either: i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group is bound in the parent compound; and wherein the hydroxymethyl or 1-hydroxyethyl group of the parent compound is absent or has been replaced by G;

provided that G may not contain phosphorus bonded to phosphorus, arsenic, boron or silicon, arsenic bonded to arsenic, boron or silicon, halogen bonded to oxygen, nitrogen, sulfur or phosphorus, or bromine, chlorine or iodine bonded to silicon, or oxygen bonded to oxygen, or boron bonded to boron, or silicon bonded to silicon; and provided that: if P is a substituted or unsubstituted indolactam moiety and G is bonded to carbon 9 thereof, then G may not comprise —COOMe, —COOEt or —CH$_2$—R$_e^e$ wherein R$_e^e$ is selected from the group consisting of hydrogen, chloro, bromo, C$_1$–C$_{12}$ saturated or unsaturated, linear or branched alkoxy, CH$_3$OCH$_2$O—, C$_1$–C$_{12}$ linear or branched alkanoyloxy, bromoacetoxy, benzoyloxy, azidobenzoyloxy, 3,5-(CH$_3$)$_2$-C$_6$H$_3$COO—, methanesulfonyloxy, toluenesulfonyloxy, dansyloxy, (tetrahydro-2H-pyran-2-yl)oxy and (C$_1$–C$_6$ linear or branched alkyl)$_n$(phenyl)$_{3-n}$silyloxy wherein n is 0–3.

2. A method of treatment which comprises the step of administering to a mammal infected by a virus susceptible to such treatment an anti-virally effective quantity of a composition comprising:

a physiologically acceptable pharmaceutical carrier; and a compound, in the form of an individual isomer, an isomer mixture, a racemate or optical antipode, or a pharmaceutically acceptable salt thereof, of the formula:

$P_o$—$S_o$—$E_o$ wherein $P_o$ represents a moiety, formally derived from a parent aromatic heterocyclic compound of the indole, indene, benzofuran or benzothiophene class which contains a substituted or unsubstituted six-atom chain connecting positions 3 and 4 of the indole, indene, benzofuran or benzothiophene skeleton to form an additional 9-membered ring and which optionally contains nitrogen atom at any of positions 5, 6 and 7 of the benzenoid ring portion of the indole, indene, benzofuran or benzothiophene skeletons, which compound:

a. binds reversibly or irreversibly to a diacylglycerol-type receptor; and/or b. activates any form of the enzyme protein kinase C; and c. contains an hydroxymethyl or 1-hydroxyethyl group bonded to a carbon atom; and wherein $S_o$—$E_o$ represents a moiety which is either i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group is bound in the parent compound; and wherein $S_o$ is an organic, substituted or unsubstituted, saturated or unsaturated or aromatic, straight or branched, acyclic or ring-containing and/or ring-carrying chain of atoms which separates $P_o$ and $E_o$ by a linear count of at least two but not more than 12 atoms and contains and/or carries not more than 9 heteroatoms selected from the group consisting of oxygen, nitrogen, silicon, sulfur, phosphorus, arsenic, boron and selenium, and carries not more than 16 halogen atoms; provided that the total number of atoms does not exceed 35; and wherein $E_o$ comprises hydrogen, halogen or a saturated or singly or multiply unsaturated group containing up to 15 carbon atoms and optionally containing 1 to 12 halogen atoms and/or optionally containing 1 to 6 heteroatoms selected from the group consisting of oxygen, nitrogen, silicon, sulfur, phosphorus, arsenic, boron and selenium; or wherein $S_oE_o$, taken together, is selected from the group consisting of hydrogen, halogen, thionic sulfur atom or ketonic oxygen atom and a hydroxy, amine or thiol group singly or doubly bonded to the carbon atom of the parent compound $P_o$ in place of the hydroxymethyl or 1-hydroxyethyl group;

provided that $S_oE_o$, taken together, may not contain phosphorus bonded to phosphorus, arsenic, boron or silicon, arsenic bonded to arsenic, boron or silicon, halogen bonded to oxygen, nitrogen, sulfur or phosphorus, or bromine, chlorine or iodine bonded to silicon, or oxygen bonded to oxygen, or boron bonded to boron, or silicon bonded to silicon; and provided that: if $P_o$ is a substituted or unsubstituted indolactam moiety and $S_oE_o$ is bonded to carbon 9 thereof, then $S_oE_o$ may not comprise —COOMe, —COOEt or —CH$_2$—R$_e^e$ wherein R$_e^e$ is selected from the group consisting of hydrogen, chloro, bromo, $C_1$–$C_{12}$ saturated or unsaturated, linear or branched alkoxy, —OCH$_2$OCH$_3$, $C_1$–$C_{12}$ linear or branched alkanoyloxy, bromoacetoxy, benzoyloxy, azidobenzoyloxy, 3,5-(CH$_3$)$_2$-C$_6$H$_3$COO—, methanesulfonyloxy, toluenesulfonyloxy, dansyloxy, (tetrahydro-2H-pyran-2-yl)oxy and ($C_1$–$C_6$ linear or branched alkyl)$_n$(phenyl)$_{3-n}$silyloxy wherein n is 0–3.

3. A method of treatment which comprises the step of administering to a mammal infected by a virus susceptible to such treatment an anti-virally effective quantity of a composition comprising:

a physiologically acceptable pharmaceutical carrier; and a compound of the formula:

$P_2$—$S_4$—$E_1$ wherein $P_2$ is a radical of the formula:

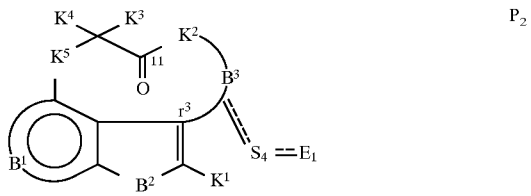

in the form of an individual isomer, an isomer mixture, a racemate or optical antipode, or a pharmaceutically acceptable salt thereof;

wherein $B^1$ completes a 6-membered aromatic ring which may be carbocyclic or may optionally contain a nitrogen atom at any of positions 5, 6 and 7 of the ring wherein the maximum number of nitrogen atoms at positions 5, 6 and 7 is two wherein positions 5, 6 and/or 7 are optionally and independently substituted on any carbon by a halogen and/or on any carbon and/or any nitrogen by straight chain or branched chain, cyclic or acyclic, saturated or unsaturated or aromatic carbon- and/or heteroatom-containing groups which, taken together, contain not more than 40 carbon atoms, not more than 24 halogen atoms, and not more than 9 heteroatoms selected from the group consisting of oxygen, nitrogen, silicon, phosphorus and sulfur, the groups being optionally connected to one another and/or to $B^2$ to form 1–3 additional rings;

$B^2$ is selected from the group consisting of oxygen, sulfur, sulfoxide, sulfone, monofluoromethylene, difluoromethylene, and a carbon or nitrogen atom optionally substituted by straight chain or branched chain, cyclic or acyclic, saturated or unsaturated or aromatic carbon- and/or heteroatom-containing groups having not more than 20 carbon atoms, not more than 24 halogen atoms, and not more than 6 heteroatoms selected from the group consisting of oxygen, nitrogen, silicon, phosphorus and sulfur, and $B^2$ may be linked to $B^1$ or $K^1$ to form an additional carbocyclic or heterocyclic ring;

$B^3$ is a 2-carbon chain, which carries $S_4E_1$, and is optionally substituted by halogen and/or one or more straight chain or branched chain, cyclic or acyclic, saturated or unsaturated or aromatic carbon- and/or heteroatom-containing groups, which groups, taken together but excluding $S_4E_1$, contain not more than 12 carbon atoms, not more than 6 halogen atoms, and not more than 6 heteroatoms selected from the group consisting of oxygen, nitrogen, and sulfur; provided that, including $S_4E_1$, the carbon atom of $B^3$ bonded to $K^2$ as defined below does not carry —CH$_2$OH or —CH(CH$_3$)OH;

$K^1$ is selected from the group consisting of hydrogen, halogen and a straight chain or branched chain, cyclic or acyclic, saturated or unsaturated or aromatic carbon- and/or heteroatom-containing group containing not more than 30 carbon atoms, not more than 18 halogen atoms, and not more than 6 heteroatoms selected from the group consisting of oxygen, nitrogen, silicon, phosphorus and sulfur, and $K^1$ may be linked to $B^2$ or $B^3$ or to both $B^2$ and $B^3$ to form one or more additional carbocyclic and/or heterocyclic rings;

$K^2$ is selected from the group consisting of oxygen, sulfur, —$NK^6$— and —$CK^6K^7$— wherein $K^6$ is selected from the group consisting of hydrogen, hydroxy, methyl, ethyl, fluoro, n-propyl, allyl, and propargyl, and $K^7$ is selected from the group consisting of hydrogen, methyl, ethyl, halogen, trifluoromethyl and cyano;

$K^3$ and $K^4$ are independently selected from the group consisting of hydrogen, halogen and a straight chain or branched chain, cyclic or acyclic, saturated or unsaturated or aromatic carbon- and/or heteroatom-containing group, such that $K^3$ and $K^4$ taken together contain not more than 18 carbon atoms, not more than 24 halogen atoms, and not more than 6 heteroatoms selected from the group consisting of oxygen, nitrogen, silicon, phosphorus and sulfur;

$K^5$ is selected from the group consisting of oxygen, sulfur, sulfoxide, sulfone, —$NK^8$—, —$NOK^8$— and —$CK^8K^9$—, wherein $K^8$ is hydrogen or a straight chain or branched chain, cyclic or acyclic, saturated or unsaturated or aromatic carbon- and/or heteroatom-containing group containing not more than 30 carbon atoms, not more than 24 halogen atoms, and not more than 8 heteroatoms selected from the group consisting of oxygen, nitrogen, silicon, phosphorus and sulfur, and wherein $K^9$ is selected from the group consisting of hydrogen, methyl, ethyl, n-propyl, hydroxy, halogen, allyl, propargyl, cyano and trifluoromethyl;

wherein $S_4$ is a chain of atoms defined by:

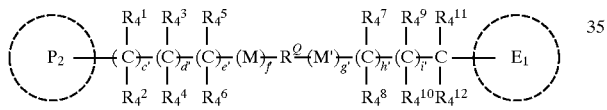

wherein
c', d', e', h', and i' may independently be from 0 to 3;
the sum of (f'+g') must be 1 or 2;
f' and g' may independently be 0 or 1; and
the sum of (c'+d'+e'+f'+g'+h'+i') is at least 1 but not more than 12;

$R_4^1$ through $R_4^{12}$ are independently selected from the group consisting of hydrogen, halogen and a saturated or singly or multiply unsaturated, straight or branched acyclic substituent containing not more than 20 carbon atoms, not more than 16 halogen atoms, and not more than 6 heteroatoms selected from the group consisting of oxygen, nitrogen and sulfur, such that for any substituent the oxygen, nitrogen and sulfur atoms must be situated in functional groups selected from the group consisting of hydroxy, amino, thiol, nitro, azide, ether, thioether, aldehyde, keto, carboxy, ester, amide, cyano, carbonate, carbamate, urea, isourea, carboxamidine, guanidine, thioester, thioamide, thiocarbonate, thiocarbamate, thiourea, nitroguanidine, cyanoguanidine and xanthatee;

$R_4^1$ or $R_4^2$ may optionally comprise an additional bond, thereby completing an unsaturated linkage to the $P_2$ moiety;

one or two of the substituents $R_4^1$–$R_4^{10}$ may optionally comprise the same or different values for $G^1$, as defined below;

$R_4^{11}$ or $R_4^{12}$ may optionally comprise an additional bond, thereby completing an unsaturated linkage to $E_1$;

one of the substituents $R_4^1$–$R_4^{12}$ may be linked to either the atom in $P_2$ that carries the $S_4$ chain or to an atom in $P_2$ adjacent thereto, to form a saturated or unsaturated or aromatic, carbocyclic or heterocyclic 4–8 membered ring containing 0–4 identical or different hetero ring members selected from the group consisting of O, S, SO, $SO_2$, CO, =N— and NH, the ring being optionally substituted on any carbon and/or NH members by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

provided that, for all substituents $R_4^1$ through $R_4^{12}$ and all constituents M, M' and $R^Q$ taken together, but excluding any atoms of the $P_2$ moiety: the total of carbon atoms is 25 or less; the total of halogen atoms is 16 or less; the total of oxygen atoms is 6 or less; the total of nitrogen atoms is 4 or less; the total of sulfuir atoms is 3 or less; the total of oxygen, nitrogen, silicon, phosphorus and sulfur atoms together is 8 or less; the total of —OH groups is 3 or less; the total of —$NH_2$ groups is 2 or less; the total of —SH groups is 2 or less; the total of —OH, —SH, and —$NH_2$ groups together is 4 or less;

wherein M and M' are independently selected from the group consisting of:

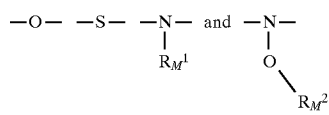

wherein
$R_M^1$ and $R_M^2$ are independently selected from the group consisting of hydrogen and a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, in which the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, ester, amide, cyano, nitroguanidine and cyanoguanidine;

$R_M^1$ may optionally comprise an additional bond, hereby completing an unsaturated linkage to $P_2$;

$R_M^1$ may optionally comprise the same or different values for $G^1$, as defined below;

$R_M^1$ or $R_M^2$ may be linked to either the atom in $P_2$ that carries the chain containing M and/or M' or to an atom in $P_2$ adjacent thereto, to form a saturated or unsaturated or aromatic, carbocyclic or heterocyclic 4–8 membered ring containing 0–4 identical or different hetero ring members selected from the group consisting of O, S, CO, =N— and NH, the ring being optionally substituted on any carbon and/or NH members by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

wherein $R^Q$ is selected from the group consisting of:

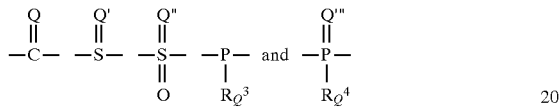

wherein $R_Q^3$ and $R_Q^4$ are independently selected from the group consisting of hydrogen, halogen and a saturated or singly or multiply unsaturated, straight or branched acyclic substituent containing not more than 20 carbon atoms, not more than 16 halogen atoms, and not more than 6 heteroatoms selected from the group consisting of oxygen, nitrogen and sulfur, such that for any substituent the oxygen, nitrogen and sulfur atoms must be situated in functional groups selected from the group consisting of hydroxy, amino, thiol, nitro, azide, ether, thioether, aldehyde, keto, carboxy, ester, amide, cyano, carbonate, carbamate, urea, isourea, carboxamidine, guanidine, thioester, thioamide, thiocarbonate, thiocarbamate, thiourea, nitroguanidine, cyanoguanidine and xanthate;

$R_Q^3$ and/or $R_Q^4$ may optionally comprise the same or different values for $G^1$, as defined below;

one of $R_Q^3$ and $R_Q^4$ may be linked to either the atom in $P_2$ bonded to the chain that carries $R^Q$ or to an atom in $P_2$ adjacent thereto, to form a saturated or unsaturated or aromatic, carbocyclic or heterocyclic 4–8 membered ring containing 0–4 identical or different hetero ring members selected from the group consisting of O, S, SO, $SO_2$, CO, =N— and NH, the ring being optionally substituted on any carbon and/or NH members by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

wherein Q and Q''' are independently selected from the group consisting of:

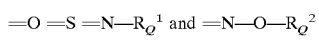

and wherein Q' and Q'' are independently selected from the group consisting of:

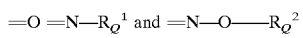

wherein $R_Q^1$ and $R_Q^2$ are independently selected from the group consisting of hydrogen and a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, such that for any substituent the oxygen atoms total 4 or less, the nitrogen atoms total 4 or less, and the sulfur atoms total 2 or less, the heteroatoms being situated in functional groups selected from the group consisting of hydroxy, amino, thiol, nitro, ether, thioether, carboxy, ester, amide, cyano, nitroguanidine and cyanoguanidine;

$R_Q^1$ and/or $R_Q^2$ may optionally comprise the same or different values $G^1$, as defined below;

$R_Q^1$ may be linked to either the atom in $P_2$ that carries the chain containing Q, Q', Q'' and/or Q''' or to an atom in $P_2$ adjacent thereto, to form a saturated or unsaturated or aromatic, carbocyclic or heterocyclic 4–8 membered ring containing 0–4 identical or different hetero ring members selected from the group consisting of O, S, CO, =N— and NH, the ring being optionally substituted on any carbon and/or NH members by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy; and wherein separate rings may be connected to one another and/or to the atom bearing $G^1$ by a single or double bond or by an intervening substituted or unsubstituted, linear or branched chain containing not more than 8 carbon atoms, not more than 8 halogens, and not more than 4 heteroatoms selected from the group consisting of oxygen, nitrogen, silicon, phosphorus and sulfur; and wherein $E_1$ is selected from the group consisting of =O, =S, =NH, =NOH, =N—$NH_2$, hydrogen, halogen, —OH, —SH, —$NH_2$, —NH—$NH_2$, —$N_3$, —CN, —NO, —$NO_2$, —NHOH, —$ONH_2$,

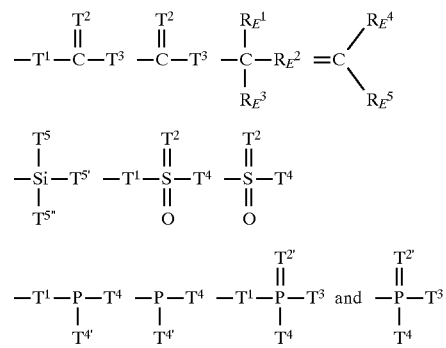

wherein $T^1$ is selected from the group consisting of —O—, —S—, and —NH—;

$T^2$ is selected from the group consisting of =O, =S, and =N—$R_E^6$ wherein $R_E^6$ is selected from the group consisting of hydrogen, hydroxy, cyano and nitro;

$T^{2'}$ is selected from the group consisting of =O and =S;

$T^3$, $T^4$ and $T^{4'}$ are independently selected from the group consisting of —OH, —NH$_2$, —SH, —N$_3$, —NH—NH$_2$, and —NH—OR$_E^7$ wherein R$_E^7$ is selected from the group consisting of hydrogen, C$_{1-3}$ alkyl and C$_{1-3}$ acyl;

$T^3$ may also be hydrogen;

$T^5$–$T^{5''}$ are independently selected from the group consisting of hydrogen and hydroxy;

R$_E^1$ is selected from the group consisting of hydrogen, halogen, hydroxy, nitro, nitroso, cyano, azide, —NH$_2$, —NH—OH, —SH, —O—NH$_2$, —NH—NH$_2$, —T$^1$—C(=T$^2$)—T$^3$, —C(=T$^2$)—T$^3$, —SiT$^5$T$^{5'}$T$^{5''}$, —T$^1$—S(=O)(=T$^2$)—T$^4$, —S(=O)(=T$^2$)—T$^4$, —T$^1$—P(—T$^4$)—T$^{4'}$, —P(—T$^4$)—T$^{4'}$, —T$^1$—P(=T$^{2'}$)(—T$^3$)—T$^4$ and —P(=T$^{2'}$)(—T$^3$)—T$^4$;

R$_E^2$ and R$_E^3$ are individually selected from the group consisting of hydrogen, —C(=T$^2$)—T$^3$, cyano, nitro, azide, halogen and a C$_1$–C$_{15}$ straight or branched chain, saturated or unsaturated or aromatic-containing alkyl moiety optionally containing not more than 10 halogen atoms and not more than 4 heteroatoms selected from the group consisting of oxygen, nitrogen and sulfur;

if R$_E^1$ is cyano or —C(=T$^2$)—T$^3$, then R$_E^2$ or R$_E^3$ may optionally be selected from the group consisting of —SiT$^5$T$^{5'}$T$^{5''}$, —T$^1$—P(=T$^{2'}$) (—T$^3$)—T$^4$ and —P(=T$^{2'}$)(—T$^3$)—T$^4$; and R$_E^4$ and R$_E^5$ are individually selected from the group consisting of hydrogen, halogen, cyano, nitro, —C(=T$^2$)—T$^3$, —T$^1$—C(=T$^2$)—T$^3$, —CR$_E^1$R$_E^2$R$_E^3$, —SiT$^5$T$^{5'}$T$^{5''}$, —S(=O)(=T$^2$)—T$^4$ and —P(=T$^{2'}$)(—T$^3$)—T$^4$;

provided that P$_2$S$_4$E$_1$ may not comprise (–)-1,10,14-N,N,O-trimethylindolactam V; and provided that if, in P$_2$S$_4$E$_1$, B$^1$ completes an unsubstituted or substituted carbocyclic aromatic ring, and B$^2$ is selected from the group consisting of —NH—, —N-(C$_1$–C$_{12}$ linear or branched alkyl or alkanoyl)—, —N—COOCH$_2$C$_6$H$_5$— and —N—COOC(CH$_3$)$_3$—, and B$^3$ is —CH$_2$CH—, and K$^1$ is hydrogen, and K$^2$ is —NH—, and K$^4$ is hydrogen, and K$^5$ is selected from the group consisting of —NH— and —N(C$_1$–C$_3$-alkyl)—, then: (i) if S$_4$E$_1$ is bonded to the carbon atom in B$^3$ that is adjacent to K$^2$, then S$_4$E$_1$ may not be —COOMe or —COOEt; and (ii) if S$_4$ is a single bond directed to the carbon atom in B$^3$ that is adjacent to K$^2$, and E$_1$ is —CH$_2$—R$_e^e$, then R$_e^e$ is not selected from the group consisting of C$_1$–C$_{12}$ linear or branched alkanoyloxy, methanesulfonyloxy and bromoacetoxy.

4. A method of treatment which comprises the step of administering to a mammal infected by a virus susceptible to such treatment an anti-virally effective quantity of a composition, said composition comprising:

a physiologically acceptable pharmaceutical carrier and an aromatic heterocyclic compound of the indole, indene, benzofuran or benzothiophene class which contains a substituted or unsubstituted six-atom chain connecting positions 3 and 4 of the indole, indene, benzofuran or benzothiophene skeleton to form an additional 9-membered ring and which optionally contains a nitrogen atom at any of positions 5, 6 or 7 of the benzenoid ring portion of the indole, indene, benzofuran or benzothiophene skeletons wherein the maximum number of nitrogen atoms at positions 5, 6 and 7 is two, in the form of an individual isomer, an isomer mixture, a racemate or optical antipode, or a pharmaceutically acceptable salt thereof, comprising an antagonist of protein kinase C, a non-inflammatory agonist of protein kinase C, an antagonist for toxic phorboids, or a non-inflammatory phorboid-type agonist, excluding substituted or unsubstituted indolactam derivatives having the following moieties bonded to carbon 9: —CH$_2$OH, —CH(CH$_3$)OH, —COOMe, —COOEt or —CH$_2$—R$_e^e$ in which R$_e^e$ is selected from the group consisting of hydrogen, chloro, bromo, C$_1$–C$_{12}$ saturated or unsaturated, linear or branched alkoxy, CH$_3$OCH$_2$O—, C$_1$–C$_{12}$ linear or branched alkanoyloxy, bromoacetoxy, benzoyloxy, azidobenzoyloxy, 3,5-(CH$_3$)$_2$-C$_6$H$_3$COO—, methanesulfonyloxy, toluenesulfonyloxy, dansyloxy, (tetrahydro-2H-pyran-2-yl)oxy and (C$_1$–C$_6$ linear or branched alkyl)$_n$(phenyl)$_{3-n}$silyloxy wherein n is 0–3; in a quantitiy of between about 0.01–1000 mg per unit dosage.

5. A method of claim 3 wherein S$_4$E$_1$, taken together, either contain a sulfur and/or a phosphorus atom or comprise CH$_2$—M—C(=T$^2$)—M'—R$_a^a$, in which R$_a^a$ is hydrogen or C$_1$–C$_{12}$ linear or branched, saturated or unsaturated or aromatic hydrocarbon optionally substituted by not more than 16 halogens.

6. A method of claim 3 wherein P$_2$ is P$_{2NN}$,

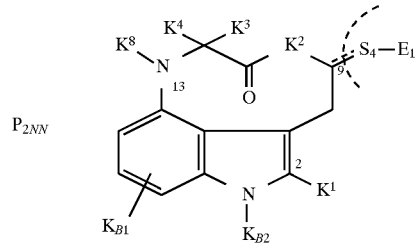

wherein K$_{B1}$ represents 3 identical or different substituents located independently at carbons 5, 6, and/or 7, which substituents may independently be hydrogen, halogen and/or straight chain or branched chain, cyclic or acyclic, saturated, or unsaturated, or aromatic carbon- and/or heteroatom-containing groups which, taken together, contain not more than 40 carbon atoms, not more than 24 halogen atoms, and not more than 9 heteroatoms selected from the group consisting of oxygen, nitrogen, silicon, phosphorus and sulfur, the groups being optionally connected to one another, to K$^8$ and/or to K$_{B2}$ to form 1–3 additional carbocyclic or heterocyclic rings; and wherein K$_{B2}$ is hydrogen or a straight chain or branched chain, cyclic or acyclic, saturated or unsaturated or aromatic carbon- and/or heteroatom-containing group which contains not more than 20 carbon atoms, not more than 24 halogen atoms, and not more than 6 heteroatoms selected from the group consisting of oxygen, nitrogen, silicon, phosphorus and sulfur, this group being optionally connected to K$_{B1}$ or K$^1$ to form an additional carbocyclic or heterocyclic ring.

7. A method of claim 6 wherein S$_4$E$_1$, taken together either contain a sulfur and/or a phosphorus atom or comprise CH$_2$—M—C(=T$^2$)—M'—R$_a^a$ wherein R$_a^a$ is hydrogen or C$_1$–C$_{12}$ linear or branched, saturated or unsaturated or and/or aromatic hydrocarbon optionally substituted by not more than 16 halogens.

8. A method of claim 6 wherein K$^1$ and K$^3$ are hydrogen and K$^2$ is —NH—, forming P$_{2NNN}$

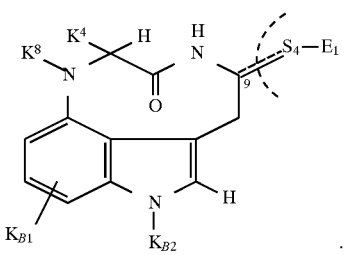

and $K^4$ is hydrogen or a straight or branched chain, cyclic or acyclic, saturated, or unsaturated or and/or aromatic carbon- and/or heteroatom-containing group containing not more than 18 carbon atoms, not more than 24 halogen atoms, and not more than 6 heteroatoms selected from the group consisting of oxygen, nitrogen, silicon, phosphorus and sulfur, the group being optionally connected to $K^8$ to form an additional ring.

9. A method of claim 8 wherein $P_{2NNN}$ is selected from the group consisting of $P_{2L}$ and $P_{2T}$, wherein $P_{2L}$ is

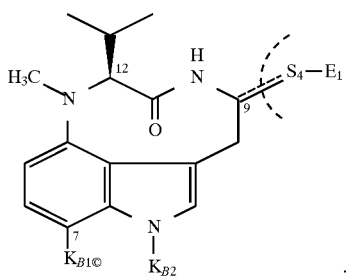

wherein $K_{B1'}$ is hydrogen, halogen or a straight chain or branched chain, cyclic or acyclic, saturated or unsaturated or aromatic carbon- and/or heteroatom-containing group which contains not more than 40 carbon atoms, not more than 24 halogen atoms, and not more than 9 heteroatoms selected from the group consisting of oxygen, nitrogen, silicon, phosphorus and sulfur, this group being optionally connected to $K_{B2}$ to form an additional ring; and wherein $P_{2T}$ is

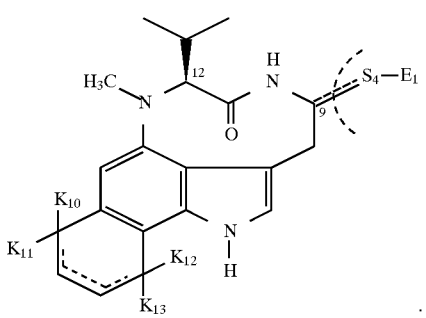

wherein a four-carbon carbocyclic, saturated or unsaturated chain connects positions 6 and 7 and substituents $K_{10}$–$K_{13}$ may independently be absent in favor of unsaturated linkages or may be hydrogen, halogen, and/or a straight chain or branched chain, cyclic or acyclic, saturated or unsaturated or aromatic carbon- and/or heteroatom-containing group which, taken together, contain not more than 36 carbon atoms, not more than 24 halogen atoms, and not more than 9 heteroatoms selected from the group consisting of oxygen, nitrogen, silicon, phosphorus and sulfur.

10. A method of claim 9 wherein $S_4E_1$, taken together either contain a sulfur and/or a phosphorus atom or comprise $CH_2$—M—C(=$T^2$)—M'—$R_a{}^a$, wherein $R_a{}^a$ is hydrogen or $C_1$–$C_{12}$ linear or branched, saturated or unsaturated or aromatic hydrocarbon optionally substituted by not more than 16 halogens.

11. A method of claim 10 wherein $S_4E_1$ taken together comprise an aminocarbonyloxymethylene group or a $C_1$–$C_{10}$ saturated or unsaturated alkyl-, aralkyl-, or arylaminocarbonyloxymethylene group.

12. A method of treatment which comprises the step of administering to a mammal infected by a virus susceptible to such treatment an acceptable pharmaceutical carrier and an anti-virally effective quantity of a compound selected from the group consisting of:

i) teleocidin 14-N-methylcarbamate;
ii) teleocidin 14-N-(n-butyl)carbamate;
iii) lyngbyatoxin A 14-N-methylcarbamate;
iv) lyngbyatoxin A 14-N-(n-butyl)carbamate;
v) rac-14-O-(N-methyl)carbamoylindolactam V;
vi) rac-14-O-(N-methyl)carbamoyl-1-N-(diphenylphosphoryl)indolactam V;
vii) rac-14-O-(N-methyl)carbamoyl-1-N-(2-triphenylphosphonium)ethylindolactam V, methanesulfonate salt;
viii) rac-14-O-(N-methyl)carbamoyl-1-N-trimethylsilylmethylindolactam V;
ix) 14-O-(N-methyl)carbamoyl-7-octyl-(9S,12S)-indolactam V;
x) 14-O-[N-(S)-(1'-naphthyl)ethyl]carbamoyl-7-octyl-(9R,12R)-indolactam V;
xi) 14-O-[N-(S)-(1'-naphthyl)ethyl]carbamoyl-7-octyl-(9S,12S)-indolactam V;
xii) 14-O-[N-(R)-(1'-naphthyl)ethyl]carbamoyl-(9R,12R)-indolactam V;
xiii) 14-O-[N-(R)-(1'-naphthyl)ethyl]carbamoyl-(9S,12S)-indolactam V; and
xiv) 14-O-carbamoyl-7-octyl-(9S,12S)-indolactam V.

13. A method of claim 6 wherein the virus is a retrovirus.
14. A method of claim 7 wherein the virus is a retrovirus.
15. A method of claim 8 wherein the virus is a retrovirus.
16. A method of claim 9 wherein the virus is a retrovirus.
17. A method of claim 10 wherein the virus is a retrovirus.
18. A method of claim 11 wherein the virus is a retrovirus.
19. A method of claim 12 wherein the virus is a retrovirus.
20. A method of claim 13 wherein the retrovirus is a human immunodeficiency virus.
21. A method of claim 14 wherein the retrovirus is a human immunodeficiency virus.
22. A method of claim 15 wherein the retrovirus is a human immunodeficiency virus.
23. A method of claim 16 wherein the retrovirus is a human immunodeficiency virus.
24. A method of claim 17 wherein the retrovirus is a human immunodeficiency virus.
25. A method of claim 18 wherein the retrovirus is a human immunodeficiency virus.
26. A method of claim 19 wherein the retrovirus is a human immunodeficiency virus.

* * * * *